US007674586B2

(12) United States Patent
Warmke et al.

(10) Patent No.: US 7,674,586 B2
(45) Date of Patent: Mar. 9, 2010

(54) **METHODS OF IDENTIFYING MODULATORS OF L-GLUTAMATE-GATED CHLORIDE CHANNEL PROTEINS FROM *RHIPICEPHALUS SANGUINEUS***

(75) Inventors: Jeffrey W. Warmke, Edison, NJ (US); Youfeng Yang, Bethesda, MD (US); Doris F. Cully, Scotch Plains, NJ (US); Michel J. Hamelin, Boulder, CO (US)

(73) Assignee: Merial Limited, Duluth, GA (US)

( * ) Notice: Subject to any disclaimer, the term of this patent is extended or adjusted under 35 U.S.C. 154(b) by 158 days.

(21) Appl. No.: 11/620,390

(22) Filed: Jan. 5, 2007

(65) Prior Publication Data

US 2008/0286770 A1 Nov. 20, 2008

Related U.S. Application Data

(62) Division of application No. 10/239,588, filed as application No. PCT/US01/09905 on Mar. 28, 2001, now Pat. No. 7,202,054.

(60) Provisional application No. 60/193,934, filed on Mar. 31, 2000.

(51) Int. Cl.
*C12Q 1/68* (2006.01)
*C12Q 1/00* (2006.01)

(52) U.S. Cl. .............................. 435/6; 435/4

(58) Field of Classification Search ....................... None
See application file for complete search history.

(56) References Cited

U.S. PATENT DOCUMENTS 5,693,492 A 12/1997 Cully et al.
6,358,701 B1 3/2002 Warmke et al.

FOREIGN PATENT DOCUMENTS

| WO | WO99/07828 | 2/1999 |
| WO | WO01/30849 | 5/2001 |
| WO | WO01/74899 | 10/2001 |
| WO | WO01/96396 | 12/2001 |

OTHER PUBLICATIONS

Database NCBI. Nov. 18, 1997. Accession No. AJ002232, Semenov, et al. Direct submission.

Supplementary European Search Report issued May 4, 2004 in European Patent Application No. 01922781.8.
Drummond, R.O. et al. "Control of ticks systemically with Merck MK-933, an avermectin". J Econ Entomology 74(4):432-436 (1981).
Rohrer, S.P. "Photoaffinity labeling of avermectin binding sites from *Caenorhabditis elegans* and *Drosophila melangaster*". PNAS USA 89:4168-4172 (1992).
Database EMBL. Aug. 17, 1998. "*Lucilia cuprina* glutamate gated chloride chanel mRNA, compete cds." retrieved from EBI Database accession No. AF081674.
Database EMBL. Jun. 7, 1999."Cat flea glutamate gated chloride channel CfGluCI-1 cDNA." retrieved from EBI Database accession No. AAX24372.
Horseman, et al. "The Effects of L-glutamate on cultured insect neurones", Nueroscience Letters, 85, pp. 65-70 (1988).
Cully, et al. "Cloning of an avermectin-sensitive glutamate-gated chloride channel from *Caenorhabditis elegans*", Nature, Vo. 371, pp. 707-711, Oct. 20, 1994.
Cascieri, et al. "Determination of the Amino Acid Residues in Substance P Conferring Selectivity and Specificity for the Rat . . . ", Molec. Pharmacol. vol. 41 pp. 1096-1099 (1992).
Lea, et al. "The Site of Acdtion of Ibotenic Acid and the Identification of Two Populations of Glutamate Receptors . . . ", Comp. Gen. Pharmacol. vol. 41 pp. 333-3450 (1973).
Cull-Candy, "Two Types of Extrajunctional L-Glutamate Receptors in Locust Muscle Fibres", J. Physiol, vol. 255, pp. 449-464 (1976).
Lingle, et al., "A glutamate-activated chloride conductance on a crustacean muscle", Brain Research, 212: 481-488 (1981).
Wafford, et al., "L-Glutamate REceptors on the Cell Body Membrane of an Identified Insect Motor Neurone", J. Exp. Bio. 144: 449-462 (1989).
Cully, et al., "Identification of a *Drosophila melanogaster* Glutamate-gated Chloride Channel Sensitive to the Antiparasitic . . . " J. Biol Chem 271: 20187-20191 (1996).
Arena, et al. "Expression of a glutamate-activated chloride current in *Xenopus oocytes* injected with *Caenorhabditis elegans*. . . ", Molecular Brain Research 15: 339-348 (1992).

*Primary Examiner*—Ruixiang Li
(74) *Attorney, Agent, or Firm*—Judy Jarecki-Black; Merial Limited; Thomas Kowalski

(57) ABSTRACT

The present invention relates in part to isolated nucleic acid molecules (polynucleotides) which encode *Rhipicephalus sanguineus* glutamate gated chloride channels. The present invention also relates to recombinant vectors and recombinant hosts which contain a DNA fragment encoding *R. sanguineus* glutamate gated chloride channels, substantially purified forms of associated *R. sanguineus* glutamate gated chloride channels and recombinant membrane fractions comprising these proteins, associated mutant proteins, and methods associated with identifying compounds which modulate associated *Rhipicephalus sanguineus* glutamate gated chloride channels, which will be useful as insecticides.

4 Claims, 11 Drawing Sheets

>clone T12

```
   1 CGCTCCCCCA ATCCTGAGGT TCCTTCTAAC GAGAAGGAGG AGCCACAGCG CCGGCTGCGG
  61 TACCGCCGCA CGGGCCAACG TGAGACCGCC CGAGCCCGGC GCCCTGACTT AGGCCGCTGA
 121 GCGAAACCCA AGGCGGCGCG CTGGCCACTC CACGGGAACG AGACCGGCCC CCTGGAGACG
 181 ACATCGTCGA CCACAATGAA CTACTTCTCT GACGTGGCGA AGATGGTGGC TTCATCGAAG
 241 AGAGAAATCA TCGAAGCTTT CCACGCGACA TCTGGAGTAC ACGGCGCATG CGAATGAGCG
 301 AACATCGCTG ACCGAGACTC GCCCGTCACC ATGAGCGTAC ATTCATGGCG CTTTTGTGTC
 361 CCACTGGTGG CTCTAGCGTT TTTCTTGTTG ATTCTTCTGT CGTGTCCATC GGCATGGGGC
 421 AAGGCAAATT TCCGCGCTAT AGAAAAGCGG ATATTGGACA GCATCATTGG CCAGGGTCGT
 481 TATGACTGCA GGATCCGGCC CATGGGAATT AACAACACAG ACGGGCCGGC TCTTGTACGC
 541 GTTAACATCT TTGTAAGAAG TATCGGCAGA ATTGATGACG TCACCATGGA GTACACAGTG
 601 CAAATGACGT TCAGAGAGCA GTGGCGGGAC GAGAGACTCC AGTACGACGA CTTGGGCGGC
 661 CAGGTTCGCT ACCTGACGCT CACCGAACCG ACAAGCTTT GGAAGCCGGA CCTGTTTTTC
 721 TCCAACGAGA AAGAGGGACA CTTCCACAAC ATCATCATGC CAACGTGCT TCTACGCATA
 781 CATCCCAACG GCGACGTTCT CTTCAGCATC AGAATATCCT TGGTGCTTTC ATGTCCGATG
 841 AACCTGAAAT TTTATCCTTT GGATAAACAA ATCTGCTCTA TCGTCATGGT GAGCTATGGG
 901 TATACAACAG AGGACCTGGT GTTTCTATGG AAAGAGGGGG ATCCTGTACA GGTCACAAAA
 961 AATCTCCACT TGCCACGTTT CACGCTGGAA AGGTTTCAAA CCGACTACTG CACCAGTCGG
1021 ACCAACACTG GCGAGTACAG CTGCTTGCGC GTGGACCTGG TGTTCAAGCG CGAGTTCAGC
1081 TACTACCTGA TCCAGATCTA CATCCCGTGC TGCATGCTGG TCATCGTGTC CTGGGTGTCG
1141 TTCTGGCTCG ACCCCACCTC GATCCCGGCG CGAGTGTCGC TGGGCGTCAC CACCCTGCTC
1201 ACCATGGCCA CGCAGATATC GGGCATCAAC GCCTCGCTGC CTCCCGTTTC CTACACCAAG
1261 GCCATTGACG TGTGGACCGG CGTCTGTCTG ACCTTCGTAT TCGGCGCGCT CCTCGAGTTC
1321 GCCCTGGTCA ACTACGCCTC GCGGTCAGAT TCACGCCGGC AGAACATGCA GAAGCAGAAG
1381 CAGAGGAAAT GGGAGCTCGA GCCGCCCCTG GACTCGGACC ACCTGGAGGA CGGCGCCACC
1441 ACGTTCGCCA TGAGGCCGCT GGTGCACCAC CACGGAGAGC TGCATGCCGA CAAGTTGCGG
1501 CAGTGCGAAG TCCACATGAA GACCCCCAAG ACGAACCTTT GCAAGGCCTG GCTTTCCAGG
1561 TTTCCCACGC GATCCAAACG CATCGACGTC GTCTCGCGGA TCTTCTTTCC GCTCATGTTC
1621 GCCCTCTTCA ACCTCGTCTA CTGGACAACC TACCTCTTCC GGGAAGACGA GGAAGACGAG
1681 TGACAGAACA CGGACGCCAC GACAGCCGCC ATCGACACC ATCGTCACTG CAGGCACGCA
1741 CTCTGTCGCG CGCACACACC ACGAAGACCG GCGCGCCAAC GCACGATGCG CGTTGGCCGC
1801 TGAAAAACCC GGGAGCGGGG CGGTGGGGGA GGCTATGCCC CGGCCCCTCG CTCCTCATCC
1861 TCCGTGCACG CTCGAATCGT CATCGCCACA GCCAGAAAAA AAAAAGATAC CGTGCGAAAA
1921 GTGGCGGCAA CACAACGTCG ACGCCATCAG CGCCGCCCAG AGCTGCAAGC GGCTCCCACA
1981 TGGTTGCCAC CGCAGCTTCC TCTACGACCC TTCATCCCCA CCGGCACCAG CTACGAGAAA
2041 GGGACCTTAT TTCGGGCCAT CCCTACATAG GCGACTGTTG TTTTCGCACG AAAGATCTTT
2101 ACGCAGCTGA TGCTGAAAAA AAAAAAAAA AAAAAAA (SEQ ID NO:1)
```

MSVHSWRFCVPLVALAFFLLILLSCPSAWGKANFRAIEKRILDSIIGQGRYDCRIRPMGINNTDGPALV
RVNIFVRSIGRIDDVTMEYTVQMTFREQWRDERLQYDDLGGQVRYLTLTEPDKLWKPDLFFSNEKEGHF
HNIIMPNVLLRIHPNGDVLFSIRISLVLSCPMNLKFYPLDKQICSIVMVSYGYTTEDLVFLWKEGDPVQ
VTKNLHLPRFTLERFQTDYCTSRTNTGEYSCLRVDLVFKREFSYYLIQIYIPCCMLVIVSWVSFWLDPT
SIPARVSLGVTTLLTMATQISGINASLPPVSYTKAIDVWTGVCLTFVFGALLEFALVNYASRSDSRRQN
MQKQKQRKWELEPPLDSDHLEDGATTFAMRPLVHHHGELHADKLRQCEVHMKTPKTNLCKAWLSRFPTR
SKRIDVVSRIFFPLMFALFNLVYWTTYLFREDEEDE* (SEQ ID NO:2)

FIG.2

>clone T82

```
   1 CACACCTCCT GCGTCTCTCC ACTCGATGAA GACCTGTCCC GGAGGCGCGA GCCCAACTGC
  61 GCGCTCTGTC CGCATGTGTC GCCGCCACTG AGAGGCCTCC GGCGTGGCGC GCTTGTCAAC
 121 GCGGCGCGCC GGCCCGCAGC AAATCGCGGG CATTCCACTC AGGGTCTCAT TCGCTCCCCC
 181 AATCCTGAGG TTCCTTCTAA CGAGAAGGAG GAGCCACAGC GCCGGCTGCG GTACCGCCGC
 241 ACGGGCCAAC GTGAGACCGC CCGAGCCCGG CGCCCTGACT TAGGCCGCTG AGCGAAACCC
 301 AAGGCGGCGC GCTGGCCACT CCACGGGAAC GAGACCGGCC CCCTGGAGAC GACATCGTCG
 361 ACCACAATGA ACTACTTCTC TGACGTGGCG AAGATGGTGG CTTCATCGAA GAGAGAAATC
 421 ATCGAAGCTT TCCACGCGAC ATCTGGAGTA CACGGCGCAT GCGAATGAGC GAACATCGCT
 481 GACCGAGACT CGCCCGTCAC CATGAGCGTA CATTCATGGC GCTTTTGTGT CCCACTGGTG
 541 GCTCTAGCGT TTTTCTTGTT GATTCTTCTG TCGTGTCCAT CGGCATGGGG CAAGGCAAAT
 601 TTCCGCGCTA TAGAAAAGCG GATATTGGAC AGCATCATTG CCAGGGTCG TTATGACTGC
 661 AGGATCCGGC CCATGGGAAT TAACAACACA GACGGGCCGG CTCTTGTACG CGTTAACATC
 721 TTTGTAAGAA GTATCGGCAG AATTGATGAC GTCACCATGG AGTACACAGT GCAAATGACG
 781 TTCAGAGAGC AGTGGCGGGA CGAGAGACTC CAGTACGACG ACTTGGGCGG CCAGGTTCGC
 841 TACCTGACGC TCACCGAACC GGACAAGCTT TGGAAGCCGG ACCTGTTTTT CTCCAACGAG
 901 AAAGAGGGAC ACTTCCACAA CATCATCATG CCCAACGTGC TTCTACGCAT ACATCCCAAC
 961 GGCGACGTTC TCTTCAGCAT CAGAATATCC TTGGTGCTTT CATGTCCGAT GAACCTGAAA
1021 TTTTATCCTT TGGATAAACA AATCTGCTCT ATCGTCATGG TGAGCTATGG GTATACAACA
1081 GAGGACCTGG TGTTTCTATG GAAAGAGGGG GATCCTGTAC AGGTCACAAA AAATCTCCAC
1141 TTGCCACGTT TCACGCTGGA AAGGTTTCAA ACCGACTACT GCACCAGTCG GACCAACACT
1201 GGCGAGTACA GCTGCTTGCG CGTGGACCTG GTGTTCAAGC GCGAGTTCAG CTACTACCTG
1261 ATCCAGATCT ACATCCCGTG CTGCATGCTG GTCATCGTGT CCTGGGTGTC GTTCTGGCTC
1321 GACCCCACCT CGATCCCGGC GCGAGTGTCG CTGGGCGTCA CCACCCTGCT CACCATGGCC
1381 ACGCAGATAT CGGGCATCAA CGCCTCGCTG CCTCCCGTTT CCTACACCAA GGCCATTGAC
1441 GTGTGGACCG GCGTCTGTCT GACCTTCGTA TTCGGCGCGC TCCTCGAGTT CGCCCTGGTC
1501 AACTACGCCT CGCGGTCAGA TTCACGCCGG CAGAACATGC AGAAGCAGAA GCAGAGGAAA
1561 TGGGAGCTCG AGCCGCCCCT GGACTCGGAC CACCTGGAGG ACGGCGCCAC CACGTTCGCC
1621 ATGAGGCCGC TGGTGCACCA CCACGGAGAG CTGCATGCCG ACAAGTTGCG GCAGTGCGAA
1681 GTCCACATGA AGACCCCCAA GACGAACCTT TGCAAGGCCT GGCTTTCCAG GTTTCCCACG
1741 CGATCCAAAC GCATCGACGT CGTCTCGCGG ATCTTCTTTC CGCTCATGTT CGCCCTCTTC
1801 AACCTCGTCT ACTGGACAAC CTACCTCTTC CGGGAAGACA AGGAAGACGA GTGACAGAAC
1861 ACGAACGCCA CGACAGCCGC CATCCGACAC CATCGTCACT GCAGGCACGC ACTCTGTCGC
1921 GCGCACACAC CACGAAGACC GGCGCGCCAA CGCACGATGC GCGTTGGCCG CTGAAAAACC
1981 CGGGAGCGGG GCGGTGGGGG AGGCTATGCC CCGGCCCCTC GCTCCTCATC CTCCGTGCAC
2041 GCTCGAATCG TCATCGCCAC AGCCAGAAAA AAAAAAGATA CCGTGCGAAA AGTGGCGGCA
2101 ACACAACGTC GACGCCATCA GCGCCGCCCA GAGCTGCAAG CGGCTCCCAC ATGGTTGCCA
2161 CCGCAGCTTC CTCTACGACC CTTCATCCCC ACCGGCACCA GCTACGAGAA AGGGACCTTA
2221 TTTCGGGCCA TCCCTACATA GGCGACTGTT GTTTTCGCAC GAAAGATCTT TACGCAGCTG
2281 ATGCTGAAA (SEQ ID NO:3)
```

MSVHSWRFCVPLVALAFFLLILLSCPSAWGKANFRAIEKRILDSIIGQGRYDCRIRPMGINNTDGPALV
RVNIFVRSIGRIDDVTMEYTVQMTFREQWRDERLQYDDLGGQVRYLTLTEPDKLWKPDLFFSNEKEGHF
HNIIMPNVLLRIHPNGDVLFSIRISLVLSCPMNLKFYPLDKQICSIVMVSYGYTTEDLVFLWKEGDPVQ
VTKNLHLPRFTLERFQTDYCTSRTNTGEYSCLRVDLVFKREFSYYLIQIYIPCCMLVIVSWVSFWLDPT
SIPARVSLGVTTLLTMATQISGINASLPPVSYTKAIDVWTGVCLTFVFGALLEFALVNYASRSDSRRQN
MQKQKQRKWELEPPLDSDHLEDGATTFAMRPLVHHHGELHADKLRQCEVHMKTPKTNLCKAWLSRFPTR
SKRIDVVSRIFFPLMFALFNLVYWTTYLFREDKEDE* (SEQ ID NO:4)

FIG.4

>clone T32

```
   1 CAGGCTCCGG CGTGACTGTC GCTCGCTCGG CTCTCGACGC TCGCGGCGGG AACAACCGCT
  61 ACCCGGACGC TCGATCAGGA GCAGTTCGGG CCACAGAGAA AGGGGCCGAG GAGTGCACAC
 121 CTCCTGCGTC TCTCCACTCG ATGAAGACCT GTCCCGGAGG CGCGAGCCCA ACTGCGCGCT
 181 CTGTCCGCAT GTGTCGCCGC CACTGAGAGG CCTCCGGCGT GGCGCGCTTG TCAACGCGGC
 241 GCGCCGGCCC GCAGCAAATC GCGGGCATTC CACTCAGGGT CTCATTCGCT CCCCCAATCC
 301 TGAGGTTCCT TCTAACGAGA AGGAGGAGCC ACAGCGCCGG CTGCGGTACC GCCGCACGGG
 361 CCAACGTGAG ACCGCCCGAG CCCGGCGCCC TGACTTAGGC CGCTGAGCGA AACCCAAGGC
 421 GGCGCGCTGG CCACTCCACG GGAACGAGAC CGGCCCCCTG GAGACGACAT CGTCGACCAC
 481 AATGAACTAC TTCTCTGACG TGGCGAAGAT GGTGGCTTCA TCGAAGAGAG AAATCATCGA
 541 AGCTTTCCAC GCGACATCTG GAGTACACGG CGCATGCGAA TGAGCGAACA TCGCTGACCG
 601 AGACTCGCCC GTCACCATGA GCGTACATTC ATGGCGCTTT TGTGTCCCAC TGGTGGCTCT
 661 AGCGTTTTTC TTGTTGATTC TTCTGTCGTG TCCATCGGCA TGGGCCGAAA CGCTGCCTAC
 721 GCCACCAACC CGTGGCCAGG GGGGCGTTCC GGTCGCGGCC GCGATGCTCC TGGGGAAACA
 781 GCAAAGTTCC CGCTACCAAG ATAAAGAGGG CAAGGCAAAT TTCCGCGCTA TAGAAAAGCG
 841 GATATTGGAC AGCATCATTG GCCAGGGTCG TTATGACTGC AGGATCCGGC CATGGGAAT
 901 TAACAACACA GACGGGCCGG CTCTTGTACG CGTTAACATC TTTGTAAGAA GTATCGGCAG
 961 AATTGATGAC GTCACCATGG AGTACACAGT GCAAATGACG TTCAGAGAGC AGTGGCGGGA
1021 CGAGAGACTC CAGTACGACG ACTTGGGCGG CCAGGTTCGC TACCTGACGC TCACCGAACC
1081 GGACAAGCTT TGGAAGCCGG ACCTGTTTTT CTCCAACGAG AAAGAGGGAC ACTTCCACAA
1141 CATCATCATG CCCAACGTGC TTCTACGCAT ACATCCCAAC GGCGACGTTC TCTTCAGCAT
1201 CAGAATATCC TTGGTGCTTT CATGTCCGAT GAACCTGAAA TTTTATCCTT TGGATAAACA
1261 AATCTGCTCT ATCGTCATGG TGAGCTATGG GTATACAACA GAGGACCTGG TGTTTCTATG
1321 GAAAGAGGGG GATCCTGTAC AGGTCACAAA AAATCTCCAC TTGCCACGTT TCACGCTGGA
1381 AAGGTTTCAA ACCGACTACT GCACCAGTCG GACCAACACT GGCGAGTACA GCTGCTTGCG
1441 CGTGGACCTG GTGTTCAAGC GCGAGTTCAG CTACTACCTG ATCCAGATCT ACATCCCGTG
1501 CTGCATGCTG GTCATCGTGT CCTGGGTGTC GTTCTGGCTC GACCCCACCT CGATCCCGGC
1561 GCGAGTGTCG CTGGGCGTCA CCACCCTGCT CACCATGGCC ACGCAGATAT CGGGCATCAA
1621 CGCCTCGCTG CCTCCCGTTT CCTACACCAA GGCCATTGAC GTGTGGACCG GCGTCTGTCT
1681 GACCTTCGTA TTCGGCGCGC TCCTCGAGTT CGCCCTGGTC AACTACGCCT CGCGGTCAGA
1741 TTCACGCCGG CAGAACATGC AGAAGCAGAA GCAGAGGAAA TGGGAGCTCG AGCCGCCCCT
1801 GGACTCGGAC CACCTGGAGG ACGGCGCCAC CACGTTCGCC ATGGTGAGCT CCGGCGAGCC
1861 GGCGGGCCTC ATGGCGCGAA CCTGGCCACC ACCGCCGCTG CCGCCAAACA TGGCGGCCGG
1921 CTCCGCGCAA GCCGGCGCCA GGCCGCTGGT GCACCACCAC GGAGAGCTGC ATGCCGACAA
1981 GTTGCGGCAG TGCGAAGTCC ACATGAAGAC CCCCAAGACG AACCTTTGCA AGGCCTGGCT
2041 TTCCAGGTTT CCCACGCGAT CCAAACGCAT CGACGTCGTC TCGCGGATCT TCTTTCCGCT
2101 CGTGTTCGCC CTCTTCAACC TCGTCTACTG GACAACCTAC CTCTTCCGGG AAGACGAGGA
2161 GGACGAGTGA CAGAACACGA ACGCCACGAC AGCCGCCATC CGACACCATC GTCACTGCAG
2221 GCACGCACTC TGTCGCGCGC ACACACCACG AAGACCGGCG CGCCAACGCA CGATGCGCGT
2281 TGGCCGCTGA AAAACCCGGG AGCGGGGCGG TGGGGGAGGC TATGCCCCGG CCCCTCGCTC
2341 CTCATCCTCC GTGCACGCTC GAATCGTCAT CGCCACAGCC AGAAAAAAAA AAAAAAAAAA
(SEQ ID NO:5)
```

MSVHSWRFCVPLVALAFFLLILLSCPSAWAETLPTPPTRGQGGVPVAAAMLLGKQQSSRYQDKEGKANF
RAIEKRILDSIIGQGRYDCRIRPMGINNTDGPALVRVNIFVRSIGRIDDVTMEYTVQMTFREQWRDERL
QYDDLGGQVRYLTLTEPDKLWKPDLFFSNEKEGHFHNIIMPNVLLRIHPNGDVLFSIRISLVLSCPMNL
KFYPLDKQICSIVMVSYGYTTEDLVFLWKEGDPVQVTKNLHLPRFTLERFQTDYCTSRTNTGEYSCLRV
DLVFKREFSYYLIQIYIPCCMLVIVSWVSFWLDPTSIPARVSLGVTTLLTMATQISGINASLPPVSYTK
AIDVWTGVCLTFVFGALLEFALVNYASRSDSRRQNMQKQKQRKWELEPPLDSDHLEDGATTFAMVSSGE
PAGLMARTWPPPPLPPNMAAGSAQAGARPLVHHHGELHADKLRQCEVHMKTPKTNLCKAWLSRFPTRSK
RIDVVSRIFFPLVFALFNLVYWTTYLFREDEEDE*(SEQ ID NO:6)

```
   1 CGCCGCTCAA TCGCGGGCTA CGGACTCGTC GTTCCCGGAG GGGCTTGGAC
  51 CACAGCTCGC TCGTCACCGT GGTGGCTGGC CGCTTCGCCT GGCGGTCCTG
 101 CACGCACGCT GTAACGAACG TCGCCACGCG ATGTTTGGTG TGCCATGCTC
 151 CCGCGCCTGC CGCCTTGTGG TGGTGATAGC TGCGTTCTGC TGGCCGCCCG
 201 CTCTGCCGCT CGTACCCGGG GGAGTTTCCT CCAGAGCAAA CGATCTGGAC
 251 ATTCTGGACG AGCTCCTCAA AAACTACGAT CGAAGGGCCC TGCCGAGCAG
 301 TCACCTCGGA AATGCAACTA TTGTGTCATG CGAAATTTAC ATACGAAGTT
 351 TTGGATCAAT AAATCCTTCG AACATGGACT ACGAAGTCGA CCTCTACTTC
 401 CGGCAGTCGT GGCTCGACGA GCGGTTACGC AAATCCACGC TATCTCGTCC
 451 GCTCGACCTT AATGACCCAA AGCTGGTACA AATGATATGG AAGCCAGAAG
 501 TTTTCTTTGC GAACGCGAAA CACGCCGAGT TCCAATATGT GACTGTACCT
 551 AACGTCCTCG TTAGGATCAA CCCGACTGGA ATAATCTTGT ACATGTTGCG
 601 GTTAAAACTG AGGTTCTCCT GCATGATGGA CCTGTACCGG TACCCCATGG
 651 ATTCCCAAGT CTGCAGCATC GAAATTGCCT CTTTTTCCAA AACCACCGAA
 701 GAGCTGCTGC TGAAATGGTC CGAGAGTCAG CCTGTCGTTC TCTTCGATAA
 751 CCTCAAGTTG CCCCAGTTTG AAATAGAGAA GGTGAACACG TCCTTATGCA
 801 AAGAAAAGTT TCACATAGGG GAATACAGTT GCCTGAAAGC CGACTTCTAT
 851 CTGCAGCGTT CCCTCGGTTA TCACATGGTG CAGACCTATC TTCCGACCAC
 901 GCTTATCGTG GTCATCTCAT GGGTGTCATT CTGGCTCGAC GTAGACGCCA
 951 TACCCGCCCG TGTCACCCTG GGCGTAACCA CGCTGCTCAC CATCTCATCC
1001 AAGGGTGCCG GTATCCAGGG AAACCTGCCT CCCGTCTCGT ACATCAAGGC
1051 CATGGACGTC TGGATAGGAT CCTGTACTTC GTTTGTCTTT GCGGCCCTTC
1101 TAGAGTTCAC ATTCGTCAAC TATCTCTGGA GGCGGCTGCC CAATAAGCGC
1151 CCATCTTCTG ACGTACCGGT GACGGATATA CCAAGCGACG GCTCAAAGCA
1201 TGACATTGCG GCACAGCTCG TACTCGACAA GAATGGACAC ACCGAAGTTC
1251 GCACGTTGGT CCAAGCGATG CCACGCAGCG TCGGAAAAGT GAAGGCCAAG
1301 CAGATTGATC AACTCAGCCG AGTCGCCTTT CCCGCTCTTT TTCTCCTCTT
1351 CAACCTCGTG TACTGGCCGT ACTACATTAA GTCATAAAGA ACGTAGTTTT
1401 CT (SEQ ID NO:7)
```

MFGVPCSRACRLVVVIAAFCWPPALPLVPGGVSSRANDLDILDEL
LKNYDRRALPSSHLGNATIVSCEIYIRSFGSINPSNMDYEVDLYF
RQSWLDERLRKSTLSRPLDLNDPKLVQMIWKPEVFFANAKHAEFQ
YVTVPNVLVRINPTGIILYMLRLKLRFSCMMDLYRYPMDSQVCSI
EIASFSKTTEELLLKWSESQPVVLFDNLKLPQFEIEKVNTSLCKE
KFHIGEYSCLKADFYLQRSLGYHMVQTYLPTTLIVVISWVSFWLD
VDAIPARVTLGVTTLLTISSKGAGIQGNLPPVSYIKAMDVWIGSC
TSFVFAALLEFTFVNYLWRRLPNKRPSSDVPVTDIPSDGSKHDIA
AQLVLDKNGHTEVRTLVQAMPRSVGKVKAKQIDQLSRVAFPALFL
LFNLVYWPYYIKS (SEQ ID NO:8)

FIG.8

```
T32  MS.VHSWRFCVPLVALAFFLLILLSCPSAWAETLPTPPTRGQGGVPVAAAMLLGKQQSSR
T12  MS.VHSWRFCVPLVALAFFLLILLSCPSAW...............................
T82  MS.VHSWRFCVPLVALAFFLLILLSCPSAW...............................
B1   MFGVPCSRACRLVVVIAAFC.....WPPALPLVP...........................

T32  YQDKEGKANFRAIEKRILDSIIGQGRYDCRIRP...MGINNTDGPALVRVNIFVRSIGRI
T12  ...GKANFRAIEKRILDSIIGQGRYDCRIRP...MGINNTDGPALVRVNIFVRSIGRI
T82  .....GKANFRAIEKRILDSIIGQGRYDCRIRP...MGINNTDGPALVRVNIFVRSIGRI
B1   .....GGVSSRANDLDILDELLKN..YDRRALPSSHLG.NAT....IVSCEIYIRSFGSI

T32  DDVTMEYTVQMTFREQWRDERLQYDDLGGQVRYLTLTEPDKL....WKPDLFFSNEKEGH
T12  DDVTMEYTVQMTFREQWRDERLQYDDLGGQVRYLTLTEPDKL....WKPDLFFSNEKEGH
T82  DDVTMEYTVQMTFREQWRDERLQYDDLGGQVRYLTLTEPDKL....WKPDLFFSNEKEGH
B1   NPSNMDYEVDLYFRQSWLDERLRKSTLS...RPLDLNDP.KLVQMIWKPEVFFANAKHAE

T32  FHNIIMPNVLLRIHPNGDVLFSIRISLVLSCPMNLKFYPLDKQICSIVMVSYGYTTEDLV
T12  FHNIIMPNVLLRIHPNGDVLFSIRISLVLSCPMNLKFYPLDKQICSIVMVSYGYTTEDLV
T82  FHNIIMPNVLLRIHPNGDVLFSIRISLVLSCPMNLKFYPLDKQICSIVMVSYGYTTEDLV
B1   FQYVTVPNVLVRINPTGIILYMLRLKLRFSCMMDLYRYPMDSQVCSIEIASFSKTTEELL

T32  FLWKEGDPVQVTKNLHLPRFTLERFQTDYCTSRTNTGEYSCLRVDLVFKREFSYYLIQIY
T12  FLWKEGDPVQVTKNLHLPRFTLERFQTDYCTSRTNTGEYSCLRVDLVFKREFSYYLIQIY
T82  FLWKEGDPVQVTKNLHLPRFTLERFQTDYCTSRTNTGEYSCLRVDLVFKREFSYYLIQIY
B1   LKWSESQPVVLFDNLKLPQFEIEKVNTSLCKEKFHIGEYSCLKADFYLQRSLGYHMVQTY

T32  IPCCMLVIVSWVSFWLDPTSIPARVSLGVTTLLTMATQIS....GINASLPPVSYTKAID
T12  IPCCMLVIVSWVSFWLDPTSIPARVSLGVTTLLTMATQIS....GINASLPPVSYTKAID
T82  IPCCMLVIVSWVSFWLDPTSIPARVSLGVTTLLTMATQIS....GINASLPPVSYTKAID
B1   LPTTLIVVISWVSFWLDVDAIPARVTLGVTTLLT....ISSKGAGIQGNLPPVSYIKAMD

T32  VWTGVCLTFVFGALLEFALVNYASRSDSRRQNMQKQKQRKWELEPPLDS...DHLEDG.A
T12  VWTGVCLTFVFGALLEFALVNYASRSDSRRQNMQKQKQRKWELEPPLDS...DHLEDG.A
T82  VWTGVCLTFVFGALLEFALVNYASRSDSRRQNMQKQKQRKWELEPPLDS...DHLEDG.A
B1   VWIGSCTSFVFAALLEFTFVNYLWR...RLPNK.....R.....PSSDVPVTDIPSDGSK

T32  TTFAMVSSGEPAGLMARTWPPPPLPPNMAAGSAQAGARPLVHHHGELHADKLRQCEVHMK
T12  TTFAM...........................RPLVHHHGELHADKLRQCEVHMK
T82  TTFAM...........................RPLVHHHGELHADKLRQCEVHMK
B1   HDIAAQ...............................LVLDKNGHTEVR..

T32  TPKTNLCKAWLSRFPTRS......KRIDVVSRIFFPLVFALFNLVYWTTYLFREDEEDE (SEQ ID NO:6)
T12  TPKTNLCKAWLSRFPTRS......KRIDVVSRIFFPLMFALFNLVYWTTYLFREDEEDE (SEQ ID NO:2)
T82  TPKTNLCKAWLSRFPTRS......KRIDVVSRIFFPLMFALFNLVYWTTYLFREDKEDE (SEQ ID NO:4)
B1      T.LVQAMP.....RSVGKVKAKQIDQLSRVAFPALFLLFNLVYWPYYIKS...    (SEQ ID NO:8)
```

FIG.9

METHODS OF IDENTIFYING MODULATORS OF L-GLUTAMATE-GATED CHLORIDE CHANNEL PROTEINS FROM *RHIPICEPHALUS SANGUINEUS*

CROSS-REFERENCE TO RELATED APPLICATIONS

The present application is a divisional application of U.S. application Ser. No. 10/239,588, filed Sep. 23, 2002, now U.S. Pat. No. 7,202,054, which is the §371 National Stage prosecution of PCT International Application Serial No. PCT/US01/09905, having an international filing date of Mar. 28, 2001, which claims priority under 35 U.S.C. § 119(e), to provisional application U.S. Ser. No. 60/193,934, filed Mar. 31, 2000, now expired.

STATEMENT REGARDING FEDERALLY-SPONSORED R&D

Not Applicable

REFERENCE TO MICROFICHE APPENDIX

Not Applicable

FIELD OF THE INVENTION

The present invention relates in part to isolated nucleic acid molecules (polynucleotides) which encode *Rhipicephalus sanguineus* (brown dog tick) glutamate-gated chloride channels. The present invention also relates to recombinant vectors and recombinant hosts which contain a DNA fragment encoding *R. sanguineus* glutamate-gated chloride channels, substantially purified forms of associated *R. sanguineus* glutamate-gated chloride channels and recombinant membrane fractions comprising these proteins, associated mutant proteins, and methods associated with identifying compounds which modulate associated *Rhipicephalus sanguineus* glutamate-gated chloride channels, which will be useful as insecticides.

BACKGROUND OF THE INVENTION

Glutamate-gated chloride channels, or H-receptors, have been identified in arthropod nerve and muscle (Lingle et al, 1981, *Brain Res.* 212: 481-488; Horseman et al., 1988, *Neurosci. Lett.* 85: 65-70; Wafford and Sattelle, 1989, *J. Exp. Bio.* 144: 449-462; Lea and Usherwood, 1973, *Comp. Gen. Parmacol.* 4: 333-350; and Cull-Candy, 1976, *J. Physiol.* 255: 449-464).

Invertebrate glutamate-gated chloride channels are important targets for the widely used avermectin class of anthelmintic and insecticidal compounds. The avermectins are a family of macrocyclic lactones originally isolated from the actinomycete *Streptomyces avermitilis*. The semisynthetic avermectin derivative, ivermectin (22,23-dihydro-avermectin $B_{1a}$), is used throughout the world to treat parasitic helminths and insect pests of man and animals. The avermectins remain the most potent broad spectrum endectocides exhibiting low toxicity to the host. After many years of use in the field, there remains little resistance to avermectin in the insect population. The combination of good therapeutic index and low resistance strongly suggests that the glutamate-gated chloride (GluCl) channels remain good targets for insecticide development.

Glutamate-gated chloride channels have been cloned from the soil nematode *Caenorhabditis elegans* (Cully et al., 1994, *Nature* 371: 707-711; see also U.S. Pat. No. 5,527,703 and Arena et al., 1992, *Molecular Brain Research.* 15: 339-348) and *Ctenocephalides felis* (flea; see WO 99/07828).

In addition, a gene encoding a glutamate-gated chloride channel from *Drosophila melanogaster* was previously identified (Cully et al., 1996, *J. Biol. Chem.* 271: 20187-20191; see also U.S. Pat. No. 5,693,492).

Despite the identification of the aforementioned cDNA clones encoding GluCl channels, it would be advantageous to identify additional genes which encode *R. sanguineus* GluCl channels in order to allow for improved screening to identify novel GluCl channel modulators that may have insecticidal, acaricidal and/or nematocidal activity for animal health, especially as related to treatment of tick and mite infestation in dogs, cats, cattle, sheep and other agriculturally important animals. The present invention addresses and meets these needs by disclosing novel genes which express a *R. sanguineus* GluGl1 and *R. sanguineus* GluGl2 channel wherein expression of these *R. sanguineus* GluCl RNAs in *Xenopus* oocytes or other appropriate host cells result in an active GluCl channel. Heterologous expression of a GluCl channel of the present invention will allow the pharmacological analysis of compounds active against parasitic invertebrate species relevant to animal and human health, especially in the treatment of tick infestations in dogs and cats. Heterologous cell lines expressing an active GluCl channel can be used to establish functional or binding assays to identify novel GluCl channel modulators that may be useful in control of the aforementioned species groups.

SUMMARY OF THE INVENTION

The present invention relates to an isolated or purified nucleic acid molecule (polynucleotide) which encodes a novel *Rhipicephalus sanguineus* (brown dog tick) invertebrate GluCl1 channel protein. The DNA molecules disclosed herein may be transfected into a host cell of choice wherein the recombinant host cell provides a source for substantial levels of an expressed functional single, homomultimeric or heteromultimeric LGIC. Such functional ligand-gated ion channels may possibly respond to other known ligands which will in turn provide for additional screening targets to identify modulators of these channels, modulators which may act as effective insecticidal, mitacidal and/or nematocidal treatment for use in animal and human health and/or crop protection.

The present invention relates to an isolated or purified nucleic acid molecule (polynucleotide) which encodes a novel *Rhipicephalus sanguineus* invertebrate GluCl2 channel protein.

The present invention further relates to an isolated nucleic acid molecule (polynucleotide) which encodes mRNA which expresses a novel *Rhipicephalus sanguineus* GluCl1 channel protein, this DNA molecule comprising the nucleotide sequence disclosed herein as SEQ ID NO:1, SEQ ID NO:3, and SEQ ID NO:5.

The present invention further relates to an isolated nucleic acid molecule (polynucleotide) which encodes mRNA which expresses a novel *Rhipicephalus sanguineus* GluCl2 channel protein, this DNA molecule comprising the nucleotide sequence disclosed herein as SEQ ID NO:7.

The present invention also relates to biologically active fragments or mutants of SEQ ID NOs:1, 3, 5 and 7 which encodes mRNA expressing a novel *Rhipicephalus sanguineus* invertebrate GluCl1 or GluCl2 channel protein, respectively. Any such biologically active fragment and/or mutant will encode either a protein or protein fragment which at least substantially mimics the pharmacological properties of a *R. sanguineus* GluCl channel protein, including but not limited to the *R. sanguineus* GluCl1 channel proteins as set forth in SEQ ID NO:2, SEQ ID NO:4, and SEQ ID NO:6 as well as the respective GluCl2 channel protein as set forth in SEQ ID NO:8. Any such polynucleotide includes but is not necessarily limited to nucleotide substitutions, deletions, additions, amino-terminal truncations and carboxy-terminal truncations such that these mutations encode mRNA which express a functional *R. sanguineus* GluCl channel in a eukaryotic cell, such as *Xenopus* oocytes, so as to be useful for screening for agonists and/or antagonists of *R. sanguineus* GluCl activity.

A preferred aspect of this portion of the present invention is disclosed in FIG. 1 (SEQ ID NO:1; designated T12), FIG. 3 (SEQ ID NO:3; designated T82) and FIG. 5 (SEQ ID NO:5; designated T32) encoding novel *Rhipicephalus sanguineus* GluCl1 proteins, and FIG. 7 (SEQ ID NO:7, designated B1) encoding a novel *Rhipicephalus sanguineus* GluCl2 protein.

The isolated nucleic acid molecules of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

The present invention also relates to recombinant vectors and recombinant host cells, both prokaryotic and eukaryotic, which contain the substantially purified nucleic acid molecules disclosed throughout this specification.

The present invention also relates to a substantially purified form of an *R. sanguineus* GluCl1 channel protein, which comprises the amino acid sequence disclosed in FIG. 2 (SEQ ID NO:2), FIG. 4 (SEQ ID NO:4) and FIG. 6 (SEQ ID NO:6), as well as to a novel *Rhipicephalus sanguineus* GluCl2 protein, which comprises the amino acid sequence disclosed in FIG. 8 (SEQ ID NO:8).

A preferred aspect of this portion of the present invention is a *R. sanguineus* GluCl1 channel protein which consists of the amino acid sequence disclosed in FIG. 2 (SEQ ID NO:2), FIG. 4 (SEQ ID NO:4) and FIG. 6 (SEQ ID NO:6).

Another preferred aspect of this portion of the present invention is a *R. sanguineus* GluCl2 channel protein which consists of the amino acid sequence disclosed in FIG. 8 (SEQ ID NO:8).

Another preferred aspect of the present invention relates to a substantially purified, fully processed (including any proteolytic processing, glycosylation and/or phosphorylation) mature GluCl channel protein obtained from a recombinant host cell containing a DNA expression vector comprises a nucleotide sequence as set forth in SEQ ID NOs: 1, 3, 5 and/or 7 and expresses the respective RsGluCl1 or RsGluCl2 precursor protein. It is especially preferred that the recombinant host cell be a eukaryotic host cell, including but not limited to a mammalian cell line, an insect cell line such as an S2 cell line, or *Xenopus* oocytes.

Another preferred aspect of the present invention relates to a substantially purified membrane preparation, partially purified membrane preparation, or cell lysate which has been obtained from a recombinant host cell transformed or transfected with a DNA expression vector which comprises and appropriately expresses a complete open reading frame as set forth in SEQ ID NOs: 1, 3, 5 and/or 7, resulting in a functional form of the respective RsGluCl1 or RsGluCl2 channel. The subcellular membrane fractions and/or membrane-containing cell lysates from the recombinant host cells (both prokaryotic and eukaryotic as well as both stably and transiently transformed or transfected cells) contain the functional proteins encoded by the nucleic acids of the present invention. This recombinant-based membrane preparation may comprise a *R. sanguineus* GluCl channel and is essentially free from contaminating proteins, including but not limited to other *R. sanguineus* source proteins or host proteins from a recombinant cell which expresses the T12 (SEQ ID NO:2), T82 (SEQ ID NO:4) T32 (SEQ ID NO:6) GluCl channel protein and/or the B1 (SEQ ID NO:8) GluCl2 channel protein. Therefore, a preferred aspect of the invention is a membrane preparation which contains a *R. sanguineus* GluCl channel comprising a GluCl protein comprising the functional form of the full length GluCl1 channel proteins as disclosed in FIG. 2 (SEQ ID NO:2; T12), FIG. 4 (SEQ ID NO:4; T82), and FIG. 6 (SEQ ID NO:6, T32) and or a functional form of the full length GluCl2 channel protein as disclosed in FIG. 8 (SEQ ID NO:8; B1). These subcellular membrane fractions will comprise either wild-type or mutant variations which are biologically functional forms of the *R. sanguineus* GluCl channels, any homomultimeric or heteromultimeric combination thereof (e.g., including but not The present invention also relates to biologically active fragments and/or mutants of a *R. sanguineus* GluCl1 channel protein, comprising the amino acid sequence as set forth in SEQ ID NOs:2, 4 and/or 6, as well as biologically active fragments and/or mutants of a *R. sanguineus* GluCl2 channel protein, comprising the amino acid sequence as set forth in SEQ ID NO:8, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for screening for selective modulators, including but not limited to agonists and/for antagonists for *R. sanguineus* GluCl1 channel pharmacology.

A preferred aspect of the present invention is disclosed in FIG. 2 (SEQ ID NO:2), FIG. 4 (SEQ ID NO:4), FIG. 6 (SEQ ID NO:6) and FIG. 8 (SEQ ID NO:8), respective amino acid sequences which comprise the *R. sanguineus* GluCl1 and GluCl2 proteins of the present invention, respectively. Characterization of one or more of these channel-proteins allows for screening methods to identify novel GluCl channel modulators that may have insecticidal, mitacidal and/or nematocidal activity for animal health or crop protection. As noted above, heterologous expression of a *Rhipicephalus sanguineus* GluCl channel will allow the pharmacological analysis of compounds active against parasitic invertebrate species relevant to animal and human health, especially dogs and cats, which are known to suffer from frequent tick infestations. Heterologous cell lines expressing a functional RsGluCl1 channel (e.g., functional forms of SEQ ID NOs:2, 4 and/or 6) or RsGluCl2 channel (e.g., a functional form of SEQ ID NO:8), can be used to establish functional or binding assays to identify novel GluCl channel modulators that may be useful in control of the aforementioned species groups.

The present invention also relates to polyclonal and monoclonal antibodies raised in response to the disclosed forms of RsGluCl1 and/or RsGluCl2, or a biologically active fragment thereof.

The present invention also relates to RsGluCl1 and/or RsGluCl2 fusion constructs, including but not limited to fusion constructs which express a portion of the RsGluCl linked to various markers, including but in no way limited to GFP (Green fluorescent protein), the MYC epitope, and GST.

Any such fusion constructs may be expressed in the cell line of interest and used to screen for modulators of one or more of the RsGluCl proteins disclosed herein.

The present invention relates to methods of expressing *R. sanguineus* GluCl1 and/or RsGluCl2 channel proteins and biological equivalents disclosed herein, assays employing these gene products, recombinant host cells which comprise DNA constructs which express these proteins, and compounds identified through these assays which act as agonists or antagonists of GluCl channel activity.

It is an object of the present invention to provide an isolated nucleic acid molecule (e.g., SEQ ID NOs:1, 3, 5, and 7) which encodes a novel form of *R. sanguneus* GluCl, or fragments, mutants or derivatives RsGluCl1 or RsGluCl2, these proteins as set forth in SEQ ID NOs:2, 4, 6 and 8, respectively. Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use and would be useful for screening for selective modulators for invertebrate GluCl pharmacology.

It is a further object of the present invention to provide the *R. sanguineus*GluCl proteins or protein fragments encoded by the nucleic acid molecules referred to in the preceding paragraph.

It is a further object of the present invention to provide recombinant vectors and recombinant host cells which comprise a nucleic acid sequence encoding *R. sanguineus* GluCl proteins or a biological equivalent thereof.

It is an object of the present invention to provide a substantially purified form of *R. sanguineus* GluCl1 or GluCl2 proteins, respectively, as set forth in SEQ ID NOs:2, 4, 6, and 8.

Is another object of the present invention to provide a substantially purified recombinant form of a *R. sanguineus* GluCl protein which has been obtained from a recombinant host cell transformed or transfected with a DNA expression vector which comprises and appropriately expresses a complete open reading frame as set forth in SEQ ID NOs: 1, 3, 5, and 7, resulting in a functional, processed form of the respective RsGluCl channel. It is especially preferred that the recombinant host cell be a eukaryotic host cell, such as a mammalian cell line.

It is an object of the present invention to provide for biologically active fragments and/or mutants of *R. sanguineus* GluCl1 or GluCl2 proteins, respectively, such as set forth in SEQ ID NOs:2, 4, 6, and 8, including but not necessarily limited to amino acid substitutions, deletions, additions, amino terminal truncations and carboxy-terminal truncations such that these mutations provide for proteins or protein fragments of diagnostic, therapeutic and/or prophylactic use.

It is further an object of the present invention to provide for substantially purified subcellular membrane preparation, partially purified membrane preparation or crude lysate from recombinant cells which comprise a pharmacologically active *R. sanguineus* GluCl1 or GluCl2-containing single, homomultimeric or hetermultimer channel, respectively, especially subcellular fractions obtained from a host cell transfected or transformed with a DNA vector comprising a nucleotide sequence which encodes a protein which comprises the amino acid as set forth in FIG. 2 (SEQ ID NO:2), FIG. 4 (SEQ ID NO:4), FIG. 6 (SEQ ID NO:6), and FIG. 8 (SEQ ID NO:8).

It is another object of the present invention to provide a substantially purified membrane preparation, partially purified membrane preparation, or crude lysate obtained from a recombinant host cell transformed or transfected with a DNA expression vector which comprises and appropriately expresses a complete open reading frame as set forth in SEQ ID NOs: 1, 3, 5, and/or 7, resulting in a functional, processed form of the respective RsGluCl channel. It is especially preferred is that the recombinant host cell be a eukaryotic host cell, including but not limited to a mammalian cell line, an insect cell line such as an S2 cell line, or *Xenopus* oocytes.

It is also an object of the present invention to use *R. sanguineus* GluCl proteins or membrane preparations containing *R. sanguineus* GluCl proteins or a biological equivalent to screen for modulators, preferably selective modulators, of *R. sanguineus* GluCl channel activity. Any such compound may be useful in screening for and selecting compounds active against parasitic invertebrate species relevant to animal and human health. Such species include but are not limited to worms, fleas, ticks, mites and lice. These membrane preparations may be generated from heterologous cell lines expressing these GluCls and may constitute full length protein, biologically active fragments of the full length protein or may rely on fusion proteins expressed from various fusion constructs which may be constructed with materials available in the art.

As used herein, "substantially free from other nucleic acids" means at least 90%, preferably 95%, more preferably 99%, and even more preferably 99.9%, free of other nucleic acids. As used interchangeably with the terms "substantially free from other nucleic acids" or "substantially purified" or "isolated nucleic acid" or "purified nucleic acid" also refer to a DNA molecules which comprises a coding region for a *R. sanguineus* GluCl protein that has been purified away from other cellular components. Thus, a *R. sanguineus* GluCl DNA preparation that is substantially free from other nucleic acids will contain, as a percent of its total nucleic acid, no more than 10%, preferably no more than 5%, more preferably no more than 1%, and even more preferably no more than 0.1%, of non-*R. sanguineus* GluCl nucleic acids. Whether a given *R. sanguineus* GluCl DNA preparation is substantially free from other nucleic acids can be determined by such conventional techniques of assessing nucleic acid purity as, e.g., agarose gel electrophoresis combined with appropriate staining methods, e.g., ethidium bromide staining, or by sequencing.

As used herein, "substantially free from other proteins" or "substantially purified" means at least 90%, preferably 95%, more preferably 99%, and even more preferably 99.9%, free of other proteins. Thus, a *R. sanguineus* GluCl protein preparation that is substantially free from other proteins will contain, as a percent of its total protein, no more than 10%, preferably no more than 5%, more preferably no more than 1%, and even more preferably no more than 0.1%, of non-*R. sanguineus* GluCl proteins. Whether a given *R. sanguineus* GluCl protein preparation is substantially free from other proteins can be determined by such conventional techniques of assessing protein purity as, e.g., sodium dodecyl sulfate polyacrylamide gel electrophoresis (SDS-PAGE) combined with appropriate detection methods, e.g., silver staining or immunoblotting. As used interchangeably with the terms "substantially free from other proteins" or "substantially purified", the terms "isolated *R. sanguineus* GluCl protein" or "purified *R. sanguineus* GluCl protein" also refer to *R. sanguineus* GluCl protein that has been isolated from a natural source. Use of the term "isolated" or "purified" indicates that *R. sanguineus* GluCl protein has been removed from its normal cellular environment. Thus, an isolated *R. sanguineus* GluCl protein may be in a cell-free solution or placed in a different cellular environment from that in which it occurs naturally. The term isolated does not imply that an isolated *R. sanguineus* GluCl protein is the only protein present, but instead means that an isolated *R. sanguineus* GluCl protein is substantially free of other proteins and non-amino acid material (e.g., nucleic acids, lipids, carbohydrates) naturally associated with the K sanguineus GluCl protein in vivo. Thus, a *R. sanguineus* GluCl protein that is recombinantly expressed in a prokaryotic or eukaryotic cell and substantially purified from this host cell which does not naturally (i.e., without intervention) express this GluCl protein is of course "isolated *R. sanguineus* GluCl protein" under any circumstances referred to herein. As noted above, a *R. sanguineus* GluCl protein preparation that is an isolated or purified *R. sanguineus* GluCl protein will be substantially free from other proteins will contain, as a percent of its total protein, no more than 10%, preferably no more than 5%, more preferably no more than 1%, and even more preferably no more than 0.1%, of non-*R. sanguineus* GluCl proteins.

As used interchangeably herein, "functional equivalent" or "biologically active equivalent" means a protein which does not have exactly the same amino acid sequence as naturally occurring *R. sanguineus* GluCl, due to alternative splicing, deletions, mutations, substitutions, or additions, but retains substantially the same biological activity as k sanguineus GluCl. Such functional equivalents will have significant amino acid sequence identity with naturally occurring *R. sanguineus* GluCl and genes and cDNA encoding such functional equivalents can be detected by reduced stringency hybridization with a DNA sequence encoding naturally occurring *R. sanguineus* GluCl. For example, a naturally occurring *R. sanguineus* GluCl1 protein disclosed herein comprises the amino acid sequence shown as SEQ ID NO:2 and is encoded by SEQ ID NO:1. A nucleic acid encoding a functional equivalent has at least about 50% identity at the nucleotide level to SEQ ID NO:1.

As used herein, "a conservative-amino acid substitution" refers to the replacement of one amino acid residue by another, chemically similar, amino-acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid).

As used herein, "LGIC" refers to a—ligand-gated ion channel—.

As used herein, "GluCl" refers to—L-glutamate gated chloride channel—.

As used herein, "RsGluCl" refers to—*Rhipicephalus sanguineus* L-glutamate gated chloride channel—.

Furthermore, as used herein "RsGluCl" may refer to RsGluCl1 and/or RsGluCl2.

As used herein, the term "mammalian" will refer to any mammal, including a human being.

BRIEF DESCRIPTION OF THE DRAWINGS

FIG. 1 shows the nucleotide sequence of the *R. sanguineus* GluCl1 cDNA clone, T12, set forth in SEQ ID NO:1.

FIG. 2 shows the amino acid sequence of the *R. sanguineus* GluCl1 protein, T12, as set forth in SEQ ID NO:2.

FIG. 3 shows the nucleotide sequence of the *R. sanguineus* GluCl1 cDNA clone, T82, as set forth in SEQ ID NO:3.

FIG. 4 shows the amino acid sequence of the *R. sanguineus* GluCl1 protein, T82, as set forth in SEQ ED NO:4.

FIG. 5 shows the nucleotide sequence of the *R. sanguineus* GluCl1 cDNA clone, T32, as set forth in SEQ ID NO:5.

FIG. 6 shows the amino acid sequence of the *R. sanguineus* GluCl1 protein, T32, as set forth in SEQ ID NO:6.

FIG. 7 shows the nucleotide sequence of the *R. sanguineus* GluCl2 cDNA clone, B1, as set forth in SEQ ID NO:7.

FIG. 8 shows the amino acid sequence of the *R. sanguineus* GluCl2 protein, B1, as set forth in SEQ ID NO:8.

FIG. 9 shows the amino acid sequence comparison for RsGluCl1 [T12 (SEQ ID NO:2), T82 (SEQ ID NO:4), T32 (SEQ ID NO:6) and RsGluCl2 (B1, SEQ ID NO:8) proteins.

DETAILED DESCRIPTION OF THE INVENTION

Figure 10:
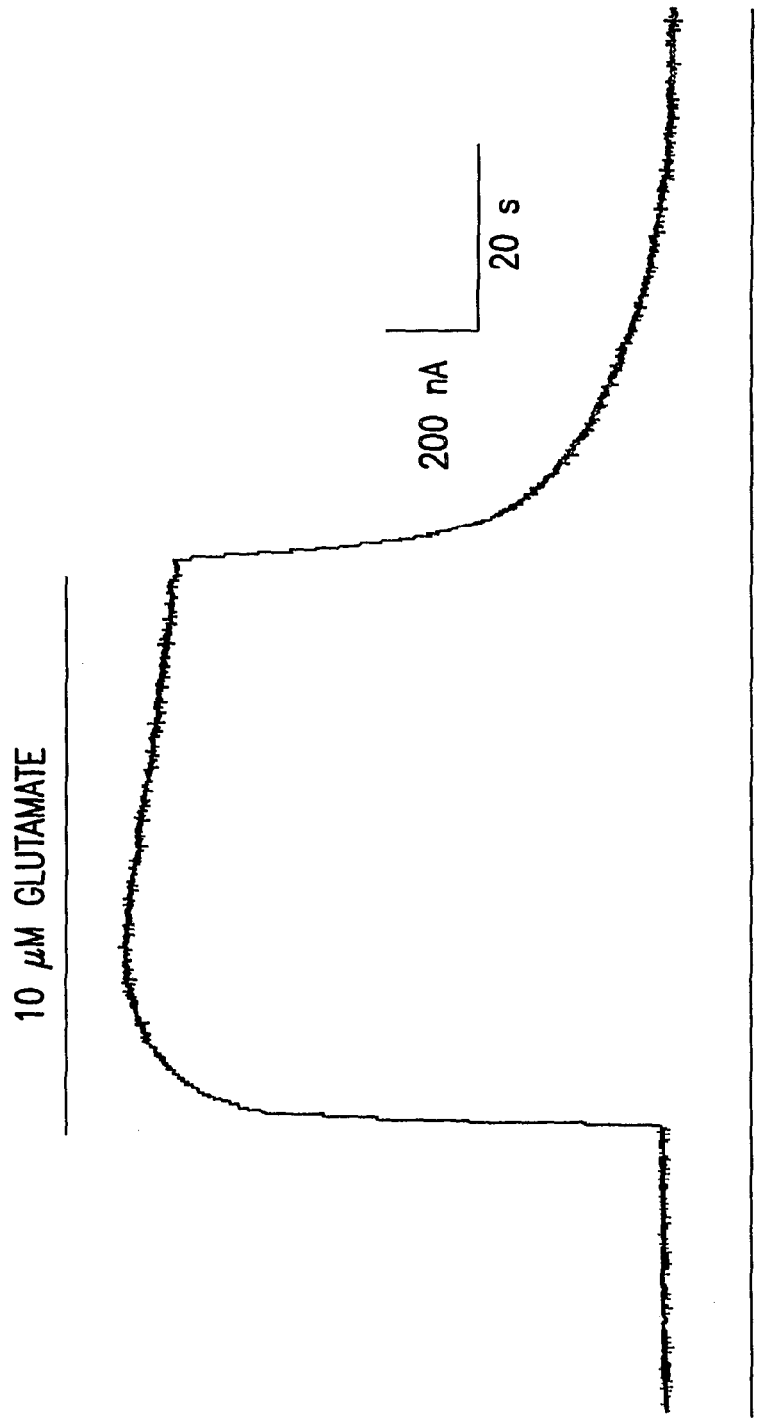
FIG. 10 shows the glutamate-activated current in *Xenopus* oocytes injected with RsGluCl1 T12 RNA. Current activation was maximal with ~10 μM glutamate and no current was seen in uninjected oocytes.

The present invention relates to an isolated nucleic acid molecule (polynucleotide) which encodes a *Rhipicephalus sanguineus* invertebrate GluCl channel protein. The isolated or purified nucleic acid molecules of the present invention are substantially free from other nucleic acids. For most cloning purposes, DNA is a preferred nucleic acid. As noted above, the DNA molecules disclosed herein may be transfected into a host cell of choice wherein the recombinant host cell provides a source for substantial levels of an expressed functional single, homomultimeric or heteromultimeric GluCl channel. Such functional ligand-gated ion channels may possibly respond to other known ligands which will in turn provide for additional screening targets to identify modulators of these channels, modulators which may act as effective insecticidal, mitacidal and/or nematocidal treatment for use in animal and human health and/or crop protection. It is shown herein that RsGluCl 1 exhibits a current in response to glutamate and that an RsGluCl2 channel protein expressed in *Xenopus* oocytes exhibit a current in response to the addition of ivermectin phosphate. However, it should be noted that a single channel subunit protein might not form a functional channel, such as seen with the GABA-A subunit gamma, which does not express a functional homomultimer. Therefore, the expressed proteins of the present invention may function in vivo as a component of a wild type ligand-gated ion channel which contains a number of accessory and/or channel proteins, including the channel proteins disclosed herein. However, the GluCl proteins of the present invention need not directly mimic the wild type channel in order to be useful to the skilled artisan. Instead, the ability to form a functional, single, membrane associated channel within a recombinant host cell renders these proteins amenable to the screening methodology known in the art and described in part within this specification. Therefore, as noted within this specification, the disclosed Rs channel proteins of the present invention are useful as single functional channels, as a homomultimeric channel or as a heteromultimeric channel with various proteins disclosed herein with or without additional Rs channel subunit proteins or accessory proteins which may contribute to the full, functional GluCl channel. As noted above, the DNA molecules disclosed herein may be transfected into a host cell of choice wherein the recombinant host cell provides a source for substantial levels of an expressed functional single, homomultimeric or heteromultimeric GluCl. Such functional ligand-gated ion channels may possibly respond to other known ligands which will in turn provide for additional screening targets to identify modulators of these channels, modulators which may act as effective insecticidal, mitacidal and/or nematocidal treatment for use in animal and human health and/or crop protection The present invention relates to an isolated nucleic acid molecule (polynucleotide) which encodes mRNA which expresses a novel *Rhipicephalus sanguineus* invertebrate GluCl1 channel protein, this DNA molecule comprising the nucleotide sequence disclosed herein as SEQ ID NO:1, SEQ ID NO:3 and SEQ ID NO:5.

The present invention relates to an isolated nucleic acid molecule polynucleotide) which encodes mRNA which expresses a novel *Rhipicephalus sanguineus* invertebrate GluCl2 channel protein, this DNA molecule comprising the nucleotide sequence disclosed herein as SEQ ID NO:7.

The isolation and characterization of the RsGluCl nucleic acid molecules of the present invention were identified as described in detail in Example Section 1. These cDNA molecules, as discussed herein, are especially useful to establish novel insecticide screens, validate potential lead compounds with insecticidal activity, especially for use in treating cattle, dog and cat tick and mite infestations or that may kill other arachnids, and use these novel cDNA sequences as hybridization probes to isolate related genes from other organisms to establish additional pesticide drug screens. The RsGluCl1 and RsGluCl2 encoding cDNAs of the present invention were isolated from the brown dog tick species *Rhipicephalus sanguineus*. The DNA sequence predicts proteins that share common features with the class of chloride channels sensitive to glutamate and ivermectin. When the RsGluCl1 or RsGluCl2 cDNAs are expressed in *Xenopus* oocytes, a glutamate and ivermectin-sensitive channel is observed. The pharmacology of compounds that act at these channels would likely be different between these species. By screening on the arachnid channel it will be more likely to discover arachnid-specific compounds. Therefore, the cDNAs of the present invention can be expressed in cell lines or other expression systems and used for competition binding experiments or for functional chloride channel assays to screen for compounds that activate, block or modulate the channel.

Invertebrate glutamate-gated chloride channels (GluCls) are related to the glycine- and GABA-gated chloride channels and are distinct from the excitatory glutamate receptors (e.g. NMDA or AMPA receptors). The first two members of the GluCl family were identified in the nematode *C. elegans*, following a functional screen for the receptor of the anthelmintic drug ivermectin. Several additional GluCls have now been cloned in other invertebrate species. However, there is no evidence yet for GluCl counterparts in vertebrates; because of this, GluCls are excellent targets for anthelmintics, insecticides, acaricides, etc. Specific GluCl modulators, such as nodulisporic acid and its derivatives have an ideal safety profile because they lack mechanism-based toxicity in vertebrates. The present invention relates in part to three novel *R. sanguineus* GluCl1 clones, T12, T82 and T32, and a *R. sanguineus* GluCl2 clone, B1. The RsGluCl1 cDNAs were isolated by low stringency hybridization using a *Drosophila* GluCl probe representing the putative membrane spanning domains, M1, M2 and M3. The RsGluCl2 cDNA was isolated by PCR using degenerate primers representing conserved regions in amino- and the M2-domains of the GluCl proteins of *Drosophila*, flea (*C. felis*), and *C. elegans*. It appears that RNA editing (A to G transitions) occur in these cDNAs and have resulted in some amino acid changes. RsGluCl1-T12 and T82 are similar except for one amino acid difference while RsGluCl1-T32 contains two additional exons in the coding region.

The present invention relates to the isolated or purified DNA molecule described in FIG. 1 (T12) and set forth as SEQ ID NO:1, which encodes the *R. sanguineus* GluCl1 protein described in FIG. 2 and set forth as SEQ ID NO:2, the nucleotide sequence of T12 is as follows:

(SEQ ID NO: 1)
```
   1  CGCTCCCCCA ATCCTGAGGT TCCTTCTAAC GAGAAGGAGG
      AGCCACAGCG CCGGCTGCGG

61  TACCGCCGCA CGGGCCAACG TGAGACCGCC CGAGCCCGGC
      GCCCTGACTT AGGCCGCTGA

121  GCGAAACCCA AGGCGGCGCG CTGGCCACTC CACGGGAACG
      AGACCGGCCC CCTGGAGACG

181  ACATCGTCGA CCACAATGAA CTACTTCTCT GACGTGGCGA
      AGATGGTGGC TTCATCGAAG

241  AGAGAAATCA TCGAAGCTTT CCACGCGACA TCTGGAGTAC
      ACGGCGCATG CGAATGAGCG

301  AACATCGCTG ACCGAGACTC GCCCGTCACC ATGAGCGTAC
      ATTCATGGCG CTTTTGTGTC

361  CCACTGGTGG CTCTAGCGTT TTTCTTGTTG ATTCTTCTGT
      CGTGTCCATC GGCATGGGGC

421  AAGGCAAATT TCCGCGCTAT AGAAAAGCGG ATATTGGACA
      CCATCATTGG CCAGGGTCGT

481  TATGACTGCA GGATCCGGCC CATGGGAATT AACAACACAG
      ACGGGCCGGC TCTTGTACGC

541  GTTAACATCT TTGTAAGAAG TATCGGCAGA ATTGATGACG
      TCACCATGGA GTACACAGTG

601  CAAATGACGT TCAGAGAGCA GTGGCGGGAC GAGAGACTCC
      AGTACGACGA CTTGGGCGGC

661  CAGGTTCGCT ACCTGACGCT CACCGAACCG GACAAGCTTT
      GGAAGCCGGA CCTGTTTTTC

721  TCCAACGAGA AAGAGGGACA CTTCCACAAC ATCATCATGC
      CCAACGTGCT TCTACGCATA

781  CATCCCAACG GCGACGTTCT CTTCAGCATC AGAATATCCT
      TGGTGCTTTC ATGTCCGATG

841  AACCTGAAAT TTTATCCTTT GGATAAACAA ATCTGCTCTA
      TCGTCATGGT GAGCTATGGG

901  TATACAACAG AGGACCTGGT GTTTCTATGG AAAGAGGGGG
      ATCCTGTACA GGTCACAAAA

961  AATCTCCACT TGCCACGTTT CACGCTGGAA AGGTTTCAAA
      CCGACTACTG CACCAGTCGG

1021  ACCAACACTG GCGAGTACAG CTGCTTGCGC GTGGACCTGG
      TGTTCAAGCG CGAGTTCAGC

1081  TACTACCTGA TCCAGATCTA CATCCCGTGC TGCATGCTGG
      TCATCGTGTC CTGGGTGTCG

1141  TTCTGGCTCG ACCCCACCTC GATCCCGGCG CGAGTGTCGC
      TGGGCGTCAC CACCCTGCTC

1201  ACCATGGCCA CGCAGATATC GGGCATCAAC GCCTCGCTGC
      CTCCCGTTTC CTACACCAAG

1261  GCCATTGACG TGTGGACCGG CGTCTGTCTG ACCTTCGTAT
      TCGGCGCGCT CCTCGAGTTC

1321  GCCCTGGTCA ACTACGCCTC GCGGTCAGAT TCACGCCGGC
      AGAACATGCA GAAGCAGAAG

1381  CAGAGGAAAT GGGAGCTCGA GCCGCCCCTG GACTCGGACC
      ACCTGGAGGA CGGCGCCACC

1441  ACGTTCGCCA TGAGGCCGCT GGTGCACCAC CACGGAGAGC
      TGCATGCCGA CAAGTTGCGG
```

-continued

```
1501  CAGTGCGAAG TCCACATGAA GACCCCCAAG ACGAACCTTT
      GCAAGGCCTG GCTTTCCAGG
1561  TTTCCCACGC GATCCAAACG CATCGACGTC GTCTCGCGGA
      TCTTCTTTCC GCTCATGTTC
1621  GCCCTCTTCA ACCTCGTCTA CTGGACAACC TACCTCTTCC
      GGGAAGACGA GGAAGACGAG
1681  TGACAGAACA CGGACGCCAC GACAGCCGCC ATCCGACACC
      ATCGTCACTG CAGGCACGCA
1741  CTCTGTCGCG CGCACACACC ACGAAGACCG GCGCGCCAAC
      GCACGATGCG CGTTGGCCGC
1801  TGAAAAACCC GGGAGCGGGG CGGTGGGGGA GGCTATGCCC
      CGGCCCCTCG CTCCTCATCC
1861  TCCGTGCACG CTCGAATCGT CATGCCCACA GCCAGAAAAA
      AAAAAGATAC CGTGCGAAAA
1921  GTGGCGGCAA CACAACGTCG ACGCCATCAG CGCCGCCCAG
      AGCTGCAAGC GGCTCCCACA
1981  TGGTTGCCAC CGCAGCTTCC TCTACGACCC TTCATCCCCA
      CCGGCACCAG CTACGAGAAA
2041  GGGACCTTAT TTCGGGCCAT CCCTACATAG GCGACTGTTG
      TTTTCGCACG AAAGATCTTT
2101  ACGCAGCTGA TGCTGAAAAA AAAAAAAAAA AAAAAAA.
```

The present invention also relates to the isolated or purified DNA molecule described in FIG. 3 (182) and set forth as SEQ ID NO:3, which encodes the R. sanguineus GluCl1 protein described in FIG. 4 and set forth as SEQ ID NO:4, the nucleotide sequence T82 as follows:

```
                                             (SEQ ID NO: 3)
   1  CACACCTCCT GCGTCTCTCC ACTCGATGAA GACCTGTCCC
      GGAGGCGCGA GCCCAACTGC
  61  GCGCTCTGTC CGCATGTGTC GCCGCCACTG AGAGGCCTCC
      GCCGTGGCGC GCTTGTCAAC
 121  GCGGCGCGCC GGCCCGCAGC AAATCGCGGG CATTCCACTC
      AGGGTCTCAT TCGCTCCCCC
 181  AATCCTGAGG TTCCTTCTAA CGAGAAGGAG GAGCCACAGC
      GCCGGCTGCG GTACCGCCGC
 241  ACGGGCCAAC GTGAGACCGC CCGAGCCCGG CGCCCTGACT
      TAGGCCGCTG AGCGAAACCC
 301  AAGGCGGCGC GCTGGCCACT CCACGGGAAC GAGACCGGCC
      CCCTGGAGAC GACATCGTCG
 361  ACCACAATGA ACTACTTCTC TGACGTGGCG AAGATGGTGG
      CTTCATCGAA GAGAGAAATC
 421  ATCGAAGCTT CCACGCGAC ATCTGGAGTA CACGGCGCAT
      GCGAATGAGC GAACATCGCT
 481  GACCGAGACT CGCCCGTCAC CATGAGCGTA CATTCATGGC
      GCTTTTGTGT CCCACTGGTG
 541  GCTCTAGCGT TTTTCTTGTT GATTCTTCTG TCGTGTCCAT
      CGGCATGGGG CAAGGCAAAT
 601  TTCCGCGCTA TAGAAAAGCG GATATTGGAC AGCATCATTG
      GCCAGGGTCG TTATGACTGC
 661  AGGATCCGGC CCATGGGAAT TAACAACACA GACCGGCCGG
      CTCTTGTACG CGTTAACATC
 721  TTTGTAAGAA GTATCGGCAG AATTGATGAC GTCACCATGG
      AGTACACAGT GCAAATGACG
 781  TTCAGAGAGC AGTGGCGGGA CGAGAGACTC CAGTACGACG
      ACTTGGGCGG CCAGGTTCGC
 841  TACCTGACGC TCACCGAACC GGACAAGCTT TGGAAGCCGG
      ACCTGTTTTT CTCCAACGAG
 901  AAAGAGGGAC ACTTCCACAA CATCATCATG CCCAACGTGC
      TTCTACGCAT ACATCCCAAC
 961  GGCGACGTTC TCTTCAGCAT CAGAATATCC TTGGTGCTTT
      CATGTCCGAT GAACCTGAAA
1021  TTTTATCCTT TGGATAAACA AATCTGCTCT ATCGTCATGG
      TGAGCTATGG GTATACAACA
1081  GAGGACCTGG TGTTTCTATG GAAAGAGGGG GATCCTGTAC
      AGGTCACAAA AAATCTCCAC
1141  TTGCCACGTT TCACGCTGGA AAGGTTTCAA ACCGACTACT
      GCACCAGTCG GACCAACACT
1201  GGCGAGTACA GCTGCTTGCG CGTGGACCTG GTGTTCAAGC
      GCGAGTTCAG CTACTACCTG
1261  ATCCAGATCT ACATCCCGTG CTGCATGCTG GTCATCGTGT
      CCTGGGTGTC GTTCTGGCTC
1321  GACCCCACCT CGATCCCGGC GCGAGTGTCG CTGGGCGTCA
      CCACCCTGCT CACCATGGCC
1381  ACGCAGATAT CGGGCATCAA CGCCTCGCTG CCTCCCGTTT
      CCTACACCAA GGCCATTGAC
1441  GTGTGGACCG GCGTCTGTCT GACCTTCGTA TTCGGCGCGC
      TCCTCGAGTT CGCCCTGGTC
1501  AACTACGCCT CGCGGTCAGA TTCACGCCGG CAGAACATGC
      AGAACCAGAA GCAGAGGAAA
1561  TGGGAGCTCG AGCCGCCCCT GGACTCGGAC CACCTGGAGG
      ACGCCGCCAC CACGTTCGCC
1621  ATGAGGCCGC TGGTGCACCA CCACGGAGAG CTGCATGCCG
      ACAAGTTGCG GCAGTGCGAA
1681  GTCCACATGA AGACCCCCAA GACGAACCTT TGCAAGGCCT
      GGCTTTCCAG GTTTCCCACG
1741  CGATCCAAAC GCATCGACGT CGTCTCGCGG ATCTTCTTTC
      CGCTCATGTT CGCCCTCTTC
1801  AACCTCGTCT ACTGGACAAC CTACCTCTTC GGGAAGACA
      AGGAAGACGA GTGACAGAAC
1861  ACGAACGCCA CGACAGCCGC CATCCGACAC CATCGTCACT
      GCAGGCACGC ACTCTGTCGC
1921  GCGCACACAC CACGAAGACC GGCGCGCCAA CGCACGATGC
      GCGTTGGCCG CTGAAAAACC
1981  CGGGAGCGGG GCGGTGGGGG AGGCTATGCC CCGGCCCCTC
      GCTCCTCATC CTCCGTGCAC
2041  GCTCGAATCG TCATCGCCAC AGCCAGAAAA AAAAAGATA
      CCGTGCGAAA AGTGGCGGCA
2101  ACACAACGTC GACGCCATCA GCGCCGCCCA GAGCTGCAAG
      CGGCTCCCAC ATGGTTGCCA
2161  CCGCAGCTTC CTCTACGACC CTTCATCCCC ACCGGCACCA
      GCTACGAGAA AGGGACCTTA
```

-continued

```
2221  TTTCGGGCCA TCCCTACATA GGCGACTGTT GTTTTCGCAC
      GAAAGATCTT TACGCAGCTG

2281  ATGCTGAAA.
```

The present invention also relates to the isolated or purified DNA molecule described in FIG. 5 (T32) and set forth as SEQ ID NO:5, which encodes the R. sanguineus GluCl protein described in FIG. 6 and set forth as SEQ ID NO:6, the nucleotide sequence T32 as follows:

```
                                        (SEQ ID NO: 5)
   1  CAGGCTCCGG CGTGACTGTC GCTCGCTCGG CTCTCGACGC
      TCGCGGCGGG AACAACCGCT

61  ACCCGGACGC TCGATCAGGA GCAGTTCGGG CCACAGAGAA
      AGGGGCCGAG GAGTGCACAC

121  CTCCTGCGTC TCTCCACTCG ATGAAGACCT GTCCCGGAGG
      CGCGAGCCCA ACTGCGCGCT

181  CTGTCCGCAT GTGTCGCCGC CACTGAGAGG CCTCCGGCGT
      GGCGCGCTTG TCAACGCGGC

241  GCGCCGGCCC GCAGCAAATC GCGGGCATTC CACTCAGGGT
      CTCATTCGCT CCCCCAATCC

301  TGAGGTTCCT TCTAACGAGA AGGAGGAGCC ACAGCGCCGG
      CTGCGGTACC GCCGCACGGG

361  CCAACGTGAG ACCGCCGAG CCCGGCGCCC TGACTTAGGC
      CGCTGAGCGA AACCCAAGGC

421  GGCGCGCTGG CCACTCCACG GGAACGAGAC CGGCCCCCTG
      GAGACGACAT CGTCGACCAC

481  AATGAACTAC TTCTCTGACG TGGCGAAGAT GGTGGCTTCA
      TCGAAGAGAG AAATCATCGA

541  AGCTTTCCAC GCGACATCTG GAGTACACGG CGCATGCGAA
      TGAGCGAACA TCGCTGACCG

601  AGACTCGCCC GTCACCATGA GCGTACATTC ATGGCGCTTT
      TGTGTCCCAC TGGTGGCTCT

661  AGCGTTTTTC TTGTTGATTC TTCTGTCGTG TCCATCGGCA
      TGGGCCGAAA CGCTGCCTAC

721  GCCACCAACC CGTGGCCAGG GGGGCGTTCC GGTCGCGGCC
      GCGATGCTCC TGGGGAAACA

781  GCAAAGTTCC CGCTACCAAG ATAAAGAGGG CAAGGCAAAT
      TTCCGCGCTA TAGAAAAGCG

841  GATATTGGAC AGCATCATTG GCCAGGGTCG TTATGACTGC
      AGGATCCGGC CCATGGGAAT

901  TAACAACACA GACGGGCCGG CTCTTGTACG CGTTAACATC
      TTTGTAAGAA GTATCGGCAG

961  AATTGATGAC GTCACCATGG AGTACACAGT GCAAATGACG
      TTCAGAGAGC AGTGGCGGGA

1021  CGAGAGACTC CAGTACGACG ACTTGGGCGG CCAGGTTCGC
      TACCTGACGC TCACCGAACC

1081  GGACAAGCTT TGGAAGCCGG ACCTGTTTTT CTCCAACGAG
      AAAGAGGGAC ACTTCCACAA

1141  CATCATCATG CCCAACGTGC TTCTACGCAT ACATCCCAAC
      GGCGACGTTC TCTTCAGCAT
```

```
1201  CAGAATATCC TTCGTGCTTT CATGTCCGAT GAACCTGAAA
      TTTTATCCTT TGGATAAACA

1251  AATCTGCTCT ATCGTCATGG TGAGCTATGG GTATACAACA
      GAGGACCTGG TGTTTCTATG

1321  GAAAGAGGGG GATCCTGTAC AGGTCACAAA AAATCTCCAC
      TTGCCACGTT TCACGCTGGA

1381  AAGGTTTCAA ACCGACTACT GCACCAGTCG GACCAACACT
      GGCGAGTACA GCTGCTTGCG

1441  CGTGGACCTG GTGTTCAAGC GCGAGTTCAG CTACTACCTG
      ATCCAGATCT ACATCCCGTG

1501  CTGCATGCTG GTCATCGTGT CCTGGGTGTC GTTCTGGCTC
      GACCCCACCT CGATCCCGGC

1561  GCGAGTGTCG CTGGGCGTCA CCACCCTGCT CACCATGGCC
      ACGCAGATAT CGGGCATCAA

1621  CGCCTCGCTG CCTCCCGTTT CCTACACCAA GGCCATTGAC
      GTGTGGACCG GCGTCTGTCT

1681  GACCTTCGTA TTCGGCGCGC TCCTCGAGTT CGCCCTGGTC
      AACTACGCCT CGCGGTCAGA

1741  TTCACGCCGG CAGAACATGC AGAAGCAGAA GCAGAGGAAA
      TGGGAGCTCG AGCCGCCCCT

1801  GGACTCGGAC CACCTGGAGG ACGGCGCCAC CACGTTCGCC
      ATGGTGAGCT CCGGCGAGCC

1861  GGCGGGCCTC ATGGCGCGAA CCTGGCCACC ACCGCCGCTG
      CCGCCAAACA TGGCGGCCGG

1921  CTCCGCGCAA GCCGGCGCCA GGCCGCTGGT GCACCACCAC
      GGAGAGCTGC ATGCCGACAA

1981  GTTGCGGCAG TGCGAAGTCC ACATGAAGAC CCCCAAGACG
      AACCTTTGCA AGGCCTGGCT

2041  TTCCAGGTTT CCCACGCGAT CCAAACGCAT CGACGTCGTC
      TCGCGGATCT TCTTTCCGCT

2101  CGTGTTCGCC CTCTTCAACC TCGTCTACTG GACAACCTAC
      CTCTTCCGGG AAGACGAGGA

2161  GGACGAGTGA CAGAACACGA ACGCCACGAC AGCCGCCATC
      CGACACCATC GTCACTGCAG

2221  GCACGCACTC TGTCGCGCGC ACACACCACG AAGACCGGCG
      CGCCAACGCA CGATGCGCGT

2281  TGGCCGCTGA AAAACCCGGG AGCGGGGCGG TGGGGAGGC
      TATGCCCCGG CCCCTCGCTC

2341  CTCATCCTCC GTGCACGCTC GAATCGTCAT CGCCACAGCC
      AGAAAAAAAA AAAAAAAAA.
```

The present invention also relates to an isolated or purified DNA molecule which encodes a R. sanguineus GluCl2 protein. One such nucleic acid is described in FIG. 7 (B1) and set forth as SEQ ID NO:7, which encodes the R. sanguineus GluCl2 protein described in FIG. 8 and set forth as SEQ ID NO:8, the nucleotide sequence B1 as follows:

```
                                        (SEQ ID NO: 7)
   1  CGCCGCTCAA TCGCGGGCTA CGGACTCGTC GTTCCCGGAG
      GGGCTTGGAC

51  CACAGCTCGC TCGTCACCGT GGTGGCTGGC CGCTTCGCCT
      GGCGGTCCTG

101  CACGCACGCT GTAACGAACG TCGCCACGCG ATGTTTGGTG
      TGCCATGCTC
```

-continued

```
 151   CCGCGCCTGC CGCCTTGTGG TGGTGATAGC TGCGTTCTGC
       TGGCCGCCCG

201   CTCTGCCGCT CGTACCCGGG GGAGTTTCCT CCAGAGCAAA
       CGATCTGGAC

251   ATTCTGGACG AGCTCCTCAA AAACTACGAT CGAAGGGCCC
       TGCCGAGCAG

301   TCACCTCGGA AATGCAACTA TTGTGTCATG CGAAATTTAC
       ATACGAAGTT

351   TTGGATCAAT AAATCCTTCG AACATGGACT ACGAAGTCGA
       CCTCTACTTC

401   CGGCAGTCGT GGCTCGACGA GCGGTTACGC AAATCCACGC
       TATCTCGTCC

451   GCTCGACCTT AATGACCCAA AGCTGGTACA AATGATATGG
       AAGCCAGAAG

501   TTTTCTTTGC GAACGCGAAA CACGCCGAGT TCCAATATGT
       GACTGTACCT

551   AACGTCCTCG TTAGGATCAA CCCGACTGGA ATAATCTTGT
       ACATGTTGCG

601   GTTAAAACTG AGGTTCTCCT GCATGATGGA CCTGTACCGG
       TACCCATGG

651   ATTCCCAAGT CTGCAGCATC GAAATTGCCT CTTTTTCCAA
       AACCACCGAA

701   GAGCTGCTGC TGAAATGGTC CGAGAGTCAG CCTGTCGTTC
       TCTTCGATAA

751   CCTCAAGTTG CCCCAGTTTG AAATAGAGAA GGTGAACACG
       TCCTTATGCA

801   AAGAAAAGTT TCACATAGGG GAATACAGTT GCCTGAAAGC
       CGACTTCTAT

851   CTGCAGCGTT CCCTCGGTTA TCACATGGTG CAGACCTATC
       TTCCGACCAC

901   GCTTATCGTG GTCATCTCAT GGGTGTCATT CTGGCTCGAC
       GTAGACGCCA

951   TACCCGCCCG TGTCACCCTG GGCGTAACCA CGCTGCTCAC
       CATCTCATCC

1001   AAGGGTGCCG GTATCCAGGG AAACCTGCCT CCCGTCTCGT
       ACATCAAGGC

1051   CATGGACGTC TGGATAGGAT CCTGTACTTC GTTTGTCTTT
       GCGGCCCTTC

1101   TAGAGTTCAC ATTCGTCAAC TATCTCTGGA GGCGGCTGCC
       CAATAAGCGC

1151   CCATCTTCTG ACGTACCGGT GACGGATATA CCAAGCGACG
       GCTCAAAGCA

1201   TGACATTGCG GCACAGCTCG TACTCGACAA GAATGGACAC
       ACCGAAGTTC

1251   GCACGTTGGT CCAAGCGATG CCACGCAGCG TCGGAAAAGT
       GAAGGCCAAG

1301   CAGATTGATC AACTCAGCCG AGTCGCCTTT CCCGCTCTTT
       TTCTCCTCTT
```

```
1351   CAACCTCGTG TACTGGCCGT ACTACATTAA GTCATAAAGA
       ACGTAGTTTT

1401   CT.
```

The above-exemplified isolated DNA molecules, shown in FIGS. 1, 3 5, and 7, respectively, comprise the following characteristics:

T12 (SEQ ID NO:1):
2138 nuc.:initiating Met (nuc. 331-333) and "TGA" term. codon (nuc.1681-1683), the open reading frame resulting in an expressed protein of 450 amino acids, as set forth in SEQ ID NO:2.

T82 (SEQ ID NO:3):
2289 nuc.:initiating Met (nuc. 502-504) and "TGA" term. codon (nuc. 1852-1854), the open reading frame resulting in an expressed protein of 450 amino acids, as set forth in SEQ ID NO:4.

T32 (SEQ ID NO:5):
2400 nuc.:initiating Met (nuc. 617-619) and "TGA" term. codon (nuc. 2168-2170), the open reading frame resulting in an expressed protein of 517 amino acids, as set forth in SEQ ID NO:6.

B1 (SEQ ID NO:7):
1402 nuc.:initiating Met (nuc. 131-133) and "TAA" term. codon (nuc. 1385-1387), the open reading frame resulting in an expressed protein of 418 amino acids, as set forth in SEQ ID NO:8.

The present invention also relates to biologically active fragments or mutants of SEQ ID NOs:1, 3, 5 and 7 which encodes mRNA expressing a novel *Rhipicephalus sanguineus* invertebrate GluCl1 or GluCl2 channel protein, respectively. Any such biologically active fragment and/or mutant will encode either a protein or protein fragment which at least substantially mimics the pharmacological properties of a *R. sanguineus* GluCl channel protein, including but not limited to the *R. sanguineus* GluCl1 channel proteins as set forth in SEQ ID NO:2, SEQ ID NO:4, and SEQ ID NO:6 as well as the respective GluCl2 channel protein as set forth in SEQ ID NO:8. Any such polynucleotide includes but is not necessarily limited to nucleotide substitutions, deletions, additions, amino-terminal truncations and carboxy-terminal truncations such that these mutations encode mRNA which express a functional *R. sanguineus* GluCl channel in a eukaryotic cell, such as *Xenopus* oocytes, so as to be useful for screening for agonists and/or antagonists of *R. sanguineus* GluCl activity.

A preferred aspect of this portion of the present invention is disclosed in FIG. 1 (SEQ ID NO:1; designated T12), FIG. 3 (SEQ ID NO:3; designated T82) and FIG. 5 (SEQ ID NO:5; designated T32) encoding novel *Rhipicephalus sanguineus* GluCl1 proteins, and FIG. 7 (SEQ ID NO:7, designated B1) encoding a novel *Rhipicephalus sanguineus* GluCl2 protein.

The isolated nucleic acid molecules of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

The degeneracy of the genetic code is such that, for all but two amino acids, more than a single codon encodes a particular amino acid. This allows for the construction of synthetic DNA that encodes the RsGluCl1 or RsGluCl2 protein where the nucleotide sequence of the synthetic DNA differs significantly from the nucleotide sequence of SEQ ID NOs:1, 3, 5, and 7 but still encodes the same RsGluCl protein as SEQ ID NO:1, 3, 5 and 7. Such synthetic DNAs are intended to be within the scope of the present invention. If it is desired to express such synthetic DNAs in a particular host cell or organism, the codon usage of such synthetic DNAs can be adjusted to reflect the codon usage of that particular host, thus leading to higher levels of expression of the RsGluCl channel protein in the host. In other words, this redundancy in the various codons which code for specific amino acids is within the scope of the present invention. Therefore, this invention is also directed to those DNA sequences which encode RNA comprising alternative codons which code for the eventual translation of the identical amino acid, as shown below:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asp=Asparagine: codons AAC, AAU
P=Pro=Proline: codons CCA, CCC, CCG, CCU
Q=Gln=Glutamne: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptaphan: codon UGG
Y=Tyr=Tyrosine: codons UAC, UAU Therefore, the present invention discloses codon redundancy which may result in differing DNA molecules expressing an identical protein. For purposes of this specification, a sequence bearing one or more replaced colons will be defined as a degenerate variation. Another source of sequence variation may occur through RNA editing, as discussed infra. Such RNA editing may result in another form of colon redundancy, wherein a change in the open reading frame does not result in an altered amino acid residue in the expressed protein. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally occurring peptide. Methods of altering the DNA sequences include but are not limited to site directed mutagenesis. Examples of altered properties include but are not limited to changes in the affinity of an enzyme for a substrate or a receptor for a ligand.

Included in the present invention are DNA sequences that hybridize to SEQ ID NOs:1, 3, 5 and 7 under stringent conditions. By way of example, and not limitation, a procedure using conditions of high stringency is as follows: Prehybridization of filters containing DNA is carried out for 2 hours to overnight at 65° C. in buffer composed of 6×SSC, 5× Denhardt's solution, and 100 μg/ml denatured salmon sperm DNA. Filters are hybridized for 12 to 48 hrs at 65° C. in prehybridization mixture containing 100 μg/ml denatured salmon sperm DNA and 5–20×$10^6$ cpm of $^{32}$P-labeled probe. Washing of filters is done at 37° C. for 1 hr in a solution containing 2×SSC, 0.1% SDS. This is followed by a wash in 0.1×SSC, 0.1% SDS at 50° C. for 45 min. before autoradiography. Other procedures using conditions of high stringency would include either a hybridization step carried out in 5×SSC, 5× Denhardt's solution, 50% formamide at 42° C. for 12 to 48 hours or a washing step carried out in 0.2×SSPE, 0.2% SDS at 65° C. for 30 to 60 minutes. Reagents mentioned in the foregoing procedures for carrying out high stringency hybridization are well known in the art. Details of the composition of these reagents can be found in, e.g., Sambrook et al., 1989, *Molecular Cloning: A Laboratory Manual*; Cold Spring Harbor Laboratory, Cold Spring Harbor, N.Y. In addition to the foregoing, other conditions of high stringency which may be used are well known in the art.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.,: (Computational Molecular Biology, Lesk, A. M., ed. Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds. Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exists a number of methods to measure identity between two polynucleotide or polypeptide sequences, the term "identity" is well known to skilled artisans (Carillo and Lipton, 1988, *SIAM J Applied Math* 48:1073). Methods commonly employed to determine identity or similarity between two sequences include, but are not limited to, those disclosed in Guide to Huge Computers, Martin J. Bishop, ed., Academic Press, San Diego, 1994, and Carillo and Lipton, 1988, *SLAM J Applied Math* 48:1073. Methods to determine identity and similarity are codified in computer programs. Preferred computer program methods to determine identity and similarity between two sequences include, but are not limited to, GCG program package (Devereux, et al, 1984, *Nucleic Acids Research* 12(1):387), BLASTN, and FASTA (Altschul, et al., 1990, *J. Mol. Biol.* 215:403).

As an illustration, by a polynucleotide having a nucleotide sequence having at least, for example, 95% "identity" to a reference nucleotide sequence of SEQ ID NO:1 is intended that the nucleotide sequence of the polynucleotide is identical to the reference sequence except that the polynucleotide sequence may include up to five point mutations or alternative nucleotides per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations or alternative nucleotide substitutions of the reference sequence may occur at the 5' or 3' terminal positions of the reference nucleotide sequence or anywhere between those terminal positions, interspersed either individually among nucleotides in the reference sequence or in one or more contiguous groups within the reference sequence. One source of such a "mutation" or change which results in a less than 100% identity may occur through RNA editing. The process of RNA editing results in modification of an mRNA molecule such that use of that modified mRNA as a template to generate a cloned cDNA may result in one or more nucleotide changes, which may or may not result in a codon change. This RNA editing is known to be catalyzed by an RNA editase. Such an RNA editase is RNA adenosine deaminase, which converts an adenosine residue to an inosine residue, which tends to mimic a cytosine residue. To this end, conversion of an mRNA residue from A to I will result in A to G transitions in the coding and noncoding regions of a cloned cDNA (e.g., see Hanrahan et al, 1999, *Annals New York Acad. Sci.* 868:51-66; for a review see Bass, 1997, *TIBS* 22: 157-162). Similarly, by a polypeptide having an amino acid sequence having at least, for example, 95% identity to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO:2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence of anywhere between those terminal positions, interspersed either individually among residues in the reference sequence or in one or more contiguous, groups within the reference sequence. Again, as noted above, RNA editing may result in a codon change which will result in an expressed protein which differs in "identity" from other proteins expressed from "non-RNA edited" transcripts, which correspond directly to the open reading frame of the genomic sequence. The open reading frame of the T12 and T82 clones are identical, save for a single nucleotide change which results in a single amino acid change (T12—"gag"/Glu v. T82—"aag"/Lys at amino acid residue 447 of SEQ ID NOs: 2 and 4). The T12/T82 clone shows about a 57% identity with the B1 clone at the nucleotide level whereas the T32 clone shows about a 57% identity with the B1 clone at the nucleotide level.

The present invention also relates to recombinant vectors and recombinant hosts, both prokaryotic and eukaryotic, which contain the substantially purified nucleic acid molecules disclosed throughout this specification. The nucleic acid molecules of the present invention encoding a RsGluCl channel protein, in whole or in part, can be linked with other DNA molecules, i.e, DNA molecules to which the RsGluCl coding sequence are not naturally linked, to form "recombinant DNA molecules" which encode a respective RsGluCl channel protein. The novel DNA sequences of the present invention can be inserted into vectors which comprise nucleic acids encoding RsGluCl or a functional equivalent. These vectors may be comprised of DNA or RNA; for most cloning purposes DNA vectors are preferred. Typical vectors include plasmids, modified viruses, bacteriophage, cosmids, yeast artificial chromosomes, and other forms of episomal or integrated DNA that can encode a RsGluCl channel protein. It is well within the purview of the skilled artisan to determine an appropriate vector for a particular gene transfer or other use.

The present invention also relates to a substantially purified form of a respective RsGluCl channel protein, which comprise the amino acid sequence disclosed in FIG. 2, FIG. 4, FIG. 6 and FIG. 8, and as set forth in SEQ ID NOs:2, 4, 6, and 8, respectively. The disclosed RsGluCl proteins contain an open reading frame of 450 amino acids (T12 and T82, SEQ ID NOs: 2 and 4, respectively), 517 amino acids (T32, SEQ ID NO: 6) and 418 amino acids (SEQ ID NO:8) in length, as shown in FIGS. 2, 4, 6, and 8, and as follows:

```
T12:
                                          (SEQ ID NO: 2)
NSVHSWRFCV PLVALAFFLL ILLSCPSAWG KANFRAIEKR

ILDSIIGQGR YDCRIRPMGI NNTDGPALVR VNIFVRSIGR

IDDVTMEYTV QMTFREQWRD ERLQYDDLGG QVRYLTLTEP

DKLWKPDLFF SNEKEGHFHN IIMPNVLLRI HPNGDVLFSI

RISLVLSCPM NLKFYPLDKQ ICSIVMVSYG YTTEDLVFLW

KEGDPVQVTK NLHLPRFTLE EFQTDYCTSR TNTGEYSCLR

VDLVFKREFS YYLIQIYIPC CMLVIVSWVS FWLDPTSIPA

RVSLGVTTLL TMATQISGIN ASLPPVSYTK AIDVWTGVCL

TFVFGALLEF ALVNYASRSD SRRQNMQKQK QRKWELEPPL

DSDHLEDGAT TFAMRPLVHH HGELHADKLR QCEVHMKTPK

TNLCKAWLSR FPTRSKRIDV VSRIFFPLMF ALFNLVYWTT

YLFREDEEDE*;

T82:
                                          (SEQ ID NO: 4)
MSVHSWRFCV PLVALAFFLL ILLSCPSAWG KANFRAIEKR

ILDSIIGQGR YDCRIRPMGI NNTDGPALVR VNIFVRSIGR

IDDVTMEYTV QMTFREQWRD EELQYDDLGG QVRYLTLTEP

DKLWKPDLFF SNEKEGHFHN IIMPNVLLRI HPNGDVLFSI

RISLVLSCPM NLKFYPLDKQ ICSIVMVSYG YTTEDLVFLW

KEGDPVQVTK NLHLPRFTLE RFQTDYCTSR TNTGEYSCLR

VDLVFKREFS YYLIQIYIPC CMLVIVSWVS FWLDPTSIPA

RVSLGVTTLL TMATQISGIN ASLPPVSYTK AIDVWTGVCL

TFVFGALLEF ALVNYASRSD SRRQNMQKQK QRKWELEPPL

DSDHLEDGAT TFANRPLVHH HGELHADKLR QCEVHMKTPK

TNLCKAWLSR FPTRSKRIDV VSRIFFPLMF ALFNLVYWTT

YLFREDKEDE*;

T32:
                                          (SEQ ID NO: 6)
MSVHSWRFCV PLVALAFFLL ILLSCPSAWA ETLPTPPTRG

QGGVPVAAAM LLGKQQSSRY QDKEGKANFR AIEKRILDSI

IGQGRYDCRI RPMGINNTDG PALVRVNIFV RSIGRIDDVT

MEYTVQMTFR EQWRDERLQY DDLGGQVRYL TLTEPDKLWK

PDLFFSNEKE GHFHNIIMPN VLLRIHPNGD VLFSIRISLV

LSCPMNLKFY PLDKQICSIV MVSYGYTTED LVFLWKEGDP
```

```
                      -continued
VQVTKNLHLP RFTLERFQTD YCTSRTNTGE YSCLRVDLVF

KREFSYYLIQ IYIPCCMLVI VSWVSFWLDP TSIPARVSLG

VTTLLTMATQ ISGINASLPP VSYTKAIDVW TGVCLTFVFG

ALLEFALVNY ASRSDSRRQN MQKQKQRKWE LEPPLDSDHL

EDGATTFAMV SSGEPAGLMA RTWPPPPLPP NMAAGSAQAG

ARPLVHHHGE LHADKLRQCE VHMKTPKTNL CKAWLSRFPT

RSKRIDVVSR IFFPLVFALF NLVYWTTYLF REDEEDE*;
and,

B1:
                                          (SEQ ID NO: 8)
MFGVPCSRAC RLVVVIAAFC WPPALPLVPG GVSSRANDLD

ILDELLKNYD RRALPSSHLG NATIVSCEIY IRSFGSINPS

NMDYEVDLYF RQSWLDEELR KSTLSRPLDL NDPKLVQMIW

KPEVFFANAK HAEFQYVTVP NVLVRINPTG IILYMLRLKL

RFSCMMDLYR YPMDSQVCSI EIASFSKTTE ELLLKWSESQ

PVVLFDNLKL PQFEIEKVNT SLCKEKFHIG EYSCLKADFY

LQRSLGYHMV QTYLPTTLIV VISWVSFWLD VDAIPARVTL

GVTTLLTISS KGAGIQGNLP PVSYIKAMDV WIGSCTSFVF

AALLEFTFVN YLWRRLPNKR PSSDVPVTDI PSDGSKHDIA

AQLVLDKNGH TEVRTLVQAM PRSVGKVKAK QIDQLSRVAF

PALFLLFNLV YWPYYIKS.
```

The open reading frames of the T12 and T82 clones are identical, save for a single nucleotide change which results in a single amino acid change at residue 447 of SEQ ID NOs: 2 and 4. The T32 open-reading frame contains two addition exons when compared to the T12/T82 reading frame, which result in a 35 amino acid insertion in the amino terminal region of the T32 protein (amino acid residue 30-64 of SEQ ID NO:6) and another 32 amino acid insertion within the COOH-terminal region (amino acid residue 410-441). The T12/T82 clones show about a 57% identity with the B1 clone at the nucleotide level whereas the T32 clone shows about a 57% identity with the B1 clone at the nucleotide level.

The present invention also relates to biologically active fragments and/or mutants of the RsGluCl1 and RsGluCl2 proteins comprising the amino acid sequence as set forth in SEQ D NOs:2, 4, 6, and 8, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for screening for agonists and/or antagonists of RsGluCl function.

To this end, a preferred aspect of the present invention is a functional RsGluCl channel receptor, comprised of either a single channel protein or a channel comprising multiple subunits, referred to herein as a homomultimeric channel or a heteromultimeric channel. Therefore, a single channel may be comprised of a protein as disclosed in SEQ ID NOs: 2, 4, 6 or 8, or a biologically active equivalent thereof (i.e., an altered channel protein which still functions in a similar fashion to that of a wild-type channel receptor). A homomultimeric channel receptor complex will comprise more than one polypeptide selected from the disclosed group of SEQ ED NOs: 2, 4, 6 and 8, as well as biologically active equivalents.

A heteromultimeric channel receptor complex will comprise multiple subunits wherein at least 2 of the 3 proteins disclosed herein contribute to channel formation, or where at least one of the proteins associates with additional proteins or channel components to provide for an active channel receptor complex. Therefore, the present invention additionally relates to substantially purified channels as described herein, as well as substantially purified membrane preparations, partially purified membrane preparations, or cell lysates which contain the functional single, homomultimeric or heteromultimeric channels described herein. These substantially purified, fully processed GluCl channel proteins may be obtained from a recombinant host cell containing a DNA expression vector comprises a nucleotide sequence as set forth in SEQ ID NOs: 1, 3, 5, and/or 7, and expresses the respective RsGluCl precursor protein. It is especially preferred is that the recombinant host cell be a eukaryotic host cell, including but not limited to a mammalian cell line, an insect cell line such as an S2 cell line, or *Xenopus* oocytes, as noted above.

As with many proteins, it is possible to modify many of the amino acids of RsGluCl channel protein and still retain substantially the same biological activity as the wild type protein. Thus this invention includes modified RsGluCl polypeptides which have amino acid deletions, additions, or substitutions but that still retain substantially the same biological activity as a respective, corresponding RsGluCl. It is generally accepted that single amino acid substitutions do not usually alter the biological activity of a protein (see, e.g., *Molecular Biology of the Gene*, Watson et al., 1987, Fourth Ed., The Benjamin/Cummings Publishing Co., Inc., page 226; and Cunningham & Wells, 1989, *Science* 244:1081-1085). Accordingly, the present invention includes polypeptides where one amino acid substitution has been made in SEQ ID NO:2, 4, 6, and/or 8, wherein the polypeptides still retain substantially the same biological activity as a corresponding RsGluCl protein. The present invention also includes polypeptides where two or more amino acid substitutions have been made in SEQ ID NO:2, 4, 6, or 8, wherein the polypeptides still retain substantially the same biological activity as a corresponding RsGluCl protein. In particular, the present invention includes embodiments where the above-described substitutions are conservative substitutions.

One skilled in the art would also recognize that polypeptides that are functional equivalents of RsGluCl and have changes from the RsGluCl amino acid sequence that are small deletions or insertions of amino acids could also be produced by following the same guidelines, (i.e, minimizing the differences in amino acid sequence between RsGluCl and related proteins. Small deletions or insertions are generally in the range of about 1 to 5 amino acids. The effect of such small deletions or insertions on the biological activity of the modified RsGluCl polypeptide can easily be assayed by producing the polypeptide synthetically or by making the required changes in DNA encoding RsGluCl and then expressing the DNA recombinantly and assaying the protein produced by such recombinant expression.

The present invention also includes truncated forms of RsGluCl which contain the region comprising the active site of the enzyme. Such truncated proteins are useful in various assays described herein, for crystallization studies, and for structure-activity-relationship studies.

The present invention also relates to membrane-containing crude lysates or substantially purified subcellular membrane fractions from the recombinant host cells (both prokaryotic and eukaryotic as well as both stably and transiently transformed or transfected cells) which contain the nucleic acid molecules of the present invention. These recombinant host cells express RsGluCl or a functional equivalent, which becomes post translationally associated with the cell membrane in a biologically active fashion. These subcellular membrane fractions will comprise either wild-type or mutant forms of RsGluCl at levels substantially above endogenous levels and hence will be useful in assays to select modulators of RsGluCl proteins or channels. In other words, a specific use for such subcellular membranes involves expression of RsGluCl within the recombinant cell followed by isolation and substantial purification of the membranes away from other cellular components and subsequent use in assays to select for modulators, such as agonist or antagonists of the protein or biologically active channel comprising one or more of the proteins disclosed herein. Alternatively, the lysed cells, containing the membranes, may be used directly in assays to select for modulators of the recombinantly expressed protein(s) disclosed herein. Therefore, another preferred aspect of the present invention relates to a substantially purified membrane preparation or lysed recombinant cell components which include membranes, which has been obtained from a recombinant host cell transformed or transfected with a DNA expression vector which comprises and appropriately expresses a complete open reading frame as set forth in SEQ ID NOs: 1, 3, 5, and/or 7, resulting in a functional form of the respective RsGluCl channel. It is especially preferred is that the recombinant host cell be a eukaryotic host cell, including but not limited to a mammalian cell line, an insect cell line such as an S2 cell line.

The present invention also relates to isolated nucleic acid molecules which are fusion constructions expressing fusion proteins useful in assays to identify compounds which modulate wild-type RsGluCl activity, as well as generating antibodies against RsGluCl. One aspect of this portion of the invention includes, but is not limited to, glutathione S-transferase (GST)-RsGluCl fusion constructs. Recombinant GST-RsGluCl fusion proteins may be expressed in various expression systems, including *Spodoptera frugiperda* (Sf21) insect cells (Invitrogen) using a baculovirus expression vector (pAcG2T, Pharmingen). Another aspect involves RsGluCl fusion constructs linked to various markers, including but not limited to GFP (Green fluorescent protein), the MYC epitope, and GST. Again, any such fusion constructs may be expressed in the cell line of interest and used to screen for modulators of one or more of the RsGluCl proteins disclosed herein.

A preferred aspect for screening for modulators of RsGluCl channel activity is an expression system for the electrophysiological-based assays for measuring glutamate-gated chloride channel activity comprising injecting the DNA molecules of the present invention into *Xenopus laevis* oocytes. The general use of *Xenopus* oocytes in the study of ion channel activity is known in the art (Dascal, 1987, *Cit. Rev. Biochem.* 22: 317-317; Lester, 1988, *Science* 241: 1057-1063; see also *Methods of Enzymology*, Vol. 207, 1992, Ch. 14-25, Rudy and Iverson, ed., Academic Press, Inc., New York). An improved method exists for measuring channel activity and modulation by agonists and/or antagonists which is several-fold more sensitive than previous techniques. The *Xenopus* oocytes are injected with nucleic acid material, including but not limited to DNA, mRNA or cRNA which encode a gated-channel, wherein channel activity may be measured as well as response of the channel to various modulators. Ion channel activity is measured by utilizing a holding potential more positive than the reversal potential for chloride (i.e, greater than −30 mV), preferably about 0 mV. This alteration in assay measurement conditions results in a 10-fold increase in sensitivity of the assay to modulation by ivermectin phosphate. Therefore, this improved assay allows screening and selecting for compounds which modulate GluCl activity at levels which were previously thought to be undetectable.

Any of a variety of procedures may be used to clone RsGluCl. These methods include, but are not limited to, (1) a RACE PCR cloning technique (Frohman, et al., 1988, *Proc. Natl. Acad. Sci. USA* 85: 8998-9002). 5' and/or 3' RACE may be performed to generate a full-length cDNA sequence. This strategy involves using gene-specific oligonucleotide primers for PCR amplification of RsGluCl cDNA. These gene-specific primers are designed through identification of an expressed sequence tag (EST) nucleotide sequence which has been identified by searching any number of publicly available nucleic acid and protein databases; (2) direct functional expression of the RsGluCl cDNA following the construction of a RsGluCl-containing cDNA library in an appropriate expression vector system; (3) screening a RsGluCl-containing cDNA library constructed in a bacteriophage or plasmid shuttle vector with a labeled degenerate oligonucleotide probe designed from the amino acid sequence of the RsGluCl protein; (4) screening a RsGluCl-containing cDNA library constructed in a bacteriophage or plasmid shuttle vector with a partial cDNA encoding the RsGluCl protein. This partial cDNA is obtained by the specific PCR amplification of RsGluCl DNA fragments through the design of degenerate oligonucleotide primers from the amino acid sequence known for other GluCl channels which are related to the RsGluCl protein; (5) screening a RsGluCl-containing cDNA library constructed in a bacteriophage or plasmid shuttle vector with a partial cDNA or oligonucleotide with homology to a RsGluCl protein. This strategy may also involve using gene-specific oligonucleotide primers for PCR amplification of RsGluCl cDNA identified as an EST as described above; or (6) designing 5' and 3' gene specific oligonucleotides using SEQ ID NO: 1, 3, and 5 as a template so that either the full-length cDNA may be generated by known RACE techniques, or a portion of the coding region may be generated by these same known RACE techniques to generate and isolate a portion of the coding region to use as a probe to screen one of numerous types of cDNA and/for genomic libraries in order to isolate a full-length version of the nucleotide sequence encoding RsGluCl. Alternatively, the RsGluCl1 and RsGluCl2 cDNAs of the present invention may be cloned as described in Example Section 1. For RsGluCl1 cDNA clones, adult brown dog tick polyA$^{30}$ RNA was isolated using the Poly(A)Pure™ mRNA Isolation Kit (Ambion). Tick cDNA was synthesized using oligo-dT primers and the ZAP cDNA® Synthesis Kit (Stratagene), and cDNA >1 kb was selected using cDNA Size Fractionation Columns (BRL). A tick cDNA library was constructed in the Lambda ZAP® II vector using the GIGAPACK® III Gold Cloning Kit (Stratagene). A *Drosophila* GluCl cDNA fragment spanning the M1 to M3 region was used in a low-stringency screen of the tick cDNA library. Filters were exposed for eleven days and six positives were isolated for sequence analysis. Three of the clones (T12, T82 and T32) encode GluCl-related proteins and were sequenced on both ends. For isolation of the RsGluCl2 cDNAs, most molecular procedures were again performed following standard procedures available in references such as Ausubel et. al. (1992. Short protocols in molecular biology. F. M. Ausubel et al.,—$2^{nd}$. ed. (John Wiley & Sons), and Sambrook et al., (1989. Molecular cloning. A laboratory manual. J. Sambrook, E. F. Fritsch, and T. Maniatis—2 ed. (Cold Spring Harbor Laboratory Press). Poly (A)+ RNA was isolated from Tick heads. First strand cDNA was synthesized from 50 ng RNA using a SUPERSCRIPT preamplification System (Life Technologies). A tenth of the first strand reaction was used for PCR. The degenerate oligos utilized were designed based on sequences obtained from *C elegans, Drosophila*, and Flea (*C. felis*) GluCls: Two PCR rounds, using the combinations "27F2+3AF1, then 27F2+3BF2" were performed. One tenth of the PCR reaction products was tested by Southern blot analysis, in order to identify and prevent the PCR-cloning of contaminating sequences. Novel PCR products of the appropriate size were cloned into the pCR2.1 plasmid vector using a "TA" cloning kit (Invitrogen, Inc.). Following sequence analysis (ABI Prism, PE Applied Biosystems), selected PCR clone inserts were radiolabelled and used as probes to screen a cDNA library generated into the Uni-ZAP® vector (Stratagene, Inc.) from using the RNA preparation mentioned above. Sequences from full-length cDNA clones were analysed using the GCG Inc. package. Subcloning of RsGluCl2 into a mammalian expression vector was done by excision of an 1.85 kb coding-region-containing fragment (XhoI-EcoRI digest) from the original insert of clone RsGluCl2 B1 from the UniZap® pBS plasmid, followed by ligation into the TetSplice® vector (Life Technologies Inc.).

It is readily apparent to those skilled in the art that other types of libraries, as well as libraries constructed from other cell types or species types, may be useful for isolating a RsGluCl-encoding DNA or a RsGluCl homologue. Other types of libraries include, but are not limited to, cDNA libraries derived from other brown dog tick cell types.

It is readily apparent to those skilled in the art that suitable cDNA libraries may be prepared from cells or cell lines which have RsGluCl activity. The selection of cells or cell lines for use in preparing a cDNA library to isolate a cDNA encoding RsGluCl may be done by first measuring cell-associated RsGluCl activity using any known assay available for such a purpose.

Preparation of cDNA Libraries can be Performed by Standard Techniques Well known in the art. Well known cDNA library construction techniques can be found for example, in Sambrook et al., 1989, *Molecular Cloning: A Laboratory Manual*; Cold Spring Harbor Laboratory, Cold Spring Harbor, N.Y. Complementary DNA libraries may also be obtained from numerous commercial sources, including but not limited to Clontech Laboratories, Inc. and Stratagene.

It is also readily apparent to those skilled in the art that DNA encoding RsGluCl may also be isolated from a suitable genomic DNA library. Construction of genomic DNA libraries can be performed by standard techniques well known in the art. Well known genomic DNA library construction techniques can be found in Sambrook, et al., supra. One may prepare genomic libraries, especially in P1 artificial chromosome vectors, from which genomic clones containing the RsGluCl can be isolated, using probes based upon the RsGluCl nucleotide sequences disclosed herein. Methods of preparing such libraries are known in the art (Ioannou et al., 1994, *Nature Genet.* 6:84-89).

In order to clone a RsGluCl gene by one of the preferred methods, the amino acid sequence or DNA sequence of a RsGluCl or a homologous protein may be necessary. To accomplish this, a respective RsGluCl channel protein may be purified and the partial amino acid sequence determined by automated sequenators. It is not necessary to determine the entire amino acid sequence, but the linear sequence of two regions of 6 to 8 amino acids can be determined for the PCR amplification of a partial RsGluCl DNA fragment. Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the RsGluCl sequence but others in the set will be capable of hybridizing to RsGluCl DNA even in the presence of DNA oligonucleotides with mismatches. The mismatched DNA oligonucleotides may still sufficiently hybridize to the RsGluCl DNA to permit identification and isolation of RsGluCl encoding DNA. Alternatively, the nucleotide sequence of a region of an expressed sequence may be identified by searching one or more available genomic databases. Gene-specific primers may be used to perform PCR amplification of a cDNA of interest from either a cDNA library or a population of cDNAs. As noted above, the appropriate nucleotide sequence for use in a PCR-based method may be obtained from SEQ ID NO: 1, 3, 5, or 7 either for the purpose of isolating overlapping 5' and 3'RACE products for generation of a full-length sequence coding for RsGluCl, or to isolate a portion of the nucleotide sequence coding for RsGluCl for use as a probe to screen one or more cDNA- or genomic-based libraries to isolate a full-length sequence encoding RsGluCl or RsGluCl-like proteins.

This invention also includes vectors containing a RsGluCl gene, host cells containing the vectors, and methods of making substantially pure RsGluCl protein comprising the steps of introducing the RsGluCl gene into a host cell, and cultivating the host cell under appropriate conditions such that RsGluCl is produced. The RsGluCl so produced may be harvested from the host cells in conventional ways. Therefore, the present invention also relates to methods of expressing the RsGluCl protein and biological equivalents disclosed herein, assays employing these gene products, recombinant host cells which comprise DNA constructs which express these proteins, and compounds identified through these assays which act as agonists or antagonists of RsGluCl activity.

The cloned RsGluCl cDNA obtained through the methods described above may be recombinantly expressed by molecular cloning into an expression vector (such as pcDNA3.neo, pcDNA3.1, pCR2.1, pBlueBacHis2 or pLITMUS28, as well as other examples, listed infra) containing a suitable promoter and other appropriate transcription regulatory elements, and transferred into prokaryotic or eukaryotic host cells to produce recombinant RsGluCl. Expression vectors are defined herein as DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. To determine the RsGluCl cDNA sequence(s) that yields optimal levels of RsGluCl, cDNA molecules including but not limited to the following can be constructed: a cDNA fragment containing the full-length open reading frame for RsGluCl as well as various constructs containing portions of the cDNA encoding only specific domains of the protein or rearranged domains of the protein. All constructs can be designed to contain none, all or portions of the 5' and/or 3' untranslated region of a RsGluCl cDNA.

The expression levels and activity of RsGluCl can be determined following the introduction, both singly and in combination, of these constructs into appropriate host cells. Following determination of the RsGluCl cDNA cassette yielding optimal expression in transient assays, this RsGluCl cDNA construct is transferred to a variety of expression vectors (including recombinant viruses), including but not limited to those for mammalian cells, plant cells, insect cells, oocytes, bacteria, and yeast cells. Techniques for such manipulations can be found described in Sambrook, et al., supra, are well known and available to the artisan of ordinary skill in the art. Therefore, another aspect of the present invention includes host cells that have been engineered to contain and/or express DNA sequences encoding the RsGluCl. An expression vector containing DNA encoding a RsGluCl-like protein may be used for expression of RsGluCl in a recombinant host cell. Such recombinant host cells can be cultured under suitable conditions to produce RsGluCl or a biologically equivalent form. Expression vectors may include, but are not limited to, cloning vectors, modified cloning vectors, specifically designed plasmids or viruses. Commercially available mammalian expression vectors which may be suitable for recombinant RsGluCl expression, include but are not limited to, pcDNA3.neo (Invitrogen), pcDNA3.1 (Invitrogen), pCI-neo (Promega), pLITMUS28, pLITMUS29, pLITMUS38 and pLITMUS39 (New England Bioloabs), pcDNAI, pcDNAI-amp (Invitrogen), pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUC-Tag (ATCC 37460), and IZD35 (ATCC 37565). Also, a variety of bacterial expression vectors may be used to express recombinant RsGluCl in bacterial cells. Commercially available bacterial expression vectors which may be suitable for recombinant RsGluCl expression include, but are not limited to pCR2.1 (Invitrogen), pET11a (Novagen), lambda gt11 (Invitrogen), and pKK223-3 (Pharmacia). In addition, a variety of fungal cell expression vectors may be used to express recombinant RsGluCl in fungal cells. Commercially available fungal cell expression vectors which may be suitable for recombinant RsGluCl expression include but are not limited to pYES2 Invitrogen) and *Pichia* expression vector (Invitrogen). Also, a variety of insect cell expression vectors may be used to express recombinant protein in insect cells. Commercially available insect cell expression vectors which may be suitable for recombinant expression of RsGluCl include but are not limited to pBlueBacIIIand pBlueBacHis2 (Invitrogen), and pAcG2T (Pharmingen).

Recombinant host cells may be prokaryotic or eukaryotic, including but not limited to, bacteria such as *E. coli*, fungal cells such as yeast, mammalian cells including, but not limited to, cell lines of bovine, porcine, monkey and rodent origin; and insect cells including but not limited to *R. sanguineus* and silkworm derived cell lines. For instance, one insect expression system utilizes *Spodoptera frugiperda* (Sf21) insect cells (invitrogen) in tandem with a baculovirus expression vector (pAcG2T, Pharmingen). Also, mammalian species which may be suitable and which are commercially available, include but are not limited to, L cells L-M(TK$^-$) (ATCC CCL 1.3), L cells L-M (ATCC CCL 1.2), Saos-2 (ATCC HTB-85), 293 (ATCC CRL 1573), Raji (ATCC CCL 86), CV-1 (ATCC CCL 70), COS-1 (ATCC CRL 1650), COS-7 (ATCC CRL 1651), CHO-1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171) and CPAE (ATCC CCL 209).

The specificity of binding of compounds showing affinity for RsGluCl is shown by measuring the affinity of the compounds for recombinant cells expressing the cloned receptor or for membranes from these cells, which form a functional single, homomultimeric or heteromultimeric membrane channel. Expression of the cloned receptor and screening for compounds that bind to RsGluCl or that inhibit the binding of a known, radiolabeled ligand of RsGluCl to these cells, or membranes prepared from these cells, provides an effective method for the rapid selection of compounds with high affinity for RsGluCl. Such ligands need not necessarily be radiolabeled but can also be nonisotopic compounds that can be used to displace bound radiolabeled compounds or that can be used as activators in functional assays. Compounds identified by the above method are likely to be agonists or antagonists of RsGluCl and may be peptides, proteins, or non-proteinaceous organic or inorganic molecules.

A preferred aspect for screening for modulators of RsGluCl channel activity is an expression system for electrophysiologically-based assays for measuring ligand gated channel activity (such as GluCl channel activity) comprising injecting the DNA or RNA molecules of the present invention into *Xenopus laevis* oocytes. The general use of *Xenopus* oocytes in the study of ion channel activity is known in the art (Dascal, 1987, *Crit. Rev. Biochem.* 22:317-317; Lester, 1988, *Science* 241: 1057-1063; see also *Methods of Enzymology*, Vol. 207, 1992, Ch. 14-25, Rudy and Iverson, ed., Academic Press, Inc., New York). The *Xenopus* oocytes are injected with nucleic acid material, including but not limited to DNA, mRNA or cRNA which encode a ligand gated-channel, whereafter channel activity may be measured as well as response of the channel to various modulators.

Accordingly, the present invention is directed to methods for screening for compounds which modulate the expression of DNA or RNA encoding a RsGluCl protein as well as compounds which effect the function of the RsGluCl protein. Methods for identifying agonists and antagonists of other receptors are well known in the art and can be adapted to identify agonists and antagonists of a RsGluCl channel. For example, Cascieri et al. (1992, *Molec. Pharmacol.* 41:109-1099) describe a method for identifying substances that inhibit agonist binding to rat neurokinin receptors and thus are potential agonists or antagonists of neurokinin receptors. The method involves transfecting COS cells with expression vectors containing rat neurokinin receptors, allowing the transfected cells to grow for a time sufficient to allow the neurokinin receptors to be expressed, harvesting the transfected cells and resuspending the cells in assay buffer containing a known radioactively labeled agonist of the neurokinin receptors either in the presence or the absence of the substance, and then measuring the binding of the radioactively labeled known agonist of the neurokinin receptor to the neurokinin receptor. If the amount of binding of the known agonist is less in the presence of the substance than in the absence of the substance, then the substance is a potential ligand of the neurokinin receptor. Where binding of the substance such as an agonist or antagonist to RsGluCl is measured, such binding can be measured by employing a labeled ligand. The ligand can be labeled in any convenient manner known to the art, e.g., radioactively, fluorescently, enzymatically.

Therefore, the present invention is directed to methods for screening for compounds which modulate the expression of DNA or RNA encoding a RsGluCl protein. Compounds which modulate these activities may be DNA, RNA, peptides, proteins, or non-proteinaceous organic or inorganic molecules. Compounds may modulate by increasing or attenuating the expression of DNA or RNA encoding RsGluCl, or the function of the RsGluCl-based channels. Compounds that modulate the expression of DNA or RNA encoding RsGluCl or the biological function thereof may be detected by a variety of assays. The assay may be a simple "yes/no" assay to determine whether there is a change in expression or function. The assay may be made quantitative by comparing the expression or function of a test sample with the levels of expression or function in a standard sample. Kits containing RsGluCl, antibodies to RsGluCl, or modified RsGluCl may be prepared by known methods for such uses.

To this end, the present invention relates in part to methods of identifying a substance which modulates RsGluCl receptor activity, which involves:

(a) adding a test substance in the presence and absence of a RsGluCl receptor protein wherein said RsGluCl receptor protein comprises the amino acid sequence as set forth in SEQ ID NOs: 2, 6 and/or 8; and, (b) measuring and comparing the effect of the test substance in the presence and absence of the RsGluCl receptor protein or respective functional channel.

In addition, several specific embodiments are disclosed herein to show the diverse types of screening or selection assays which the skilled artisan may utilize in tandem with an expression vector directing the expression of the RsGluCl receptor protein. Methods for identifying ligands of other receptors are well known in the art and can be adapted to ligands of RsGluCl. Therefore, these embodiments are presented as examples and not as limitations. To this end, the present invention includes assays by which RsGluCl modulators (such as agonists and antagonists) may be identified. Accordingly, the present invention includes a method for determining whether a substance is a potential agonist or antagonist of RsGluCl that comprises:

(a) transfecting or transforming cells with an expression vector that directs expression of RsGluCl in the cells, resulting in test cells;

(b) allowing the test cells to grow for a time sufficient to allow RsGluCl to be expressed and for a functional channel to be generated;

(c) exposing the cells to a labeled ligand of RsGluCl in the presence and in the absence of the substance;

(d) measuring the binding of the labeled ligand to the RsGluCl channel; where if the amount of binding of the labeled ligand is less in the presence of the substance than in the absence of the substance, then the substance is a potential ligand of RsGluCl.

The conditions under which step (c) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C. The test cells may be harvested and resuspended in the presence of the substance and the labeled ligand. In a modification of the above-described method, step (c) is modified in that the cells are not harvested and resuspended but rather the radioactively labeled known agonist and the substance are contacted with the cells while the cells are attached to a substratum, e.g., tissue culture plates.

The present invention also includes a method for determining whether a substance is capable of binding to RsGluCl, i.e., whether the substance is a potential modulator of RsGluCl channel activation, where the method comprises:

(a) transfecting or transforming cells with an expression vector that directs the expression of RsGluCl in the cells, resulting in test cells;

(b) exposing the test cells to the substance;

(c) measuring the amount of binding of the substance to RsGluCl;

(d) comparing the amount of binding of the substance to RsGluCl in the test cells with the amount of binding of the substance to control cells that have not been transfected with RsGluCl;

wherein if the amount of binding of the substance is greater in the test cells as compared to the control cells, the substance is capable of binding to RsGluCl. Determining whether the substance is actually an agonist or antagonist can then be accomplished by the use of functional assays, such as an electrophysiological assay described herein.

The conditions under which step (b) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C. The test cells are harvested and resuspended in the presence of the substance.

The above described assays may be functional assays, where electrophysiological assays (e.g., see Example 2) may be carried out in transfected mammalian cell lines, an insect cell line, or *Xenopus* oocytes to measure the various effects test compounds may have on the ability of a known ligand (such as glutamate) to activate the channel, or for a test compound to modulate activity in and of itself (similar to the effect of ivermectin on known GluCl channels). Therefore, the skilled artisan will be comfortable adapting the cDNA clones of the present invention to known methodology for both initial and secondary screens to select for compounds that bind and/or activate the functional RsGluCl channels of the present invention.

A preferred method of identifying a modulator of a RsGluCl channel protein comprise firstly contacting a test compound with a *R. sanguiizeus* RsGluCl channel protein selected from the group consisting of SEQ ID NOs:2, 4, 6 and 8; and, secondly measuring the effect of the test compound on the RsGluCl channel protein. A preferred aspect involves using a *R. sanguineus* RsGluCl protein which is a product of a DNA expression vector contained within a recombinant host cell.

Another preferred method of identifying a compound that modulates RsGluCl glutamate-gated channel protein activity comprises firstly injecting into a host cell a population of nucleic acid molecules, at least a portion of which encodes a *R. sanguineus* GluCl channel protein selected from the group consisting of SEQ ID NOs:2, 4, 6 and 8, such that expression of said portion of nucleic acid molecules results in an active ligand-gated channel, secondly measuring host cell membrane-current in the presence and absense of a test compound. Numerous templates may be used, including but not limited to complementary DNA, poly $A^+$ messenger RNA and complementary RNA.

The DNA molecules, RNA molecules, recombinant protein and antibodies of the present invention may be used to screen and measure levels of RsGluCl. The recombinant proteins, DNA molecules, RNA molecules and antibodies lend themselves to the formulation of kits suitable for the detection and typing of RsGluCl. Such a kit would comprise a compartmentalized carrier suitable to hold in close confinement at least one container. The carrier would further comprise reagents such as recombinant RsGluCl or anti-RsGluCl antibodies suitable for detecting RsGluCl. The carrier may also contain a means for detection such as labeled antigen or enzyme substrates or the like.

The assays described herein can be carried out with cells that have been transiently or stably transfected with RsGluCl. The expression vector may be introduced into host cells via any one of a number of techniques including but not limited to transformation, transfection, protoplast fusion, and electroporation. Transfection is meant to include any method known in the art for introducing RsGluCl into the test cells. For example, transfection includes calcium phosphate or calcium chloride mediated transfection, lipofection, infection with a retroviral construct containing RsGluCl, and electroporation. The expression vector-containing cells are individually analyzed to determine whether they produce RsGluCl protein. Identification of RsGluCl expressing cells may be done by several means, including but not limited to immunological reactivity with anti-RsGluCl antibodies, labeled ligand binding, or the presence of functional, non-endogenous RsGluCl activity.

The specificity of binding of compounds showing affinity for RsGluCl is shown by measuring the affinity of the compounds for recombinant cells expressing the cloned receptor or for membranes from these cells. Expression of the cloned receptor and screening for compounds that bind to RsGluCl or that inhibit the binding of a known, ligand of RsGluCl to these cells, or membranes prepared from these cells, provides an effective method for the rapid selection of compounds with high affinity for RsGluCl. Such ligands need not necessarily be radiolabeled but can also be nonisotopic compounds that can be used to displace bound radioactively, fluorescently or enzymatically labeled compounds or that can be used as activators in functional assays. Compounds identified by the above method are likely to be agonists or antagonists of RsGluCl.

Therefore, the specificity of binding of compounds having affinity for RsGluCl is shown by measuring the affinity of the compounds for recombinant cells expressing the cloned receptor or for membranes from these cells. Expression of the cloned receptor and screening for compounds that bind to RsGluCl or that inhibit the binding of a known, radiolabeled ligand of RsGluCl (such as glutamate, ivermectin or nodulisporic acid) to these cells, or membranes prepared from these cells, provides an effective method for the rapid selection of compounds with high affinity for RsGluCl. Such ligands need not necessarily be radiolabeled but can also be nonisotopic compounds that can be used to displace bound radioactively, fluorescently or enzymatically labeled compounds or that can be used as activators in functional assays. Compounds identified by the above method again are likely to be agonists or antagonists of RsGluCl. As noted elsewhere in this specification, compounds may modulate by increasing or attenuating the expression of DNA or RNA encoding RsGluCl, or by acting as an agonist or antagonist of the RsGluCl receptor protein. Again, these compounds that modulate the expression of DNA or RNA encoding RsGluCl or the biological function thereof may be detected by a variety of assays. The assay may be a simple "yes/no" assay to determine whether there is a change in expression or function. The assay may be made quantitative by comparing the expression or function of a test sample with the levels of expression or function in a standard sample.

RsGluCl1 and/or 2 gated chloride channel functional assays measure one or more ligand-gated chloride channel activities where the channel is made up in whole, or in part, by the RsGluCl channel. RsGluCl channel activity can be measured using the channel described herein by itself; or as a subunit in combination with one or more additional ligand-gated chloride channel subunits (preferably one or more RsGluCl), where the subunits combine together to provide functional channel activity. Assays measuring RsGluCl-gated chloride channel activity include functional screening using $^{36}$Cl, functional screening using patch clamp electrophysiology and functional screening using fluorescent dyes. Techniques for carrying out such assays in general are well known in the art. (See, for example, Smith et al., 1998, *European Journal of Pharmacology* 159:261-269; Gonzalez and Tsien, 1997, *Chemistry & Biology* 4:269-277; Millar et al., 1994, *Proc. R. Soc. Lond. B.* 258:307-314; Rauh et al., 1990 *TiPS* 11:325-329, and Tsien et al., U.S. Pat. No. 5,661,035.) Functional assays can be performed using individual compounds or preparations containing different compounds. A preparation containing different compounds where one or more compounds affect RsGluCl channel activity can be divided into smaller groups of compounds to identify the compound(s) affecting RsGluCl channel activity. In an, embodiment of the present invention a test preparation containing at least 10 compounds is used in a functional assay. Recombinantly produced RsGluCl channels present in different environments can be used in a functional assay. Suitable environments include live cells and purified cell extracts containing the RsGluCl channel and an appropriate membrane for activity; and the use of a purified RsGluCl channel produced by recombinant means that is introduced into a different environment suitable for measuring RsGluCl channel activity. RsGluCl derivatives can be used to assay for compounds active at the channel and to obtain information concerning different regions of the channel. For example, RsGluCl channel derivatives can be produced where amino acid regions in the native channel are altered and the effect of the alteration on channel activity can be measured to obtain information regarding different channel regions.

Expression of RsGluCl DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

Following expression of RsGluCl in a host cell, RsGluCl protein may be recovered to provide RsGluCl protein in active form. Several RsGluCl protein purification procedures are available and suitable for use. Recombinant RsGluCl protein may be purified from cell lysates and extracts by various combinations of, or individual application of salt fractionation, ion exchange chromatography, size exclusion chromatography, hydroxylapatite adsorption chromatography and hydrophobic interaction chromatography. In addition, recombinant RsGluCl protein can be separated from other cellular proteins by use of an immunoaffinity-column made with monoclonal or polyclonal antibodies specific for full-length RsGluCl protein, or polypeptide fragments of RsGluCl protein.

Expression of RsGluCl DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

Following expression of RsGluCl in a host cell, RsGluCl protein may be recovered to provide RsGluCl protein in active form. Several RsGluCl protein purification procedures are available and suitable for use. Recombinant RsGluCl protein may be purified from cell lysates and extracts by various combinations of, or individual application of salt fractionation, ion exchange chromatography, size exclusion chromatography, hydroxylapatite adsorption chromatography and hydrophobic interaction chromatography. In addition, recombinant RsGluCl protein can be separated from other cellular proteins by use of an immunoaffinity column made with monoclonal or polyclonal antibodies specific for full-length RsGluCl protein, or polypeptide fragments of RsGluCl protein.

Polyclonal or monoclonal antibodies may be raised against RsGluCl1 or RsGluCl2 or a synthetic peptide (usually from about 9 to about 25 amino acids in length) from a portion of RsGluCl or RsGluCl2 as disclosed in SEQ ID NOs:2, 4, 6 and/or 8. Monospecific antibodies to RsGluCl are purified from mammalian antisera containing antibodies reactive against RsGluCl or are prepared as monoclonal antibodies reactive with RsGluCl using the technique of Kohler and Milstein (1975, *Nature* 256: 495-497). Monospecific antibody as used herein is defined as a single antibody species or multiple antibody species with homogenous binding characteristics for RsGluCl. Homogenous binding as used herein refers to the ability of the antibody species to bind to a specific antigen or epitope, such as those associated with RsGluCl, as described above. Human RsGluCl-specific antibodies are raised by immunizing animals such as mice, rats, guinea pigs, rabbits, goats, horses and the like, with an appropriate concentration of RsGluCl protein or a synthetic peptide generated from a portion of RsGluCl with or without an immune adjuvant.

Preimmune serum is collected prior to the first immunization. Each animal receives between about 0.1 mg and about 1000 mg of RsGluCl protein associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of RsGluCl protein or peptide fragment thereof in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of RsGluCl in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with RsGluCl are prepared by immunizing inbred mice, preferably Balb/c, with RsGluCl protein. The mice are immunized by the IP or SC route with about 1 mg to about 100 mg, preferably about 10 mg, of RsGluCl protein in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 mg of RsGluCl in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using RsGluCl as the antigen. The culture fluids are also tested in the Ouchterlony precipitation assay to determine the isotype of the mAb. Hybridoma cells from antibody positive wells are cloned by a technique such as the soft agar technique of MacPherson, 1973, Soft Agar Techniques, in *Tissue Culture Methods and Applications*, Kruse and Paterson, Eds., Academic Press.

Monoclonal antibodies are produced in vivo by injection of pristine primed Balb/c mice, approximately 0.5 ml per mouse, with about $2\times10^6$ to about $6\times10^6$ hybridoma cells about 4 days after priming. Ascites fluid is collected at approximately 8-12 days after cell transfer and the monoclonal antibodies are purified by techniques known in the art.

In vitro production of anti-RsGluCl mAb is carried out by growing the hybridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of RsGluCl in body fluids or tissue and cell extracts.

It is readily apparent to those skilled in the art that the above described methods for producing monospecific antibodies may be utilized to produce antibodies specific for RsGluCl peptide fragments, or a respective full-length RsGluCl.

RsGluCl antibody affinity columns are made, for example, by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing full-length RsGluCl or RsGluCl protein fragments are slowly passed through the column. The column is then washed with phosphate buffered saline until the optical density ($A_{280}$) falls to background, then the protein is eluted with 0.23 M glycine-HCl (pH 2.6). The purified RsGluCl protein is then dialyzed against phosphate buffered saline.

The present invention also relates to a non-human transgenic animal which is useful for studying the ability of a variety of compounds to act as modulators of RsGluCl, or any alternative functional RsGluCl channel in vivo by providing cells for culture, in vitro. In reference to the transgenic animals of this invention, reference is made to transgenes and genes. As used herein, a transgene is a genetic construct including a gene. The transgene is integrated into one or more chromosomes in the cells in an animal by methods known in the art. Once integrated, the transgene is carried in at least one place in the chromosomes of a transgenic animal. Of course, a gene is a nucleotide sequence that encodes a protein, such as one or a combination of the cDNA clones described herein. The gene and/or transgene may also include genetic regulatory elements and/or structural elements known in the art A type of target cell for transgene introduction is the embryonic stem cell (ES). ES cells can be obtained from pre-implantation embryos cultured in vitro and fused with embryos (Evans et al., 1981, *Nature* 292:154-156; Bradley et al., 1984, *Nature* 309:255-258; Gossler et al., 1986, *Proc. Natl. Acad. Sci.* USA 83:9065-9069; and Robertson et al., 1986 *Nature* 322:445-448). Transgenes can be efficiently introduced into the ES cells by a variety of standard techniques such as DNA transfection, microinjection, or by retrovirus-mediated transduction. The resultant transformed ES cells can thereafter be combined with blastocysts from a non-human animal. The introduced ES cells thereafter colonize the embryo and contribute to the germ line of the resulting chimeric animal (Jaenisch, 1988, *Science* 240: 1468-1474). It will also be within the purview of the skilled artisan to produce transgenic or knock-out invertebrate animals (e.g., *C. elegans*) which express the RsGluCl transgene in a wild type *C. elegans* GluCl background as well in *C. elegans* mutants knocked out for one or both of the *C. elegans* GluCl subunits.

Pharmaceutically useful compositions comprising modulators of RsGluCl may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, modified RsGluCl, or either RsGluCl agonists or antagonists including tyrosine kinase activators or inhibitors.

Therapeutic or diagnostic compositions of the invention are administered to an individual in amounts sufficient to treat or diagnose disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages. Alternatively, co-administration or sequential administration of other agents may be desirable.

The present invention also has the objective of providing suitable topical, oral, systemic and parenteral pharmaceutical formulations for use in the novel methods of treatment of the present invention. The compositions containing compounds identified according to this invention as the active ingredient can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the 1 patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

The following examples are provided to illustrate the present invention without, however, limiting the same hereto.

EXAMPLE 1

Isolation and Characterization of DNA Molecules Encoding RsGluCl and RsGluCl2

Most molecular procedures were performed following standard procedures available in references such as Ausubel et. al. (1992. Short protocols in molecular biology. F. M. Ausubel et al., —$2^{nd}$. ed. (John Wiley & Sons), and Sambrook et al. (1989. Molecular cloning. A laboratory manual. J. Sambrook, E. F. Fritsch, and T. Maniatis—$2^{nd}$ ed. (Cold Spring Harbor Laboratory Press).

RsGluCl1—Adult brown dog tick polyA$^+$ RNA was isolated using the Poly(A)Pure™ mRNA Isolation Kit (Ambion). Tick cDNA was synthesized using oligo-dT primers and the ZAP cDNA® Synthesis Kit (Stratagene), and cDNA >1 kb was selected using cDNA Size Fractionation Columns (BRL). A tick cDNA library was constructed in the Lambda ZAP® II vector using the GIGAPACK™ III Gold Cloning Kit (Stratagene). A *Drosophila* GluCl cDNA fragment spanning the M1 to M3 region was used in a low-stringency screen [25% v/v formamide/5×SSCP (1XSSCP=120 mM NaCl/15 mM sodium citrate/20 mM sodium phosphate, pH 6.8)/0.1% SDS/10× Denhardt's solution/salmon sperm DNA (250 µg/ml) at 42° C.; wash, 0.2×SSC/0.1% SDS at 42° C.] of the tick cDNA library. The nucleotide sequence of the probe is as follows:

```
                                                (SEQ ID NO: 12)
5'ATTACTTAATACAAATTTATATACCATGCTGTATGTTGGTCATTGTAT

CATGGGTATCATTCTGGCTGGATCAAGGAGCAGTACCGGCGCGAGTGTCA

CTGGGTGTCACCACCCTGCTGACCATGGCCACCCAGACGTCGGGCATAAA

CGCCTCCCTGCCGCCCGTTTCCTATACGAAGGCCATCGATGTGTGGACAG

GCGTGTGTCTGACGTTCGTGTTCGGGGCCCTGCTCGAGTTCGCCCTGGT

G-3'.
```

Filters were exposed for eleven days and six positives were isolated for sequence analysis. Three of the clones (T12, T82 and T32) encode GluCl-related proteins and were sequenced on both strands.

RsGluCl2—Poly (A)+ RNA was isolated from brown dog tick heads. First strand cDNA was synthesized from 50 ng RNA using a SUPERSCRIPT preamplification System (Life Technologies). A tenth of the first strand reaction was used for PCR. The degenerate oligos utilized were designed based on sequences obtained from C. elegans, Drosophila, and flea (C. felis) GluCls:

```
Forward (27F2):
                                                (SEQ ID NO: 9)
GGAT(G/T)CCNGA(C/T)N(C/T)NTT(C/T)TTNN(A/C)NA(A/C)
(C/T)G;

Reverse 1 (3AF1):
                                                (SEQ ID NO: 10)
CNA(A/G)  (A/C)A(A/G)NGCNC(A/C)GAANA(C/T)  (A/G)AA
(C/T)G;

Reverse 2 (3AF2):
                                                (SEQ ID NO: 11)
CAN(A/G)CNCCN(A/G)  (G/T)CCANAC(A/G)TCNA(C/T)N
(A/G)C.
```

Two PCR rounds, using the combinations "27F2+3AF1, then 27F2+3BF2" were performed. The cycles were as follow: 1× (95° C. for 120 sec.), then 30× (95° C. for 45 sec.; 50° C. for 90 sec.; and 72° C. for 120 sec.), then 1× (72° C. for 120 sec.). Reagents were from Life Technology Inc. The oligonucleotide concentration was 5 μM. One tenth of the PCR reaction products was tested by Southern blot analysis, in order to identify and prevent the PCR-cloning of contaminating sequences. Novel PCR products of the appropriate size were cloned into the PCR2.1 plasmid vector using a "TA" cloning kit Invitrogen, Inc.). Following sequence analysis (ABI Prism, PE Applied Biosystems), selected PCR clone inserts were radiolabelled and used as probes to screen a cDNA library generated into the Uni-ZAP® vector (Stratagene, Inc.) from using the RNA preparation mentioned above. Sequences from full-length cDNA clones were analysed using the GCG Inc. package. Subcloning of RsGluCl2 into a mammalian expression vector was done by excision of an 1.85 kb coding-region-containing fragment (XhoI-EcoRI digest) from the original insert of clone RsGluCl2 B1 from the UniZap® pBS plasmid, followed by ligation into the TetSplice® vector (Life Technologies Inc.). cDNA clones T12 and T82 are identical in the coding region except for a single nucleotide difference resulting in a single amino acid substitution which is probably a naturally occurring polymorphism. The T32 clone has 2 additional exons not present in the T12 and T82 cDNAs, one is near the 5' end of the coding region (135 bp exon) and the other is in the M3-M4 intracellular linker (96 bp exon). Additionally, these optional exons are not included in DrosGluCl-1 ORF. These cDNA clones are also denoted as RsGluCl-1L (T32-2.48 kb) and RsGluCl-1S (T12 and T82-2.126 kb). The predicted RsGluCl-1S protein is approximately 71% identical to the DrosGluCl1 protein.

EXAMPLE 2

Functional Expression of RsGluCl1 and RsGluCl2 Clones in *Xenopus* Oocytes

*Xenopus laevis* oocytes were prepared and injected using standard methods previously described [Arena, J. P., Liu, K. K., Paress, P. S. & Cully, D. P. Mol. Pharmacol. 40, 368-374 (1991); Arena, J. P., Liu, K. K., Paress, P. S., Schaeffer, J. M. & Cully, D. F., Mol. Brain. Res. 15, 339-348 (1992)]. Adult female *Xenopus laevis* were anesthetized with 0.17% tricaine methanesulfonate and the ovaries were surgically removed and placed in a solution consisting of (mM): NaCl 82.5, KCl 2, $MgCl_2$ 1, HEPES 5, NaPyruvate 2.5, Penicillin G. 100,000 units/L, Streptomycin Sulfate 1000 mg/L, pH 7.5 (Mod. OR-2). Ovarian lobes were broken open, rinsed several times in Mod. OR-2, and incubated in 0.2% collagenase (Sigma, Type1) in Mod. OR-2 at room temperature with gentle shaking. After 1 hour the collagenase solution was renewed and the oocytes were incubated for an additional 30-90 min until approximately 50% of the oocytes were released from the ovaries. Stage V and VI oocytes were selected and placed in media containing (mM): NaCl 96, KCl 2, $MgCl_2$ 1, $CaCl_2$ 1.8, HEPES 5, NaPyruvate 2.5, theophylline 0.5, gentamicin 50 mg/ml, pH 7.5 (ND-96) for 16-24 hours before injection. Oocytes were injected with 50 nl of Dv8, Dv9, RsGluCl1 or RsGluCl2 RNA at a concentration of 0.2 mg/ml. Oocytes were incubated at 18° C. for 1-6 days in ND-96 before recording.

Recordings were made at room temperature in modified ND-96 consisting of (mM: NaCl 96, $MgCl_2$ 1, $CaCl_2$ 0.1, $BaCl_2$ 3.5, HEPES 5, pH 7.5. Oocytes were voltage clamped using a Dagan CA1 two microelectrode amplifier (Dagan Corporation, Minneapolis, Minn.) interfaced to a Macintosh 7100/80 computer. The current passing electrode was filled with 0.7 M KCl, 1.7 M KCitrate, and the voltage recording electrode was filled with 1 M KCl. Throughout the experiment oocytes were superfused with modified ND-96 (control solution) or with ND-96 containing potential channel activators and blockers at a rate of approximately 3 ml/min. Data were acquired at 100 Hz and filtered at 33.3 Hz using Pulse software from HEKA Elektronik (Lambrecht, Germany). All recordings were performed from a holding potential of either 0 or −30 mV.

cRNA was synthesized from the RsGluCl 1S clone T12 and expressed in *Xenopus* oocytes. The channel encoded by RsGluCl-1 is a glutamate-gated chloride channel activated by IVM-$PO_4$.

FIG. 10 shows the glutamate-activated current in oocytes injected with RsGluCl1 T12 RNA. Current activation was maximal with 10 μM glutamate and no current was seen in uninjected oocytes. Application of 100 nM ivermectin produces a similar although non-inactivating current.

Figure 11:
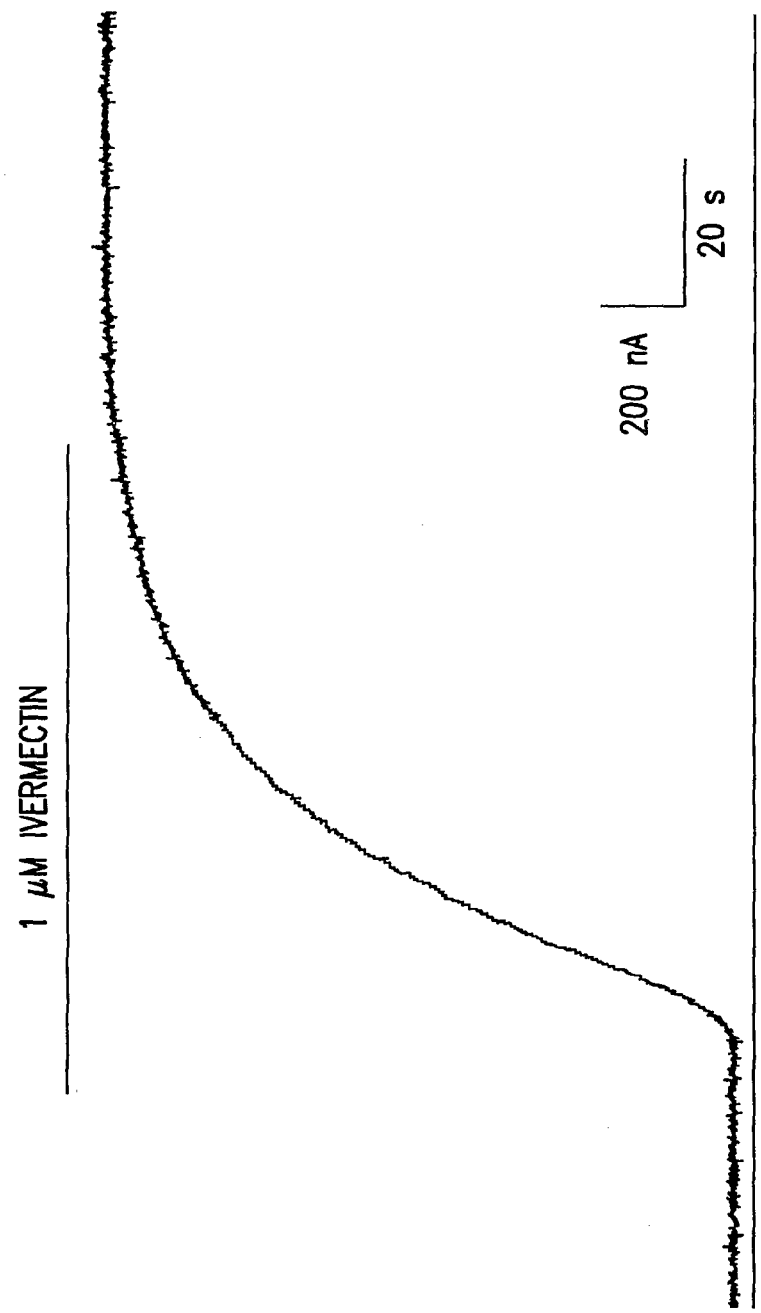
FIG. 11 shows the activation by ivermectin of RsGluCl2 expressed in *Xenopus* oocytes. Current activation was maximal with ~1 μM ivermectin.

FIG. 11 shows the activation by ivermectin of RsGluCl2 expressed in *Xenopus* oocytes. Current activation was maximal with ~1 µM ivermectin and glutamate failed to activate a current when expressed as a single functional channel.

EXAMPLE 3

Functional Expression of RsGluCls Clones in Mammalian Cells

A RsGluCl may be subcloned into a mammalian expression vector and used to transfect the mammalian cell line of choice. Stable cell clones are selected by growth in the presence of G418. Single G418 resistant clones are isolated and tested to confirm the presence of an intact RsGluCl gene. Clones containing the RsGluCls are then analyzed for expression using immunological techniques, such as immuneprecipitation, Western blot, and immunofluorescence using antibodies specific to the RsGluCl proteins, Antibody is obtained from rabbits innoculated with peptides that are synthesized from the amino acid sequence predicted from the RsGluCl sequences. Expression is also analyzed using patch clamp electrophysiological techniques and an anion flux assay.

Cells that are expressing RsGluCl stably or transiently, are used to test for expression of active channel proteins. These cells are used to identify and examine other compounds for their ability to modulate, inhibit or activate the respective channel.

Cassettes containing the RsGluCl cDNA in the positive orientation with respect to the promoter are ligated into appropriate restriction sites 3' of the promoter and identified by restriction site mapping and/or sequencing. These cDNA expression vectors may be introduced into fibroblastic host cells, for example, COS-7 (ATCC# CRL1651), and CV-1 tat [Sackevitz et al., 1987, *Science* 238: 1575], 293, L (ATCC# CRL6362) by standard methods including but not limited to electroporation, or chemical procedures (cationic liposomes, DEAE dextran, calcium phosphate). Transfected cells and cell culture supernatants can be harvested and analyzed for RsGluCl expression as described herein.

All of the vectors used for mammalian transient expression can be used to establish stable cell lines expressing RsGluCl. Unaltered RsGluCl cDNA constructs cloned into expression vectors are expected to program host cells to make RsGluCl protein. In addition, RsGluCl is expressed extracellularly as a secreted protein by ligating RsGluCl cDNA constructs to DNA encoding the signal sequence of a secreted protein. The transfection host cells include, but are not limited to, CV-1-P [Sackevitz et al., 1987, *Science* 238: 1575], tk-L [Wigler, et al., 1977, *Cell* 11: 223], NS/0, and dHFr-CHO [Kaufman and Sharp, 1982, *J. Mol. Biol.* 159: 601].

Co-transfection of any vector containing a RsGluCl cDNA with a drug selection plasmid including, but not limited to G418, aminoglycoside phosphotransferase; hygromycin, hygromycin-B phosphotransferase; APRT, xanthine-guanine phosphoribosyl-transferase, will allow for the selection of stably transfected clones. Levels of RsGluCl are quantitated by the assays described herein. RsGluCl cDNA constructs way also be ligated into vectors containing amplifiable drug-resistance markers for the production of mammalian cell clones synthesizing the highest possible levels of RsGluCl. Following introduction of these constructs into cells, clones containing the plasmid are selected with the appropriate agent, and isolation of an over-expressing clone with a high copy number of plasmids is accomplished by selection with increasing doses of the agent. The expression of recombinant RsGluCl is achieved by transfection of full-length RsGluCl cDNA into a mammalian host cell.

EXAMPLE 4

Cloning of RsGluCl cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL# 1711). A recombinant baculoviruse expressing RsGluCl cDNA is produced by the following standard methods (In Vitrogen Maxbac Manual): The RsGluCl cDNA constructs are ligated into the polyhedrin gene in a variety of baculovirus transfer vectors, including the pAC360 and the BlueBac vector (InVitrogen). Recombinant baculoviruses are generated by homologous recombination following co-transfection of the baculovirus transfer vector and linearized AcNPV genomic DNA [Kitts, 1990, *Nuc. Acid. Res.* 18: 5667] into Sf9-cells. Recombinant pAC360 viruses are identified by the absence of inclusion bodies in infected cells and recombinant pBlueBac viruses are identified on the basis of b-galactosidase expression (Summers, M. D. and Smith, G. E., Texas Agriculture Exp. Station Bulletin No. 1555). Following plaque purification, RsGluCl expression is measured by the assays described herein.

The cDNA encoding the entire open reading frame for RsGluCl GluCl is inserted into the BamHI site of pBlueBacII. Constructs in the positive orientation are identified by sequence analysis and used to transfect Sf9 cells in the presence of linear AcNPV mild type DNA.

EXAMPLE 5

Cloning of RsGluCl cDNA into a Yeast Expression Vector

Recombinant RsGluCl is produced in the yeast *S. cerevisiae* following the insertion of the optimal RsGluCl cDNA cistron into expression vectors designed to direct the intracellular or extracellular expression of heterologous proteins. In the case of intracellular expression, vectors such as EmBLyex4 or the like are ligated to the RsGluCl cistron [Rinas, et al., 1990, *Biotechnology* 8: 543-545; Horowitz B. et al., 1989, *J. Biol. Chem.* 265: 4189-4192]. For extracellular expression, the RsGluCl GluCl cistron is ligated into yeast expression vectors which fuse a secretion signal (a yeast or mammalian peptide) to the $NH_2$ terminus of the RsGluCl protein [Jacobson, 1989, *Gene* 85: 511-516; Riett and Bellon, 1989, *Biochem.* 28: 2941-2949].

These vectors include, but are not limited to pAVE1-6, which fuses the human serum albumin signal to the expressed cDNA [Steep, 1990, *Biotechnology* 8: 42-46], and the vector pL8PL which fuses the human lysozyme signal to the expressed cDNA [Yamamoto, *Biochem.* 28: 2728-2732)]. In addition, RsGluCl is expressed in yeast as a fusion protein conjugated to ubiquitin utilizing the vector pVEP [Ecker, 1989, *J. Biol. Chem.* 264: 7715-7719, Sabin, 1989 *Biotechnology* 7: 705-709, McDonnell, 1989, *Mol. Cell. Biol.* 9: 5517-5523 (1989)]. The levels of expressed RsGluCl are determined by the assays described herein.

EXAMPLE 6

Purification of Recombinant RsGluCl

Recombinantly produced RsGluCl may be purified by antibody affinity chromatography. RsGluCl GluCl antibody affinity columns are made by adding the anti-RsGluCl GluCl antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) together with appropriate membrane solubilizing agents such as detergents and the cell culture supernatants or cell extracts containing solubilized RsGluCl are slowly passed through the column. The column is then washed with phosphate-buffered saline together with detergents until the optical density (A280) falls to background, then the protein is eluted with 0.23 M glycine-HCl (pH 2.6) together with detergents. The purified RsGluCl protein is then dialyzed against phosphate buffered saline.

What is claimed is:

1. A method of identifying a modulator of a GluCl channel protein, comprising:
   (a) contacting a test compound in the presence and absence of a R. sanguineus GluCl channel protein selected from the group consisting of SEQ ID NO:2, SEQ ID NO;4, and SEQ ID NO:6;
   (b) measuring the effect of the test compound the presence and absence of the R. sanguineus GluCl channel protein of (a), wherein the effect that is measured is selected from the group consisting of: the expression of DNA encoding the R. sanguineus GluCl channel protein of (a), the expression of RNA encoding the R. sanguineus GluCl channel protein of (a), and a channel activity of the R. sanguineus GluCl channel protein of (a); and
   (c) comparing the effect of the test compound in the presence and absence of the R. sanguineus GluCl channel protein,
   wherein if the effect of the test compound measured in the presence of the R. sanguineus GluCl channel protein is greater than or less than the effect measured in the absence of the R. sanguineus GluCl channel protein, the test compound is a modulator of a GluCl channel protein.

2. The method of claim 1 wherein the host cell that expresses the R. sanguineus GluCl channel protein of step (a) is a recombinant host cell.

3. A method of identifying a compound that modulates glutamate-gated channel protein activity, which comprises:
   a) injecting into a host cell a population of nucleic acid molecules, at least of portion of which encodes a R. sanguineus GluCl channel protein selected from the group consisting of SEQ ID NO:2, SEQ ID NO:4, and SEQ ID NO:6 such that expression of said portion of nucleic acid molecules results in an active glutamate-gated channel;
   b) contacting the host cell of (a) with a test compound;
   c) in the presence and absence of the test compound, measuring host cell membrane current of (b) at a holding potential more positive than the reversal potential for chloride; and d) comparing the currents measured in (c),
wherein if the current in the presence of the test compound is greater or less than the current in the absence of the test compound, a compound that modulates glutamate-gated channel protein activity is identified.

4. The method of claim 2 wherein said nucleic acid molecule is selected from the group consisting of complementary DNA, poly A+ messenger RNA and complementary RNA.

* * * * *

SEQUENCE LISTING

```
<160> NUMBER OF SEQ ID NOS: 12

<210> SEQ ID NO 1
<211> LENGTH: 2138
<212> TYPE: DNA
<213> ORGANISM: Rhipicephalus sanguineus
<220> FEATURE:
<221> NAME/KEY: CDS
<222> LOCATION: (331)...(1683)

<400> SEQUENCE: 1
cgctccccca atcctgaggt tccttctaac gagaaggagg agccacagcg ccggctgcgg     60
taccgccgca cgggccaacg tgagaccgcc cgagcccggc gccctgactt aggccgctga    120
gcgaaaccca aggcggcgcg ctggccactc cacgggaacg agaccggccc cctggagacg    180
acatcgtcga ccacaatgaa ctacttctct gacgtggcga agatggtggc ttcatcgaag    240
agagaaatca tcgaagcttt ccacgcgaca tctggagtac acggcgcatg cgaatgagcg    300
aacatcgctg accgagactc gcccgtcacc atg agc gta cat tca tgg cgc ttt     354
                                 Met Ser Val His Ser Trp Arg Phe
                                 1               5 tgt gtc cca ctg gtg gct cta gcg ttt ttc ttg ttg att ctt ctg tcg      402
Cys Val Pro Leu Val Ala Leu Ala Phe Phe Leu Leu Ile Leu Leu Ser
    10                  15                  20 tgt cca tcg gca tgg ggc aag gca aat ttc cgc gct ata gaa aag cgg      450
Cys Pro Ser Ala Trp Gly Lys Ala Asn Phe Arg Ala Ile Glu Lys Arg
25                  30                  35                  40 ata ttg gac agc atc att ggc cag ggt cgt tat gac tgc agg atc cgg      498
Ile Leu Asp Ser Ile Ile Gly Gln Gly Arg Tyr Asp Cys Arg Ile Arg
                45                  50                  55 ccc atg gga att aac aac aca gac ggg ccg gct ctt gta cgc gtt aac      546
Pro Met Gly Ile Asn Asn Thr Asp Gly Pro Ala Leu Val Arg Val Asn
            60                  65                  70 atc ttt gta aga agt atc ggc aga att gat gac gtc acc atg gag tac      594
Ile Phe Val Arg Ser Ile Gly Arg Ile Asp Asp Val Thr Met Glu Tyr
        75                  80                  85 aca gtg caa atg acg ttc aga gag cag tgg cgg gac gag aga ctc cag      642
Thr Val Gln Met Thr Phe Arg Glu Gln Trp Arg Asp Glu Arg Leu Gln
    90                  95                 100 tac gac gac ttg ggc ggc cag gtt cgc tac ctg acg ctc acc gaa ccg      690
Tyr Asp Asp Leu Gly Gly Gln Val Arg Tyr Leu Thr Leu Thr Glu Pro
105                 110                 115                 120 gac aag ctt tgg aag ccg gac ctg ttt ttc tcc aac gag aaa gag gga      738
Asp Lys Leu Trp Lys Pro Asp Leu Phe Phe Ser Asn Glu Lys Glu Gly
                125                 130                 135 cac ttc cac aac atc atc atg ccc aac gtg ctt cta cgc ata cat ccc      786
```

```
                His Phe His Asn Ile Ile Met Pro Asn Val Leu Leu Arg Ile His Pro
                            140                 145                 150 aac ggc gac gtt ctc ttc agc atc aga ata tcc ttg gtg ctt tca tgt         834
Asn Gly Asp Val Leu Phe Ser Ile Arg Ile Ser Leu Val Leu Ser Cys
            155                 160                 165 ccg atg aac ctg aaa ttt tat cct ttg gat aaa caa atc tgc tct atc         882
Pro Met Asn Leu Lys Phe Tyr Pro Leu Asp Lys Gln Ile Cys Ser Ile
    170                 175                 180 gtc atg gtg agc tat ggg tat aca aca gag gac ctg gtg ttt cta tgg         930
Val Met Val Ser Tyr Gly Tyr Thr Thr Glu Asp Leu Val Phe Leu Trp
185                 190                 195                 200 aaa gag ggg gat cct gta cag gtc aca aaa aat ctc cac ttg cca cgt         978
Lys Glu Gly Asp Pro Val Gln Val Thr Lys Asn Leu His Leu Pro Arg
                205                 210                 215 ttc acg ctg gaa agg ttt caa acc gac tac tgc acc agt cgg acc aac        1026
Phe Thr Leu Glu Arg Phe Gln Thr Asp Tyr Cys Thr Ser Arg Thr Asn
            220                 225                 230 act ggc gag tac agc tgc ttg cgc gtg gac ctg gtg ttc aag cgc gag        1074
Thr Gly Glu Tyr Ser Cys Leu Arg Val Asp Leu Val Phe Lys Arg Glu
    235                 240                 245 ttc agc tac tac ctg atc cag atc tac atc ccg tgc tgc atg ctg gtc        1122
Phe Ser Tyr Tyr Leu Ile Gln Ile Tyr Ile Pro Cys Cys Met Leu Val
250                 255                 260 atc gtg tcc tgg gtg tcg ttc tgg ctc gac ccc acc tcg atc ccg gcg        1170
Ile Val Ser Trp Val Ser Phe Trp Leu Asp Pro Thr Ser Ile Pro Ala
265                 270                 275                 280 cga gtg tcg ctg ggc gtc acc acc ctg ctc acc atg gcc acg cag ata        1218
Arg Val Ser Leu Gly Val Thr Thr Leu Leu Thr Met Ala Thr Gln Ile
                285                 290                 295 tcg ggc atc aac gcc tcg ctg cct ccc gtt tcc tac acc aag gcc att        1266
Ser Gly Ile Asn Ala Ser Leu Pro Pro Val Ser Tyr Thr Lys Ala Ile
            300                 305                 310 gac gtg tgg acc ggc gtc tgt ctg acc ttc gta ttc ggc gcg ctc ctc        1314
Asp Val Trp Thr Gly Val Cys Leu Thr Phe Val Phe Gly Ala Leu Leu
    315                 320                 325 gag ttc gcc ctg gtc aac tac gcc tcg cgg tca gat tca cgc cgg cag        1362
Glu Phe Ala Leu Val Asn Tyr Ala Ser Arg Ser Asp Ser Arg Arg Gln
330                 335                 340 aac atg cag aag cag aag cag agg aaa tgg gag ctc gag ccg ccc ctg        1410
Asn Met Gln Lys Gln Lys Gln Arg Lys Trp Glu Leu Glu Pro Pro Leu
345                 350                 355                 360 gac tcg gac cac ctg gag gac ggc gcc acc acg ttc gcc atg agg ccg        1458
Asp Ser Asp His Leu Glu Asp Gly Ala Thr Thr Phe Ala Met Arg Pro
                365                 370                 375 ctg gtg cac cac cac gga gag ctg cat gcc gac aag ttg cgg cag tgc        1506
Leu Val His His His Gly Glu Leu His Ala Asp Lys Leu Arg Gln Cys
            380                 385                 390 gaa gtc cac atg aag acc ccc aag acg aac ctt tgc aag gcc tgg ctt        1554
Glu Val His Met Lys Thr Pro Lys Thr Asn Leu Cys Lys Ala Trp Leu
    395                 400                 405 tcc agg ttt ccc acg cga tcc aaa cgc atc gac gtc gtc tcg cgg atc        1602
Ser Arg Phe Pro Thr Arg Ser Lys Arg Ile Asp Val Val Ser Arg Ile
410                 415                 420 ttc ttt ccg ctc atg ttc gcc ctc ttc aac ctc gtc tac tgg aca acc        1650
Phe Phe Pro Leu Met Phe Ala Leu Phe Asn Leu Val Tyr Trp Thr Thr
425                 430                 435                 440 tac ctc ttc cgg gaa gac gag gaa gac gag tga cagaacacgg acgccacgac     1703
Tyr Leu Phe Arg Glu Asp Glu Glu Asp Glu *
                445                 450
```

```
agccgccatc cgacaccatc gtcactgcag gcacgcactc tgtcgcgcgc acacaccacg    1763
aagaccggcg cgccaacgca cgatgcgcgt tggccgctga aaaacccggg agcggggcgg    1823
tgggggaggc tatgcccggg cccctcgctc ctcatcctcc gtgcacgctc gaatcgtcat    1883
cgccacagcc agaaaaaaaa aagataccgt gcgaaaagtg gcggcaacac aacgtcgacg    1943
ccatcagcgc cgcccagagc tgcaagcggc tcccacatgg ttgccaccgc agcttcctct    2003
acgacccttc atccccaccg gcaccagcta cgagaaaggg accttatttc gggccatccc    2063
tacataggcg actgttgttt tcgcacgaaa gatctttacg cagctgatgc tgaaaaaaaa    2123
aaaaaaaaaa aaaaa                                                    2138
```

<210> SEQ ID NO 2
<211> LENGTH: 450
<212> TYPE: PRT
<213> ORGANISM: Rhipicephalus sanguineus

<400> SEQUENCE: 2

```
Met Ser Val His Ser Trp Arg Phe Cys Val Pro Leu Val Ala Leu Ala
 1               5                  10                  15

Phe Phe Leu Leu Ile Leu Leu Ser Cys Pro Ser Ala Trp Gly Lys Ala
             20                  25                  30

Asn Phe Arg Ala Ile Glu Lys Arg Ile Leu Asp Ser Ile Ile Gly Gln
         35                  40                  45

Gly Arg Tyr Asp Cys Arg Ile Arg Pro Met Gly Ile Asn Asn Thr Asp
     50                  55                  60

Gly Pro Ala Leu Val Arg Val Asn Ile Phe Val Arg Ser Ile Gly Arg
 65                  70                  75                  80

Ile Asp Asp Val Thr Met Glu Tyr Thr Val Gln Met Thr Phe Arg Glu
                 85                  90                  95

Gln Trp Arg Asp Glu Arg Leu Gln Tyr Asp Asp Leu Gly Gly Gln Val
            100                 105                 110

Arg Tyr Leu Thr Leu Thr Glu Pro Asp Lys Leu Trp Lys Pro Asp Leu
        115                 120                 125

Phe Phe Ser Asn Glu Lys Glu Gly His Phe His Asn Ile Ile Met Pro
    130                 135                 140

Asn Val Leu Leu Arg Ile His Pro Asn Gly Asp Val Leu Phe Ser Ile
145                 150                 155                 160

Arg Ile Ser Leu Val Leu Ser Cys Pro Met Asn Leu Lys Phe Tyr Pro
                165                 170                 175

Leu Asp Lys Gln Ile Cys Ser Ile Val Met Val Ser Tyr Gly Tyr Thr
            180                 185                 190

Thr Glu Asp Leu Val Phe Leu Trp Lys Glu Gly Asp Pro Val Gln Val
        195                 200                 205

Thr Lys Asn Leu His Leu Pro Arg Phe Thr Leu Glu Arg Phe Gln Thr
    210                 215                 220

Asp Tyr Cys Thr Ser Arg Thr Asn Thr Gly Glu Tyr Ser Cys Leu Arg
225                 230                 235                 240

Val Asp Leu Val Phe Lys Arg Glu Phe Ser Tyr Tyr Leu Ile Gln Ile
                245                 250                 255

Tyr Ile Pro Cys Cys Met Leu Val Ile Val Ser Trp Val Ser Phe Trp
            260                 265                 270

Leu Asp Pro Thr Ser Ile Pro Ala Arg Val Ser Leu Gly Val Thr Thr
        275                 280                 285

Leu Leu Thr Met Ala Thr Gln Ile Ser Gly Ile Asn Ala Ser Leu Pro
```

-continued

```
                    290                 295                 300
Pro Val Ser Tyr Thr Lys Ala Ile Asp Val Trp Thr Gly Val Cys Leu
305                 310                 315                 320

Thr Phe Val Phe Gly Ala Leu Leu Glu Phe Ala Leu Val Asn Tyr Ala
                325                 330                 335

Ser Arg Ser Asp Ser Arg Arg Gln Asn Met Gln Lys Gln Lys Gln Arg
                340                 345                 350

Lys Trp Glu Leu Glu Pro Pro Leu Asp Ser Asp His Leu Glu Asp Gly
                355                 360                 365

Ala Thr Thr Phe Ala Met Arg Pro Leu Val His His Gly Glu Leu
370                 375                 380

His Ala Asp Lys Leu Arg Gln Cys Glu Val His Met Lys Thr Pro Lys
385                 390                 395                 400

Thr Asn Leu Cys Lys Ala Trp Leu Ser Arg Phe Pro Thr Arg Ser Lys
                405                 410                 415

Arg Ile Asp Val Val Ser Arg Ile Phe Phe Pro Leu Met Phe Ala Leu
                420                 425                 430

Phe Asn Leu Val Tyr Trp Thr Thr Tyr Leu Phe Arg Glu Asp Glu Glu
                435                 440                 445

Asp Glu
    450

<210> SEQ ID NO 3
<211> LENGTH: 2289
<212> TYPE: DNA
<213> ORGANISM: Rhipicephalus sanguineus
<220> FEATURE:
<221> NAME/KEY: CDS
<222> LOCATION: (502)...(1854)

<400> SEQUENCE: 3
cacacctcct gcgtctctcc actcgatgaa gacctgtccc ggaggcgcga gcccaactgc         60
gcgctctgtc cgcatgtgtc gccgccactg agaggcctcc ggcgtggcgc gcttgtcaac        120
gcggcgcgcc ggcccgcagc aaatcgcggg cattccactc agggtctcat tcgctccccc        180
aatcctgagg ttccttctaa cgagaaggag gagccacagc gccggctgcg gtaccgccgc        240
acgggccaac gtgagaccgc ccgagcccgg cgccctgact taggccgctg agcgaaaccc        300
aaggcggcgc gctggccact ccacgggaac gagaccggcc ccctggagac gacatcgtcg        360
accacaatga actacttctc tgacgtggcg aagatggtgg cttcatcgaa gagagaaatc        420
atcgaagctt ccacgcgac atctggagta cacggcgcat gcgaatgagc gaacatcgct        480
gaccgagact cgcccgtcac c atg agc gta cat tca tgg cgc ttt tgt gtc         531
                         Met Ser Val His Ser Trp Arg Phe Cys Val
                           1               5                  10 cca ctg gtg gct cta gcg ttt ttc ttg ttg att ctt ctg tcg tgt cca         579
Pro Leu Val Ala Leu Ala Phe Phe Leu Leu Ile Leu Leu Ser Cys Pro
             15                  20                  25 tcg gca tgg ggc aag gca aat ttc cgc gct ata gaa aag cgg ata ttg         627
Ser Ala Trp Gly Lys Ala Asn Phe Arg Ala Ile Glu Lys Arg Ile Leu
         30                  35                  40 gac agc atc att ggc cag ggt cgt tat gac tgc agg atc cgg ccc atg         675
Asp Ser Ile Ile Gly Gln Gly Arg Tyr Asp Cys Arg Ile Arg Pro Met
     45                  50                  55 gga att aac aac aca gac ggg ccg gct ctt gta cgc gtt aac atc ttt         723
Gly Ile Asn Asn Thr Asp Gly Pro Ala Leu Val Arg Val Asn Ile Phe
 60                  65                  70
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gta | aga | agt | atc | ggc | aga | att | gat | gac | gtc | acc | atg | gag | tac | aca | gtg | 771  |
| Val | Arg | Ser | Ile | Gly | Arg | Ile | Asp | Asp | Val | Thr | Met | Glu | Tyr | Thr | Val |      |
| 75  |     |     |     | 80  |     |     |     |     | 85  |     |     |     |     | 90  |     |      |
| caa | atg | acg | ttc | aga | gag | cag | tgg | cgg | gac | gag | aga | ctc | cag | tac | gac | 819  |
| Gln | Met | Thr | Phe | Arg | Glu | Gln | Trp | Arg | Asp | Glu | Arg | Leu | Gln | Tyr | Asp |      |
|     |     |     |     | 95  |     |     |     |     | 100 |     |     |     |     | 105 |     |      |
| gac | ttg | ggc | ggc | cag | gtt | cgc | tac | ctg | acg | ctc | acc | gaa | ccg | gac | aag | 867  |
| Asp | Leu | Gly | Gly | Gln | Val | Arg | Tyr | Leu | Thr | Leu | Thr | Glu | Pro | Asp | Lys |      |
|     |     |     | 110 |     |     |     |     | 115 |     |     |     |     | 120 |     |     |      |
| ctt | tgg | aag | ccg | gac | ctg | ttt | ttc | tcc | aac | gag | aaa | gag | gga | cac | ttc | 915  |
| Leu | Trp | Lys | Pro | Asp | Leu | Phe | Phe | Ser | Asn | Glu | Lys | Glu | Gly | His | Phe |      |
|     |     | 125 |     |     |     |     | 130 |     |     |     |     | 135 |     |     |     |      |
| cac | aac | atc | atc | atg | ccc | aac | gtg | ctt | cta | cgc | ata | cat | ccc | aac | ggc | 963  |
| His | Asn | Ile | Ile | Met | Pro | Asn | Val | Leu | Leu | Arg | Ile | His | Pro | Asn | Gly |      |
|     | 140 |     |     |     |     | 145 |     |     |     |     | 150 |     |     |     |     |      |
| gac | gtt | ctc | ttc | agc | atc | aga | ata | tcc | ttg | gtg | ctt | tca | tgt | ccg | atg | 1011 |
| Asp | Val | Leu | Phe | Ser | Ile | Arg | Ile | Ser | Leu | Val | Leu | Ser | Cys | Pro | Met |      |
| 155 |     |     |     |     | 160 |     |     |     |     | 165 |     |     |     |     | 170 |      |
| aac | ctg | aaa | ttt | tat | cct | ttg | gat | aaa | caa | atc | tgc | tct | atc | gtc | atg | 1059 |
| Asn | Leu | Lys | Phe | Tyr | Pro | Leu | Asp | Lys | Gln | Ile | Cys | Ser | Ile | Val | Met |      |
|     |     |     |     | 175 |     |     |     |     | 180 |     |     |     |     | 185 |     |      |
| gtg | agc | tat | ggg | tat | aca | aca | gag | gac | ctg | gtg | ttt | cta | tgg | aaa | gag | 1107 |
| Val | Ser | Tyr | Gly | Tyr | Thr | Thr | Glu | Asp | Leu | Val | Phe | Leu | Trp | Lys | Glu |      |
|     |     |     | 190 |     |     |     |     | 195 |     |     |     |     | 200 |     |     |      |
| ggg | gat | cct | gta | cag | gtc | aca | aaa | aat | ctc | cac | ttg | cca | cgt | ttc | acg | 1155 |
| Gly | Asp | Pro | Val | Gln | Val | Thr | Lys | Asn | Leu | His | Leu | Pro | Arg | Phe | Thr |      |
|     |     | 205 |     |     |     |     | 210 |     |     |     |     | 215 |     |     |     |      |
| ctg | gaa | agg | ttt | caa | acc | gac | tac | tgc | acc | agt | cgg | acc | aac | act | ggc | 1203 |
| Leu | Glu | Arg | Phe | Gln | Thr | Asp | Tyr | Cys | Thr | Ser | Arg | Thr | Asn | Thr | Gly |      |
|     | 220 |     |     |     |     | 225 |     |     |     |     | 230 |     |     |     |     |      |
| gag | tac | agc | tgc | ttg | cgc | gtg | gac | ctg | gtg | ttc | aag | cgc | gag | ttc | agc | 1251 |
| Glu | Tyr | Ser | Cys | Leu | Arg | Val | Asp | Leu | Val | Phe | Lys | Arg | Glu | Phe | Ser |      |
| 235 |     |     |     |     | 240 |     |     |     |     | 245 |     |     |     |     | 250 |      |
| tac | tac | ctg | atc | cag | atc | tac | atc | ccg | tgc | tgc | atg | ctg | gtc | atc | gtg | 1299 |
| Tyr | Tyr | Leu | Ile | Gln | Ile | Tyr | Ile | Pro | Cys | Cys | Met | Leu | Val | Ile | Val |      |
|     |     |     |     | 255 |     |     |     |     | 260 |     |     |     |     | 265 |     |      |
| tcc | tgg | gtg | tcg | ttc | tgg | ctc | gac | ccc | acc | tcg | atc | ccg | gcg | cga | gtg | 1347 |
| Ser | Trp | Val | Ser | Phe | Trp | Leu | Asp | Pro | Thr | Ser | Ile | Pro | Ala | Arg | Val |      |
|     |     |     | 270 |     |     |     |     | 275 |     |     |     |     | 280 |     |     |      |
| tcg | ctg | ggc | gtc | acc | acc | ctg | ctc | acc | atg | gcc | acg | cag | ata | tcg | ggc | 1395 |
| Ser | Leu | Gly | Val | Thr | Thr | Leu | Leu | Thr | Met | Ala | Thr | Gln | Ile | Ser | Gly |      |
|     |     | 285 |     |     |     |     | 290 |     |     |     |     | 295 |     |     |     |      |
| atc | aac | gcc | tcg | ctg | cct | ccc | gtt | tcc | tac | acc | aag | gcc | att | gac | gtg | 1443 |
| Ile | Asn | Ala | Ser | Leu | Pro | Pro | Val | Ser | Tyr | Thr | Lys | Ala | Ile | Asp | Val |      |
|     | 300 |     |     |     |     | 305 |     |     |     |     | 310 |     |     |     |     |      |
| tgg | acc | ggc | gtc | tgt | ctg | acc | ttc | gta | ttc | ggc | gcg | ctc | ctc | gag | ttc | 1491 |
| Trp | Thr | Gly | Val | Cys | Leu | Thr | Phe | Val | Phe | Gly | Ala | Leu | Leu | Glu | Phe |      |
| 315 |     |     |     | 320 |     |     |     |     | 325 |     |     |     |     | 330 |     |      |
| gcc | ctg | gtc | aac | tac | gcc | tcg | cgg | tca | gat | tca | cgc | cgg | cag | aac | atg | 1539 |
| Ala | Leu | Val | Asn | Tyr | Ala | Ser | Arg | Ser | Asp | Ser | Arg | Arg | Gln | Asn | Met |      |
|     |     |     |     | 335 |     |     |     |     | 340 |     |     |     |     | 345 |     |      |
| cag | aag | cag | aag | cag | agg | aaa | tgg | gag | ctc | gag | ccg | ccc | ctg | gac | tcg | 1587 |
| Gln | Lys | Gln | Lys | Gln | Arg | Lys | Trp | Glu | Leu | Glu | Pro | Pro | Leu | Asp | Ser |      |
|     |     |     | 350 |     |     |     |     | 355 |     |     |     |     | 360 |     |     |      |
| gac | cac | ctg | gag | gac | ggc | gcc | acc | acg | ttc | gcc | atg | agg | ccg | ctg | gtg | 1635 |
| Asp | His | Leu | Glu | Asp | Gly | Ala | Thr | Thr | Phe | Ala | Met | Arg | Pro | Leu | Val |      |
|     |     | 365 |     |     |     |     | 370 |     |     |     |     | 375 |     |     |     |      |
| cac | cac | cac | gga | gag | ctg | cat | gcc | gac | aag | ttg | cgg | cag | tgc | gaa | gtc | 1683 |
| His | His | His | Gly | Glu | Leu | His | Ala | Asp | Lys | Leu | Arg | Gln | Cys | Glu | Val |      |
|     | 380 |     |     |     |     | 385 |     |     |     |     | 390 |     |     |     |     |      |

-continued

```
cac atg aag acc ccc aag acg aac ctt tgc aag gcc tgg ctt tcc agg    1731
His Met Lys Thr Pro Lys Thr Asn Leu Cys Lys Ala Trp Leu Ser Arg
395                 400                 405                 410 ttt ccc acg cga tcc aaa cgc atc gac gtc gtc tcg cgg atc ttc ttt    1779
Phe Pro Thr Arg Ser Lys Arg Ile Asp Val Val Ser Arg Ile Phe Phe
            415                 420                 425 ccg ctc atg ttc gcc ctc ttc aac ctc gtc tac tgg aca acc tac ctc    1827
Pro Leu Met Phe Ala Leu Phe Asn Leu Val Tyr Trp Thr Thr Tyr Leu
        430                 435                 440 ttc cgg gaa gac aag gaa gac gag tga cagaacacga acgccacgac          1874
Phe Arg Glu Asp Lys Glu Asp Glu *
    445                 450 agccgccatc cgacaccatc gtcactgcag gcacgcactc tgtcgcgcgc acacaccacg  1934
aagaccggcg cgccaacgca cgatgcgcgt tggccgctga aaaacccggg agcggggcgg  1994
tgggggaggc tatgcccggg ccctcgctc tcatcctcc gtgcacgctc gaatcgtcat    2054
cgccacagcc agaaaaaaaa aagataccgt gcgaaaagtg gcggcaacac aacgtcgacg  2114
ccatcagcgc cgcccagagc tgcaagcggc tcccacatgg ttgccaccgc agcttcctct  2174
acgacccttc atccccaccg gcaccagcta cgagaaaggg accttatttc gggccatccc  2234
tacataggcg actgttgttt tcgcacgaaa gatctttacg cagctgatgc tgaaa       2289
```

<210> SEQ ID NO 4
<211> LENGTH: 450
<212> TYPE: PRT
<213> ORGANISM: Rhipicephalus sanguineus

<400> SEQUENCE: 4

```
Met Ser Val His Ser Trp Arg Phe Cys Val Pro Leu Val Ala Leu Ala
1               5                   10                  15

Phe Phe Leu Leu Ile Leu Leu Ser Cys Pro Ser Ala Trp Gly Lys Ala
            20                  25                  30

Asn Phe Arg Ala Ile Glu Lys Arg Ile Leu Asp Ser Ile Ile Gly Gln
        35                  40                  45

Gly Arg Tyr Asp Cys Arg Ile Arg Pro Met Gly Ile Asn Asn Thr Asp
    50                  55                  60

Gly Pro Ala Leu Val Arg Val Asn Ile Phe Val Arg Ser Ile Gly Arg
65                  70                  75                  80

Ile Asp Asp Val Thr Met Glu Tyr Thr Val Gln Met Thr Phe Arg Glu
                85                  90                  95

Gln Trp Arg Asp Glu Arg Leu Gln Tyr Asp Asp Leu Gly Gly Gln Val
            100                 105                 110

Arg Tyr Leu Thr Leu Thr Glu Pro Asp Lys Leu Trp Lys Pro Asp Leu
        115                 120                 125

Phe Phe Ser Asn Glu Lys Glu Gly His Phe His Asn Ile Ile Met Pro
    130                 135                 140

Asn Val Leu Leu Arg Ile His Pro Asn Gly Asp Val Leu Phe Ser Ile
145                 150                 155                 160

Arg Ile Ser Leu Val Leu Ser Cys Pro Met Asn Leu Lys Phe Tyr Pro
                165                 170                 175

Leu Asp Lys Gln Ile Cys Ser Ile Val Met Val Ser Tyr Gly Tyr Thr
            180                 185                 190

Thr Glu Asp Leu Val Phe Leu Trp Lys Glu Gly Asp Pro Val Gln Val
        195                 200                 205

Thr Lys Asn Leu His Leu Pro Arg Phe Thr Leu Glu Arg Phe Gln Thr
```

```
                210                 215                 220
Asp Tyr Cys Thr Ser Arg Thr Asn Thr Gly Glu Tyr Ser Cys Leu Arg
225                 230                 235                 240

Val Asp Leu Val Phe Lys Arg Glu Phe Ser Tyr Tyr Leu Ile Gln Ile
                245                 250                 255

Tyr Ile Pro Cys Cys Met Leu Val Ile Val Ser Trp Val Ser Phe Trp
            260                 265                 270

Leu Asp Pro Thr Ser Ile Pro Ala Arg Val Ser Leu Gly Val Thr Thr
        275                 280                 285

Leu Leu Thr Met Ala Thr Gln Ile Ser Gly Ile Asn Ala Ser Leu Pro
    290                 295                 300

Pro Val Ser Tyr Thr Lys Ala Ile Asp Val Trp Thr Gly Val Cys Leu
305                 310                 315                 320

Thr Phe Val Phe Gly Ala Leu Leu Glu Phe Ala Leu Val Asn Tyr Ala
                325                 330                 335

Ser Arg Ser Asp Ser Arg Arg Gln Asn Met Gln Lys Gln Lys Gln Arg
            340                 345                 350

Lys Trp Glu Leu Glu Pro Pro Leu Asp Ser Asp His Leu Glu Asp Gly
        355                 360                 365

Ala Thr Thr Phe Ala Met Arg Pro Leu Val His His Gly Glu Leu
    370                 375                 380

His Ala Asp Lys Leu Arg Gln Cys Glu Val His Met Lys Thr Pro Lys
385                 390                 395                 400

Thr Asn Leu Cys Lys Ala Trp Leu Ser Arg Phe Pro Thr Arg Ser Lys
                405                 410                 415

Arg Ile Asp Val Val Ser Arg Ile Phe Phe Pro Leu Met Phe Ala Leu
            420                 425                 430

Phe Asn Leu Val Tyr Trp Thr Thr Tyr Leu Phe Arg Glu Asp Lys Glu
        435                 440                 445

Asp Glu
    450

<210> SEQ ID NO 5
<211> LENGTH: 2400
<212> TYPE: DNA
<213> ORGANISM: Rhipicephalus sanguineus
<220> FEATURE:
<221> NAME/KEY: CDS
<222> LOCATION: (617)...(2170)

<400> SEQUENCE: 5
caggctccgg cgtgactgtc gctcgctcgg ctctcgacgc tcgcggcggg aacaaccgct      60
acccggacgc tcgatcagga gcagttcggg ccacagagaa aggggccgag gagtgcacac     120
ctcctgcgtc tctccactcg atgaagacct gtcccggagg cgcgagccca actgcgcgct     180
ctgtccgcat gtgtcgccgc cactgagagg cctccgcgt ggcgcgcttg tcaacgcggc     240
gcgccggccc gcagcaaatc gcgggcattc cactcagggt ctcattcgct ccccaatcc     300 tgaggttcct tctaacgaga aggaggagcc acagcgccgg ctgcgtacc gccgcacggg     360 ccaacgtgag accgccgag cccggcgccc tgacttaggc cgctgagcga acccaaggc     420 ggcgcgctgg ccactccacg ggaacgagac cggccccctg agacgacat cgtcgaccac     480 aatgaactac ttctctgacg tggcgaagat ggtggcttca tcgaagagag aaatcatcga     540
agctttccac gcgacatctg gagtacacgg cgcatgcgaa tgagcgaaca tcgctgaccg     600
agactcgccc gtcacc atg agc gta cat tca tgg cgc ttt tgt gtc cca ctg     652
```

```
                Met Ser Val His Ser Trp Arg Phe Cys Val Pro Leu
                  1           5                  10 gtg gct cta gcg ttt ttc ttg ttg att ctt ctg tcg tgt cca tcg gca      700
Val Ala Leu Ala Phe Phe Leu Leu Ile Leu Leu Ser Cys Pro Ser Ala
         15                  20                  25 tgg gcc gaa acg ctg cct acg cca cca acc cgt ggc cag ggg ggc gtt      748
Trp Ala Glu Thr Leu Pro Thr Pro Pro Thr Arg Gly Gln Gly Gly Val
     30                  35                  40 ccg gtc gcg gcc gcg atg ctc ctg ggg aaa cag caa agt tcc cgc tac      796
Pro Val Ala Ala Ala Met Leu Leu Gly Lys Gln Gln Ser Ser Arg Tyr
 45                  50                  55                  60 caa gat aaa gag ggc aag gca aat ttc cgc gct ata gaa aag cgg ata      844
Gln Asp Lys Glu Gly Lys Ala Asn Phe Arg Ala Ile Glu Lys Arg Ile
             65                  70                  75 ttg gac agc atc att ggc cag ggt cgt tat gac tgc agg atc cgg ccc      892
Leu Asp Ser Ile Ile Gly Gln Gly Arg Tyr Asp Cys Arg Ile Arg Pro
                 80                  85                  90 atg gga att aac aac aca gac ggg ccg gct ctt gta cgc gtt aac atc      940
Met Gly Ile Asn Asn Thr Asp Gly Pro Ala Leu Val Arg Val Asn Ile
                     95                  100                 105 ttt gta aga agt atc ggc aga att gat gac gtc acc atg gag tac aca      988
Phe Val Arg Ser Ile Gly Arg Ile Asp Asp Val Thr Met Glu Tyr Thr
110                 115                 120 gtg caa atg acg ttc aga gag cag tgg cgg gac gag aga ctc cag tac     1036
Val Gln Met Thr Phe Arg Glu Gln Trp Arg Asp Glu Arg Leu Gln Tyr
125                 130                 135                 140 gac gac ttg ggc ggc cag gtt cgc tac ctg acg ctc acc gaa ccg gac     1084
Asp Asp Leu Gly Gly Gln Val Arg Tyr Leu Thr Leu Thr Glu Pro Asp
                145                 150                 155 aag ctt tgg aag ccg gac ctg ttt ttc tcc aac gag aaa gag gga cac     1132
Lys Leu Trp Lys Pro Asp Leu Phe Phe Ser Asn Glu Lys Glu Gly His
                    160                 165                 170 ttc cac aac atc atc atg ccc aac gtg ctt cta cgc ata cat ccc aac     1180
Phe His Asn Ile Ile Met Pro Asn Val Leu Leu Arg Ile His Pro Asn
                        175                 180                 185 ggc gac gtt ctc ttc agc atc aga ata tcc ttg gtg ctt tca tgt ccg     1228
Gly Asp Val Leu Phe Ser Ile Arg Ile Ser Leu Val Leu Ser Cys Pro
    190                 195                 200 atg aac ctg aaa ttt tat cct ttg gat aaa caa atc tgc tct atc gtc     1276
Met Asn Leu Lys Phe Tyr Pro Leu Asp Lys Gln Ile Cys Ser Ile Val
205                 210                 215                 220 atg gtg agc tat ggg tat aca aca gag gac ctg gtg ttt cta tgg aaa     1324
Met Val Ser Tyr Gly Tyr Thr Thr Glu Asp Leu Val Phe Leu Trp Lys
                225                 230                 235 gag ggg gat cct gta cag gtc aca aaa aat ctc cac ttg cca cgt ttc     1372
Glu Gly Asp Pro Val Gln Val Thr Lys Asn Leu His Leu Pro Arg Phe
                    240                 245                 250 acg ctg gaa agg ttt caa acc gac tac tgc acc agt cgg acc aac act     1420
Thr Leu Glu Arg Phe Gln Thr Asp Tyr Cys Thr Ser Arg Thr Asn Thr
                        255                 260                 265 ggc gag tac agc tgc ttg cgc gtg gac ctg gtg ttc aag cgc gag ttc     1468
Gly Glu Tyr Ser Cys Leu Arg Val Asp Leu Val Phe Lys Arg Glu Phe
    270                 275                 280 agc tac tac ctg atc cag atc tac atc ccg tgc tgc atg ctg gtc atc     1516
Ser Tyr Tyr Leu Ile Gln Ile Tyr Ile Pro Cys Cys Met Leu Val Ile
285                 290                 295                 300 gtg tcc tgg gtg tcg ttc tgg ctc gac ccc acc tcg atc ccg gcg cga     1564
Val Ser Trp Val Ser Phe Trp Leu Asp Pro Thr Ser Ile Pro Ala Arg
                305                 310                 315
```

```
gtg tcg ctg ggc gtc acc acc ctg ctc acc atg gcc acg cag ata tcg    1612
Val Ser Leu Gly Val Thr Thr Leu Leu Thr Met Ala Thr Gln Ile Ser
        320                 325                 330 ggc atc aac gcc tcg ctg cct ccc gtt tcc tac acc aag gcc att gac    1660
Gly Ile Asn Ala Ser Leu Pro Pro Val Ser Tyr Thr Lys Ala Ile Asp
335                 340                 345 gtg tgg acc ggc gtc tgt ctg acc ttc gta ttc ggc gcg ctc ctc gag    1708
Val Trp Thr Gly Val Cys Leu Thr Phe Val Phe Gly Ala Leu Leu Glu
    350                 355                 360 ttc gcc ctg gtc aac tac gcc tcg cgg tca gat tca cgc cgg cag aac    1756
Phe Ala Leu Val Asn Tyr Ala Ser Arg Ser Asp Ser Arg Arg Gln Asn
365                 370                 375                 380 atg cag aag cag aag cag agg aaa tgg gag ctc gag ccg ccc ctg gac    1804
Met Gln Lys Gln Lys Gln Arg Lys Trp Glu Leu Glu Pro Pro Leu Asp
                385                 390                 395 tcg gac cac ctg gag gac ggc gcc acg acg ttc gcc atg gtg agc tcc    1852
Ser Asp His Leu Glu Asp Gly Ala Thr Thr Phe Ala Met Val Ser Ser
            400                 405                 410 ggc gag ccg gcg ggc ctc atg gcg cga acc tgg cca cca ccg ccg ctg    1900
Gly Glu Pro Ala Gly Leu Met Ala Arg Thr Trp Pro Pro Pro Pro Leu
        415                 420                 425 ccg cca aac atg gcg gcc ggc tcc gcg caa gcc ggc gcc agg ccg ctg    1948
Pro Pro Asn Met Ala Ala Gly Ser Ala Gln Ala Gly Ala Arg Pro Leu
    430                 435                 440 gtg cac cac cac gga gag ctg cat gcc gac aag ttg cgg cag tgc gaa    1996
Val His His His Gly Glu Leu His Ala Asp Lys Leu Arg Gln Cys Glu
445                 450                 455                 460 gtc cac atg aag acc ccc aag acg aac ctt tgc aag gcc tgg ctt tcc    2044
Val His Met Lys Thr Pro Lys Thr Asn Leu Cys Lys Ala Trp Leu Ser
                465                 470                 475 agg ttt ccc acg cga tcc aaa cgc atc gac gtc gtc tcg cgg atc ttc    2092
Arg Phe Pro Thr Arg Ser Lys Arg Ile Asp Val Val Ser Arg Ile Phe
            480                 485                 490 ttt ccg ctc gtg ttc gcc ctc ttc aac ctc gtc tac tgg aca acc tac    2140
Phe Pro Leu Val Phe Ala Leu Phe Asn Leu Val Tyr Trp Thr Thr Tyr
        495                 500                 505 ctc ttc cgg gaa gac gag gag gac gag tga cagaacacga acgccacgac      2190
Leu Phe Arg Glu Asp Glu Glu Asp Glu *
    510                 515 agccgccatc cgacaccatc gtcactgcag gcacgcactc tgtcgcgcgc acacaccacg  2250
aagaccggcg cgccaacgca cgatgcgcgt tggccgctga aaaacccggg agcggggcgg  2310
tgggggaggc tatgccccgg cccctcgctc ctcatcctcc gtgcacgctc gaatcgtcat  2370
cgccacagcc agaaaaaaaa aaaaaaaaa                                    2400

<210> SEQ ID NO 6
<211> LENGTH: 517
<212> TYPE: PRT
<213> ORGANISM: Rhipicephalus sanguineus

<400> SEQUENCE: 6

Met Ser Val His Ser Trp Arg Phe Cys Val Pro Leu Val Ala Leu Ala
1               5                   10                  15

Phe Phe Leu Leu Ile Leu Leu Ser Cys Pro Ser Ala Trp Ala Glu Thr
            20                  25                  30

Leu Pro Thr Pro Pro Thr Arg Gly Gln Gly Gly Val Pro Val Ala Ala
        35                  40                  45

Ala Met Leu Leu Gly Lys Gln Gln Ser Ser Arg Tyr Gln Asp Lys Glu
    50                  55                  60
```

```
Gly Lys Ala Asn Phe Arg Ala Ile Glu Lys Arg Ile Leu Asp Ser Ile
 65                  70                  75                  80

Ile Gly Gln Gly Arg Tyr Asp Cys Arg Ile Arg Pro Met Gly Ile Asn
                 85                  90                  95

Asn Thr Asp Gly Pro Ala Leu Val Arg Val Asn Ile Phe Val Arg Ser
            100                 105                 110

Ile Gly Arg Ile Asp Asp Val Thr Met Glu Tyr Thr Val Gln Met Thr
            115                 120                 125

Phe Arg Glu Gln Trp Arg Asp Glu Arg Leu Gln Tyr Asp Asp Leu Gly
        130                 135                 140

Gly Gln Val Arg Tyr Leu Thr Leu Thr Glu Pro Asp Lys Leu Trp Lys
145                 150                 155                 160

Pro Asp Leu Phe Phe Ser Asn Glu Lys Glu Gly His Phe His Asn Ile
                165                 170                 175

Ile Met Pro Asn Val Leu Leu Arg Ile His Pro Asn Gly Asp Val Leu
            180                 185                 190

Phe Ser Ile Arg Ile Ser Leu Val Leu Ser Cys Pro Met Asn Leu Lys
        195                 200                 205

Phe Tyr Pro Leu Asp Lys Gln Ile Cys Ser Ile Val Met Val Ser Tyr
            210                 215                 220

Gly Tyr Thr Thr Glu Asp Leu Val Phe Leu Trp Lys Glu Gly Asp Pro
225                 230                 235                 240

Val Gln Val Thr Lys Asn Leu His Leu Pro Arg Phe Thr Leu Glu Arg
                245                 250                 255

Phe Gln Thr Asp Tyr Cys Thr Ser Arg Thr Asn Thr Gly Glu Tyr Ser
            260                 265                 270

Cys Leu Arg Val Asp Leu Val Phe Lys Arg Glu Phe Ser Tyr Tyr Leu
        275                 280                 285

Ile Gln Ile Tyr Ile Pro Cys Cys Met Leu Val Ile Val Ser Trp Val
            290                 295                 300

Ser Phe Trp Leu Asp Pro Thr Ser Ile Pro Ala Arg Val Ser Leu Gly
305                 310                 315                 320

Val Thr Thr Leu Leu Thr Met Ala Thr Gln Ile Ser Gly Ile Asn Ala
                325                 330                 335

Ser Leu Pro Pro Val Ser Tyr Thr Lys Ala Ile Asp Val Trp Thr Gly
            340                 345                 350

Val Cys Leu Thr Phe Val Phe Gly Ala Leu Leu Glu Phe Ala Leu Val
        355                 360                 365

Asn Tyr Ala Ser Arg Ser Asp Ser Arg Arg Gln Asn Met Gln Lys Gln
            370                 375                 380

Lys Gln Arg Lys Trp Glu Leu Glu Pro Pro Leu Asp Ser Asp His Leu
385                 390                 395                 400

Glu Asp Gly Ala Thr Thr Phe Ala Met Val Ser Ser Gly Glu Pro Ala
                405                 410                 415

Gly Leu Met Ala Arg Thr Trp Pro Pro Pro Leu Pro Pro Asn Met
            420                 425                 430

Ala Ala Gly Ser Ala Gln Ala Gly Ala Arg Pro Leu Val His His His
        435                 440                 445

Gly Glu Leu His Ala Asp Lys Leu Arg Gln Cys Glu Val His Met Lys
            450                 455                 460

Thr Pro Lys Thr Asn Leu Cys Lys Ala Trp Leu Ser Arg Phe Pro Thr
465                 470                 475                 480
```

-continued

```
Arg Ser Lys Arg Ile Asp Val Val Ser Arg Ile Phe Phe Pro Leu Val
            485                 490                 495
Phe Ala Leu Phe Asn Leu Val Tyr Trp Thr Thr Tyr Leu Phe Arg Glu
        500                 505                 510
Asp Glu Asp Glu
        515

<210> SEQ ID NO 7
<211> LENGTH: 1402
<212> TYPE: DNA
<213> ORGANISM: Rhipicephalus sanguineus
<220> FEATURE:
<221> NAME/KEY: CDS
<222> LOCATION: (131)...(1385)

<400> SEQUENCE: 7
cgccgctcaa tcgcgggcta cggactcgtc gttcccggag gggcttggac cacagctcgc      60
tcgtcaccgt ggtggctggc cgcttcgcct ggcggtcctg cacgcacgct gtaacgaacg     120
tcgccacgcg atg ttt ggt gtg cca tgc tcc cgc gcc tgc cgc ctt gtg       169
           Met Phe Gly Val Pro Cys Ser Arg Ala Cys Arg Leu Val
           1               5                   10 gtg gtg ata gct gcg ttc tgc tgg ccg ccc gct ctg ccg ctc gta ccc       217
Val Val Ile Ala Ala Phe Cys Trp Pro Pro Ala Leu Pro Leu Val Pro
 15                  20                  25 ggg gga gtt tcc tcc aga gca aac gat ctg gac att ctg gac gag ctc       265
Gly Gly Val Ser Ser Arg Ala Asn Asp Leu Asp Ile Leu Asp Glu Leu
 30                  35                  40                  45 ctc aaa aac tac gat cga agg gcc ctg ccg agc agt cac ctc gga aat       313
Leu Lys Asn Tyr Asp Arg Arg Ala Leu Pro Ser Ser His Leu Gly Asn
                 50                  55                  60 gca act att gtg tca tgc gaa att tac ata cga agt ttt gga tca ata       361
Ala Thr Ile Val Ser Cys Glu Ile Tyr Ile Arg Ser Phe Gly Ser Ile
         65                  70                  75 aat cct tcg aac atg gac tac gaa gtc gac ctc tac ttc cgg cag tcg       409
Asn Pro Ser Asn Met Asp Tyr Glu Val Asp Leu Tyr Phe Arg Gln Ser
             80                  85                  90 tgg ctc gac gag cgg tta cgc aaa tcc acg cta tct cgt ccg ctc gac       457
Trp Leu Asp Glu Arg Leu Arg Lys Ser Thr Leu Ser Arg Pro Leu Asp
 95                 100                 105 ctt aat gac cca aag ctg gta caa atg ata tgg aag cca gaa gtt ttc       505
Leu Asn Asp Pro Lys Leu Val Gln Met Ile Trp Lys Pro Glu Val Phe
110                 115                 120                 125 ttt gcg aac gcg aaa cac gcc gag ttc caa tat gtg act gta cct aac       553
Phe Ala Asn Ala Lys His Ala Glu Phe Gln Tyr Val Thr Val Pro Asn
                 130                 135                 140 gtc ctc gtt agg atc aac ccg act gga ata atc ttg tac atg ttg cgg       601
Val Leu Val Arg Ile Asn Pro Thr Gly Ile Ile Leu Tyr Met Leu Arg
             145                 150                 155 tta aaa ctg agg ttc tcc tgc atg atg gac ctg tac cgg tac ccc atg       649
Leu Lys Leu Arg Phe Ser Cys Met Met Asp Leu Tyr Arg Tyr Pro Met
         160                 165                 170 gat tcc caa gtc tgc agc atc gaa att gcc tct ttt tcc aaa acc acc       697
Asp Ser Gln Val Cys Ser Ile Glu Ile Ala Ser Phe Ser Lys Thr Thr
     175                 180                 185 gaa gag ctg ctg ctg aaa tgg tcc gag agt cag cct gtc gtt ctc ttc       745
Glu Glu Leu Leu Leu Lys Trp Ser Glu Ser Gln Pro Val Val Leu Phe
190                 195                 200                 205 gat aac ctc aag ttg ccc cag ttt gaa ata gag aag gtg aac acg tcc       793
Asp Asn Leu Lys Leu Pro Gln Phe Glu Ile Glu Lys Val Asn Thr Ser
                 210                 215                 220
```

-continued

| | |
|---|---|
| tta tgc aaa gaa aag ttt cac ata ggg gaa tac agt tgc ctg aaa gcc<br>Leu Cys Lys Glu Lys Phe His Ile Gly Glu Tyr Ser Cys Leu Lys Ala<br>225                            230                        235 | 841 |
| gac ttc tat ctg cag cgt tcc ctc ggt tat cac atg gtg cag acc tat<br>Asp Phe Tyr Leu Gln Arg Ser Leu Gly Tyr His Met Val Gln Thr Tyr<br>240                            245                        250 | 889 |
| ctt ccg acc acg ctt atc gtg gtc atc tca tgg gtg tca ttc tgg ctc<br>Leu Pro Thr Thr Leu Ile Val Val Ile Ser Trp Val Ser Phe Trp Leu<br>255                            260                        265 | 937 |
| gac gta gac gcc ata ccc gcc cgt gtc acc ctg ggc gta acc acg ctg<br>Asp Val Asp Ala Ile Pro Ala Arg Val Thr Leu Gly Val Thr Thr Leu<br>270                         275                       280                       285 | 985 |
| ctc acc atc tca tcc aag ggt gcc ggt atc cag gga aac ctg cct ccc<br>Leu Thr Ile Ser Ser Lys Gly Ala Gly Ile Gln Gly Asn Leu Pro Pro<br>                        290                       295                       300 | 1033 |
| gtc tcg tac atc aag gcc atg gac gtc tgg ata gga tcc tgt act tcg<br>Val Ser Tyr Ile Lys Ala Met Asp Val Trp Ile Gly Ser Cys Thr Ser<br>                        305                       310                       315 | 1081 |
| ttt gtc ttt gcg gcc ctt cta gag ttc aca ttc gtc aac tat ctc tgg<br>Phe Val Phe Ala Ala Leu Leu Glu Phe Thr Phe Val Asn Tyr Leu Trp<br>                        320                       325                       330 | 1129 |
| agg cgg ctg ccc aat aag cgc cca tct tct gac gta ccg gtg acg gat<br>Arg Arg Leu Pro Asn Lys Arg Pro Ser Ser Asp Val Pro Val Thr Asp<br>335                            340                        345 | 1177 |
| ata cca agc gac ggc tca aag cat gac att gcg gca cag ctc gta ctc<br>Ile Pro Ser Asp Gly Ser Lys His Asp Ile Ala Ala Gln Leu Val Leu<br>350                         355                       360                       365 | 1225 |
| gac aag aat gga cac acc gaa gtt cgc acg ttg gtc caa gcg atg cca<br>Asp Lys Asn Gly His Thr Glu Val Arg Thr Leu Val Gln Ala Met Pro<br>                        370                       375                       380 | 1273 |
| cgc agc gtc gga aaa gtg aag gcc aag cag att gat caa ctc agc cga<br>Arg Ser Val Gly Lys Val Lys Ala Lys Gln Ile Asp Gln Leu Ser Arg<br>                        385                       390                       395 | 1321 |
| gtc gcc ttt ccc gct ctt ttt ctc ctc ttc aac ctc gtg tac tgg ccg<br>Val Ala Phe Pro Ala Leu Phe Leu Leu Phe Asn Leu Val Tyr Trp Pro<br>400                            405                        410 | 1369 |
| tac tac att aag tca t aaagaacgta gttttct<br>Tyr Tyr Ile Lys Ser<br>415 | 1402 |

<210> SEQ ID NO 8
<211> LENGTH: 418
<212> TYPE: PRT
<213> ORGANISM: Rhipicephalus sanguineus

<400> SEQUENCE: 8

Met Phe Gly Val Pro Cys Ser Arg Ala Cys Arg Leu Val Val Val Ile
1                 5                     10                   15

Ala Ala Phe Cys Trp Pro Pro Ala Leu Pro Leu Val Pro Gly Gly Val
                20                   25                   30

Ser Ser Arg Ala Asn Asp Leu Asp Ile Leu Asp Glu Leu Leu Lys Asn
            35                   40                   45

Tyr Asp Arg Arg Ala Leu Pro Ser Ser His Leu Gly Asn Ala Thr Ile
50                      55                   60

Val Ser Cys Glu Ile Tyr Ile Arg Ser Phe Gly Ser Ile Asn Pro Ser
65                 70                   75                   80

Asn Met Asp Tyr Glu Val Asp Leu Tyr Phe Arg Gln Ser Trp Leu Asp
                85                   90                   95

Glu Arg Leu Arg Lys Ser Thr Leu Ser Arg Pro Leu Asp Leu Asn Asp
            100                 105                 110

Pro Lys Leu Val Gln Met Ile Trp Lys Pro Glu Val Phe Ala Asn
        115                 120                 125

Ala Lys His Ala Glu Phe Gln Tyr Val Thr Val Pro Asn Val Leu Val
    130                 135                 140

Arg Ile Asn Pro Thr Gly Ile Ile Leu Tyr Met Leu Arg Leu Lys Leu
145                 150                 155                 160

Arg Phe Ser Cys Met Met Asp Leu Tyr Arg Tyr Pro Met Asp Ser Gln
                165                 170                 175

Val Cys Ser Ile Glu Ile Ala Ser Phe Ser Lys Thr Thr Glu Glu Leu
            180                 185                 190

Leu Leu Lys Trp Ser Glu Ser Gln Pro Val Val Leu Phe Asp Asn Leu
        195                 200                 205

Lys Leu Pro Gln Phe Glu Ile Glu Lys Val Asn Thr Ser Leu Cys Lys
    210                 215                 220

Glu Lys Phe His Ile Gly Glu Tyr Ser Cys Leu Lys Ala Asp Phe Tyr
225                 230                 235                 240

Leu Gln Arg Ser Leu Gly Tyr His Met Val Gln Thr Tyr Leu Pro Thr
                245                 250                 255

Thr Leu Ile Val Val Ile Ser Trp Val Ser Phe Trp Leu Asp Val Asp
            260                 265                 270

Ala Ile Pro Ala Arg Val Thr Leu Gly Val Thr Thr Leu Leu Thr Ile
        275                 280                 285

Ser Ser Lys Gly Ala Gly Ile Gln Gly Asn Leu Pro Pro Val Ser Tyr
    290                 295                 300

Ile Lys Ala Met Asp Val Trp Ile Gly Ser Cys Thr Ser Phe Val Phe
305                 310                 315                 320

Ala Ala Leu Leu Glu Phe Thr Phe Val Asn Tyr Leu Trp Arg Arg Leu
                325                 330                 335

Pro Asn Lys Arg Pro Ser Ser Asp Val Pro Val Thr Asp Ile Pro Ser
            340                 345                 350

Asp Gly Ser Lys His Asp Ile Ala Ala Gln Leu Val Leu Asp Lys Asn
        355                 360                 365

Gly His Thr Glu Val Arg Thr Leu Val Gln Ala Met Pro Arg Ser Val
    370                 375                 380

Gly Lys Val Lys Ala Lys Gln Ile Asp Gln Leu Ser Arg Val Ala Phe
385                 390                 395                 400

Pro Ala Leu Phe Leu Leu Phe Asn Leu Val Tyr Trp Pro Tyr Tyr Ile
                405                 410                 415

Lys Ser

<210> SEQ ID NO 9
<211> LENGTH: 27
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (1)...(27)
<223> OTHER INFORMATION: n = A,T,C or G

<400> SEQUENCE: 9
ggatkccnga ynynttyttn nmnamyg                                    27

-continued

```
<210> SEQ ID NO 10
<211> LENGTH: 24
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (1)...(24)
<223> OTHER INFORMATION: n = A,T,C or G

<400> SEQUENCE: 10
cnarmarngc ncmgaanayr aayg                                              24

<210> SEQ ID NO 11
<211> LENGTH: 26
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (1)...(26)
<223> OTHER INFORMATION: n = A,T,C or G

<400> SEQUENCE: 11
canrcnccnr kccanacrtc naynrc                                            26

<210> SEQ ID NO 12
<211> LENGTH: 248
<212> TYPE: DNA
<213> ORGANISM: Drosophila melanogaster

<400> SEQUENCE: 12
attacttaat acaaatttat ataccatgct gtatgttggt cattgtatca tgggtatcat       60
tctggctgga tcaaggagca gtaccggcgc gagtgtcact gggtgtcacc accctgctga      120
ccatggccac ccagacgtcg ggcataaacg cctccctgcc gcccgtttcc tatacgaagg      180
ccatcgatgt gtggacaggc gtgtgtctga cgttcgtgtt cggggccctg ctcgagttcg      240
ccctggtg                                                              248
```